US010454039B2

(12) United States Patent
Lu et al.

(10) Patent No.: US 10,454,039 B2
(45) Date of Patent: Oct. 22, 2019

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Tai-Ni Lu, Jhubei (TW); Liang-Di Liao, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 185 days.

(21) Appl. No.: 15/670,464

(22) Filed: Aug. 7, 2017

(65) Prior Publication Data

US 2018/0047918 A1 Feb. 15, 2018

Related U.S. Application Data

(60) Provisional application No. 62/372,417, filed on Aug. 9, 2016.

(51) Int. Cl.
*H01L 51/00* (2006.01)
*C07D 307/94* (2006.01)
(Continued)

(52) U.S. Cl.
CPC ........ *H01L 51/0057* (2013.01); *C07B 59/002* (2013.01); *C07C 255/50* (2013.01); (Continued)

(58) Field of Classification Search
CPC . H01L 51/0057; C07D 307/94; C07D 333/80; C07D 405/04; C07D 409/02; C07D 409/14
See application file for complete search history.

(56) References Cited

FOREIGN PATENT DOCUMENTS

| | | |
|---|---|---|
| CN | 105778891 A | 7/2016 |
| CN | 106467740 A | 3/2017 |

OTHER PUBLICATIONS

Computer-generated English-language translation of CN105778891A.*

(Continued)

*Primary Examiner* — Vu A Nguyen
(74) *Attorney, Agent, or Firm* — Birch, Stewart, Kolasch & Birch, LLP

(57) ABSTRACT

Provided are a novel compound and an organic electronic device using the same. The novel compound is represented by the following Formula (I):

Formula (I)

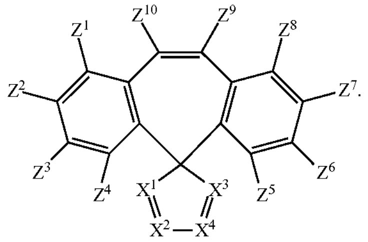

wherein $X^1$ and $X^2$ are each independently $C(R^a)$, the two $(R^a)$s are the same or different, and the two $(R^a)$s are joined together to form an aryl ring; $X^3$ and $X^4$ are each independently $C(R^b)$, the two $(R^b)$s are the same or different, and the two $(R^b)$s are joined together to form a heteroaryl ring containing at least one furan group or at least one thiophene group.

16 Claims, 18 Drawing Sheets

(51) Int. Cl.

| | |
|---|---|
| *C07D 333/80* | (2006.01) |
| *C07D 405/04* | (2006.01) |
| *C07D 409/04* | (2006.01) |
| *C07C 255/50* | (2006.01) |
| *C07C 255/51* | (2006.01) |
| *C07D 213/57* | (2006.01) |
| *C07D 233/58* | (2006.01) |
| *C07D 239/74* | (2006.01) |
| *C07D 251/24* | (2006.01) |
| *C07B 59/00* | (2006.01) |
| *C07D 409/14* | (2006.01) |
| *H01L 51/50* | (2006.01) |
| *H01L 51/52* | (2006.01) |

(52) U.S. Cl.

CPC .......... *C07C 255/51* (2013.01); *C07D 213/57* (2013.01); *C07D 233/58* (2013.01); *C07D 239/74* (2013.01); *C07D 251/24* (2013.01); *C07D 307/94* (2013.01); *C07D 333/80* (2013.01); *C07D 405/04* (2013.01); *C07D 409/04* (2013.01); *C07D 409/14* (2013.01); *H01L 51/0065* (2013.01); *H01L 51/0067* (2013.01); *H01L 51/0072* (2013.01); *H01L 51/0073* (2013.01); *H01L 51/0074* (2013.01); *C07B 2200/05* (2013.01); *H01L 51/001* (2013.01); *H01L 51/006* (2013.01); *H01L 51/0061* (2013.01); *H01L 51/0077* (2013.01); *H01L 51/0085* (2013.01); *H01L 51/5012* (2013.01); *H01L 51/5016* (2013.01); *H01L 51/5056* (2013.01); *H01L 51/5072* (2013.01); *H01L 51/5076* (2013.01); *H01L 51/5088* (2013.01); *H01L 51/5092* (2013.01); *H01L 51/5096* (2013.01); *H01L 51/5206* (2013.01); *H01L 51/5221* (2013.01)

(56) References Cited

OTHER PUBLICATIONS

Computer-generated English-language translation of CN-106467740A (Jun. 2016).*
SciFinder Search (Apr. 2019).*

* cited by examiner

COMPOUND AND ORGANIC ELECTRONIC DEVICE USING THE SAME

CROSS-REFERENCE TO RELATED APPLICATION

Pursuant to 35 U.S.C. § 119(e), this application claims the benefits of the priority to U.S. Provisional Patent Application No. 62/372,417, filed Aug. 9, 2016. The contents of the prior applications are incorporated herein by its entirety.

BACKGROUND OF THE INVENTION

1. Field of the Invention

The present invention relates to a novel compound and an organic electronic device using the same, more particularly to a novel compound as electron-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching W. Tang and Steven VanSlyke of Kodak Company deposited an electron transport material such as tris(8-hydroxyquinoline)aluminum(III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to modify the materials of ETL for OLEDs to render the electron transport materials to exhibit hole-blocking ability. Examples of conventional electron transport materials include 3,3'-[5'-[3-(3-Pyridinyl)phenyl][1,1':3',1"-terphenyl ]-3,3"-diyl]bispyridine (TmPyPb), 3-(Biphenyl-4-yl)-5-(4-tert-butylphenyl)-4-phenyl-4H-1,2,4-triazole (TAZ), 1,3,5-tris(1-phenyl-1H-benzimidazol-2-yl)benzene (TPBi), tris(2,4,6-trimethyl-3-(pyridin-3-yl)phenyl)borane (3TPYMB), 1,3-bis(3,5-dipyrid-3-yl-phenyl)benzene (BmPyPb), and 9,10-bis(3-(pyridin-3-yl)phenyl)anthracene (DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

Formula (I)

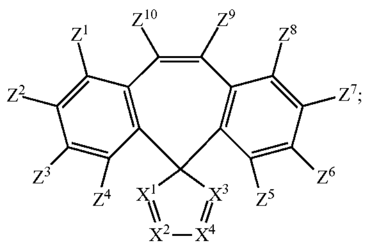

In Formula (I), $X^1$ and $X^2$ are each independently $C(R^a)$, the two $(R^a)$s are the same or different, and the two $(R^a)$s are joined together to form an aryl ring.

In Formula (I), $X^3$ and $X^4$ are each independently $C(R^b)$, the two $(R^b)$s are the same or different, and the two $(R^b)$s are joined together to form a heteroaryl ring containing at least one furan group or at least one thiophene group.

In Formula (I), $Z^1$ to $Z^{10}$ are each independently selected from the group consisting of: a hydrogen atom, a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

In accordance with the present invention, the double bond between $X^1$ and $X^2$ in Formula (I) and the bonds between the two joined $(R^a)$s are conjugated and commonly construct the aryl ring. Likely, the double bond between $X^3$ and $X^4$ in Formula (I) and the bonds between the two joined $(R^b)$s are conjugated and commonly construct the heteroaryl ring. In accordance with the present invention, the aryl ring extended from $X^1$ and $X^2$ and the heteroaryl ring extended from $X^3$ and $X^4$ are joined and fused, and the double bonds on the aryl ring and the heteroaryl ring are conjugated.

Preferably, $Z^1$ to $Z^{10}$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 30 ring carbon atoms, an alkoxy group having 1 to 12 carbon atoms, an aryloxy group having 6 to 30 ring carbon atoms, an alkylsilyl group having 1 to 12 carbon atoms, an arylsilyl group having 6 to 30 ring carbon atoms, an alkylboron group having 1 to 12 carbon atoms, an arylboron group having 6 to 30 ring carbon atoms, a phosphine group having 1 to 12 carbon atoms, and a phosphine oxide group having 1 to 12 carbon atoms.

Preferably, the heteroaryl ring extended from $X^3$ and $X^4$ in Formula (I) may contain at least one furan group. For example, the heteroaryl ring may be, but not limited to, benzofuran ring, dibenzofuran ring, or napththofuran ring.

In the case that the heteroaryl ring extended from $X^3$ and $X^4$ contains at least one furan group, the compound may be, for example, represented by Formula (I-I)

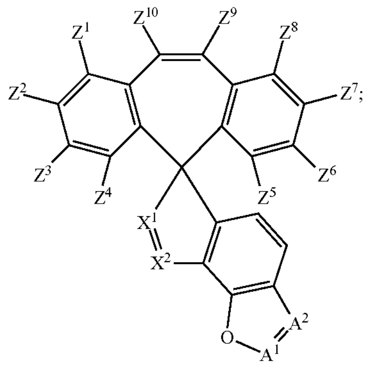

Formula (I-II)

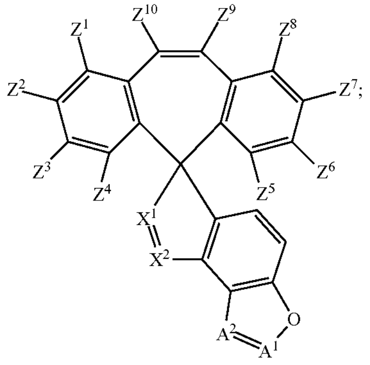

-continued

Formula (I-III)

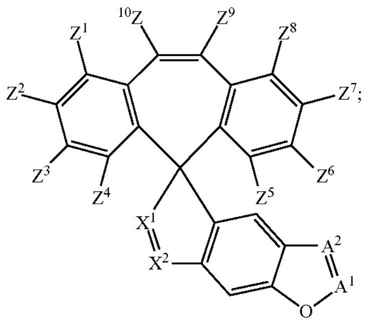

Formula (I-IV)

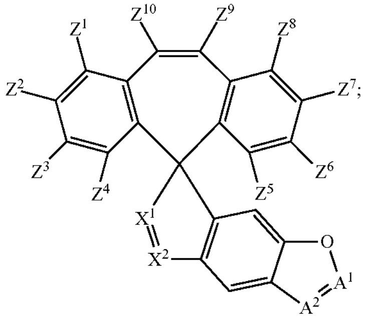

Formula (I-V)

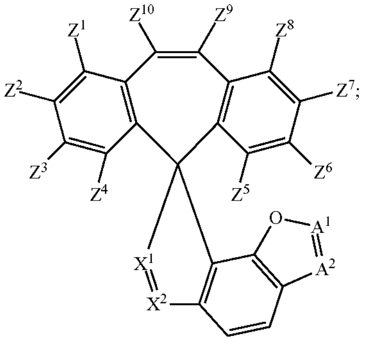

or

Formula (I-VI)

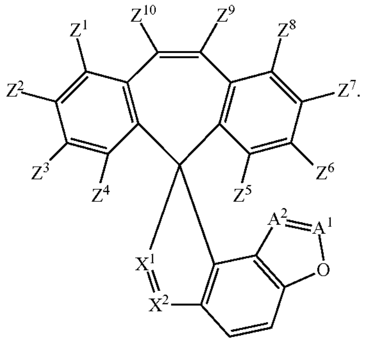

Preferably, the heteroaryl ring extended from $X^3$ and $X^4$ in Formula (I) may contain at least one thiophene group. For example, the heteroaryl ring may be, but not limited to, benzothiophene ring, dibenzothiophene ring, or napththothiophene ring.

In the case that the heteroaryl ring extended from $X^3$ and $X^4$ contains at least one thiophene group, the compound may be, for example, represented by Formula (I-VII)

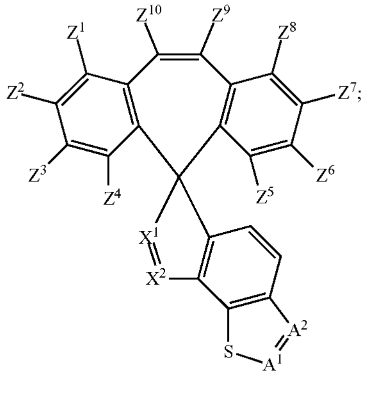

Formula (I-VIII)

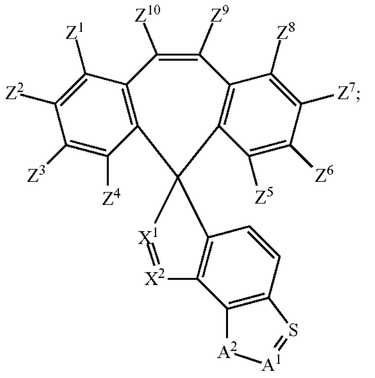

Formula (I-IX)

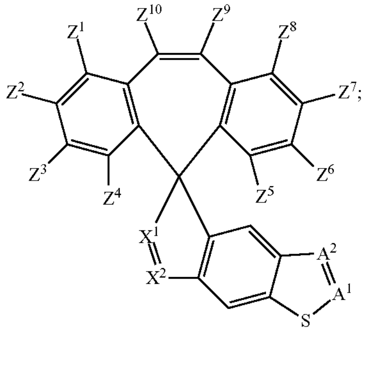

Formula (I-X)

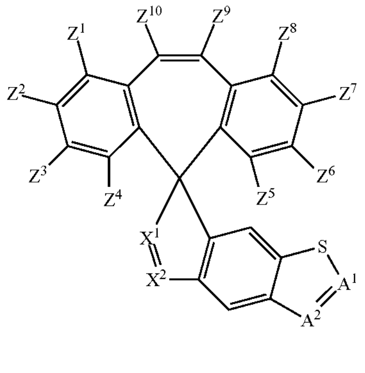

-continued

Formula (I-XI)

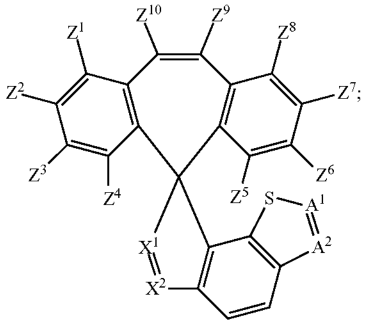

or

Formula (I-XII)

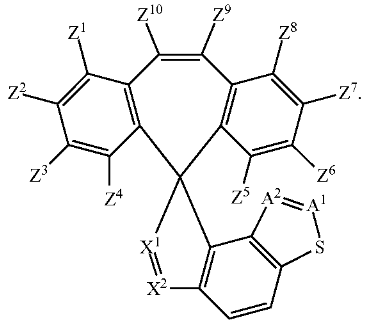

In accordance with the present invention, the foresaid $A^1$ and $A^2$ are each independently $C(R^c)$, the two $(R^c)$s are the same or different, and the two $(R^c)$s are joined together to form an aromatic structure contained in the heteroaryl ring.

Preferably, the aromatic structure may be a substituted or unsubstituted 6 to 20-membered carbon aromatic cyclic structure, for example, but not limited to, a substituted or unsubstituted benzene structure, a substituted or unsubstituted naphthalene structure, a substituted or unsubstituted anthracene structure, a substituted or unsubstituted phenanthrene structure, a substituted or unsubstituted fluorene structure, a substituted or unsubstituted pyrene structure, a substituted or unsubstituted benzophenanthrene structure, a substituted or unsubstituted benzopyrene structure, a substituted or unsubstituted fluoranthene structure, or a substituted or unsubstituted benzofluoranthene structure. The substitution group on the 6 to 20-membered carbon aromatic cyclic structure may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, the aryl ring extended from $X^1$ and $X^2$ in Formula (I) is a substituted or unsubstituted 6 to 60-membered carbon ring, more preferably, a substituted or unsubstituted 6 to 20-membered carbon ring. For example, the substituted or unsubstituted 6 to 60-membered carbon ring may be a substituted or unsubstituted benzene ring, a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, or a substituted or unsubstituted benzofluoranthene ring, but is not limited thereto. More preferably, the substituted or unsubstituted 6 to 60-membered carbon ring is a substituted or unsubstituted benzene structure. The substitution group on the 6 to 60-membered carbon ring may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, at least one of $Z^1$ to $Z^8$ in formula (I) may be selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 carbon atoms and substituted with at least one functional group, and a phosphine oxide group having 1 to 40 carbon atoms and substituted with at least one functional group; and the other of $Z^1$ to $Z^8$ in formula (I) may be hydrogen atom, a deuterium atom, or any other substitution groups as mentioned in the specification. Said functional group is selected from the group consisting of: a cyano group, a nitro group, a trifluoromethyl group, a fluoro group, and a chloro group.

More specifically, at least one of $Z^1$ to $Z^8$ in Formula (I) may be a specific aromatic substitution. The specific aromatic substitution may be selected from the group consisting of:

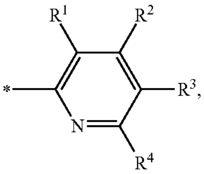,
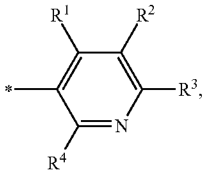,
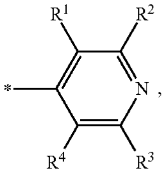,
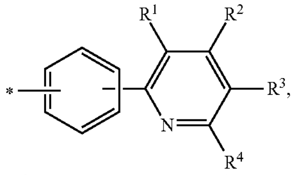,
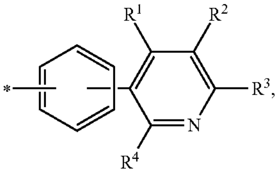,
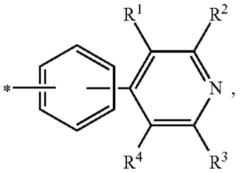,
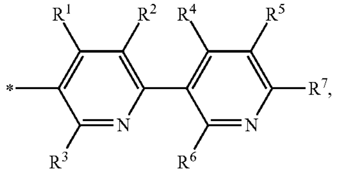, -continued

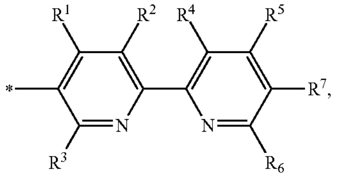,
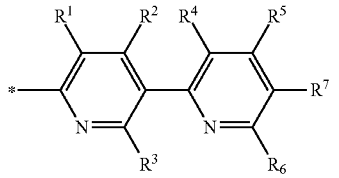
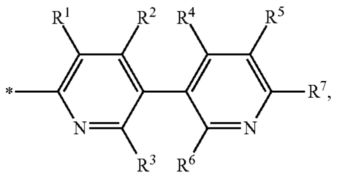,
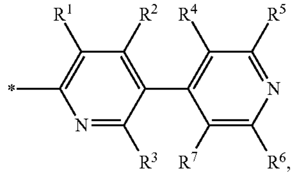,
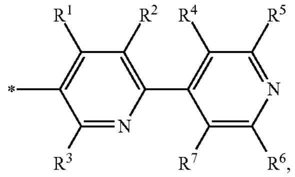,
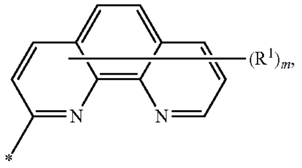,
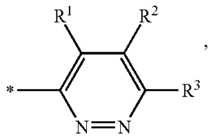
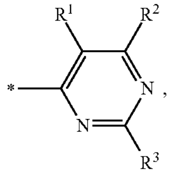,
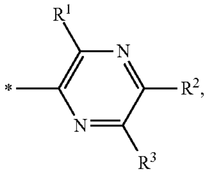,
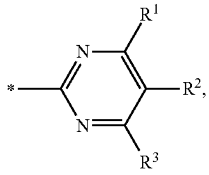,
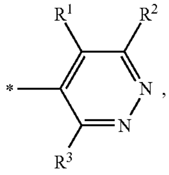,
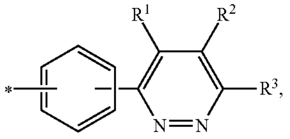,
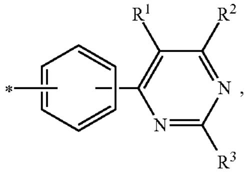,
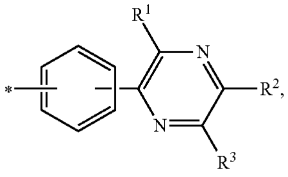, -continued
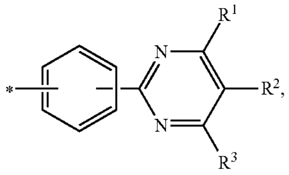
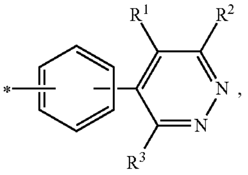
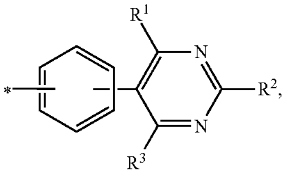
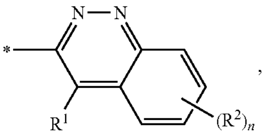
,
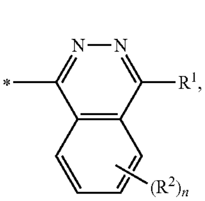
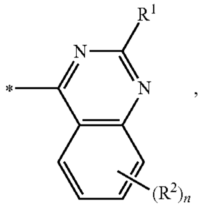
,
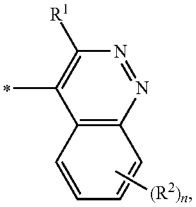
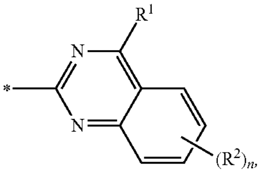
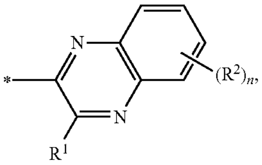
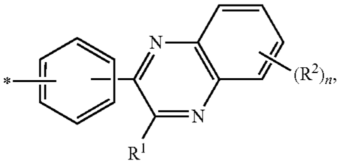
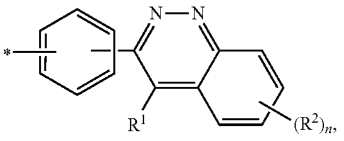
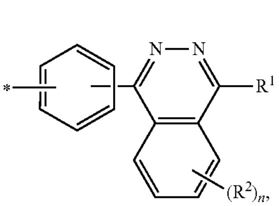
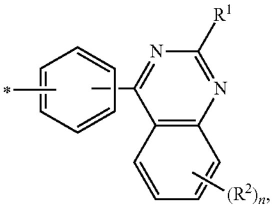
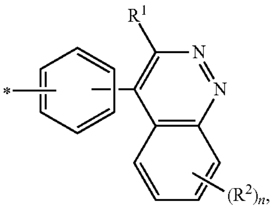
-continued
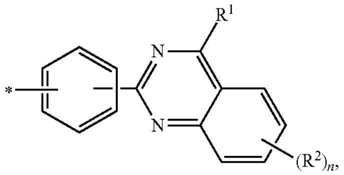
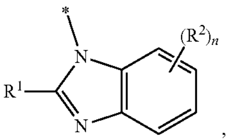
,
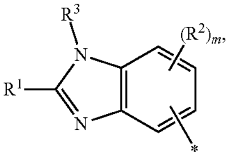
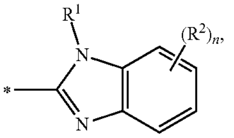
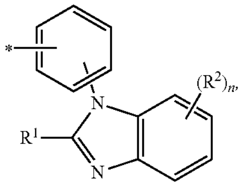
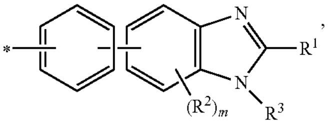
,
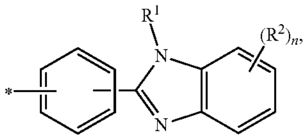
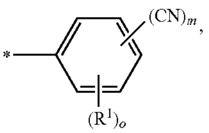
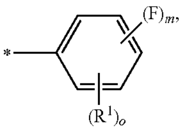
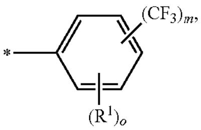
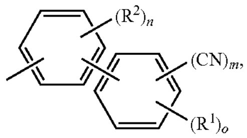
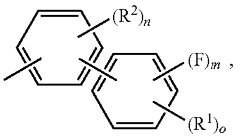
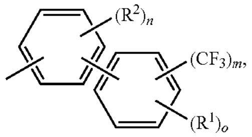
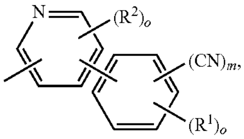
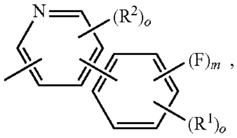
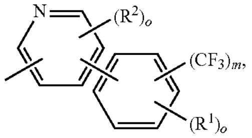
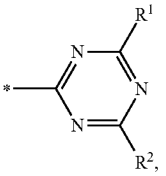
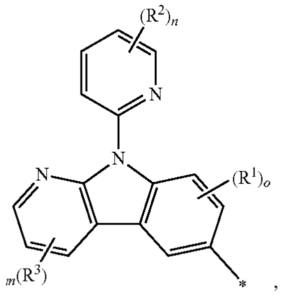
, -continued

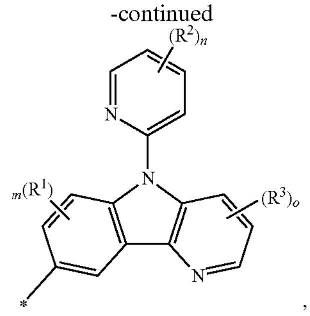
,

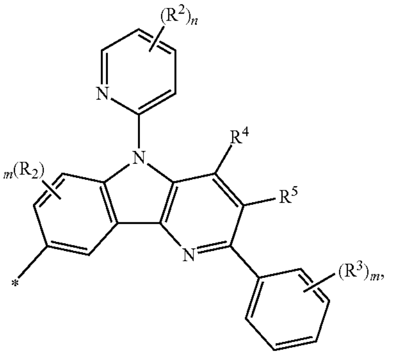

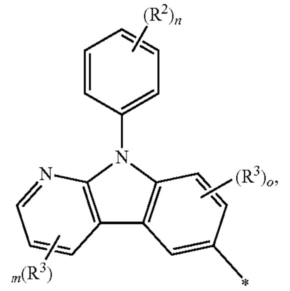

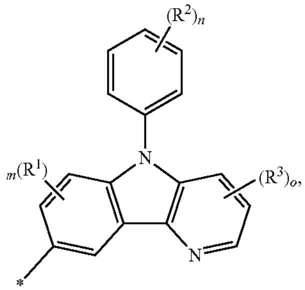
and

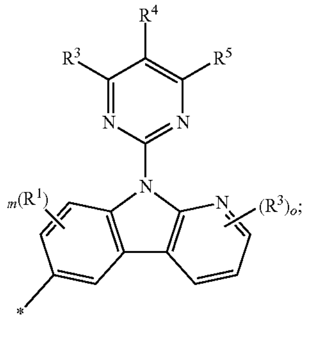
;

wherein $R^1$ to $R^7$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

n is a positive integral from 0 to 4, m is a positive integral from 0 to 3, o is a positive integral from 0 to 3, and the total of m and o is not more than 5.

Preferably, $R^1$ to $R^3$ each may independently be, for example, but not limited to, phenyl group, pyridine group, pyrimidine group, pyrazine group, pyridazine group, phenylpyridine group, phenylpyrimidine group, phenylpyrazine group, or phenylpyridazine group.

Preferably, at least one of $Z^1$, $Z^2$, $Z^3$, $Z^6$, $Z^7$, and $Z^8$ in Formula (I) may be the specific aromatic substitution as stated above, and $Z^4$ and $Z^5$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms. Or, at least one of $Z^2$, $Z^3$, $Z^6$, and $Z^7$ in Formula (I) may be the specific aromatic substitution as stated above, and $Z^1$, $Z^4$, $Z^5$, $Z^8$ are each independently selected from the group consisting of: a hydrogen atom, a deuterium atom, an alkyl group having 1 to 12 carbon atoms, an alkenyl group having 2 to 12 carbon atoms, and an alkynyl group having 2 to 12 carbon atoms.

Preferably, at least one of $Z^2$, $Z^3$, $Z^6$, and $Z^7$ in Formula (I) is selected from the group consisting of:

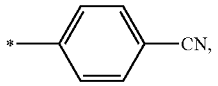
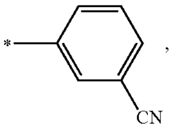
,
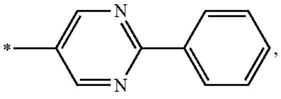
,
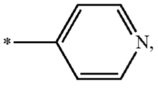
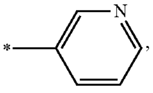
,
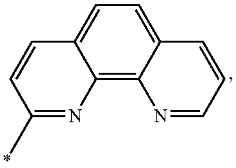
,
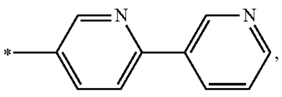
,
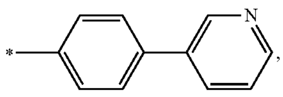
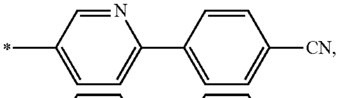
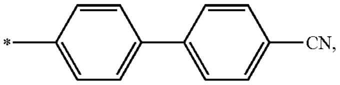

-continued
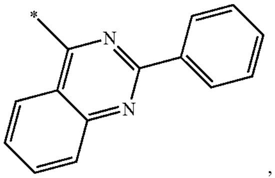
,
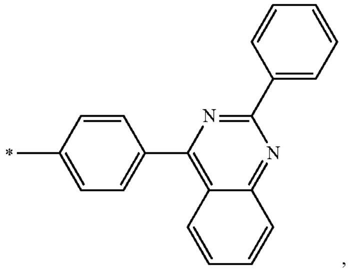
,
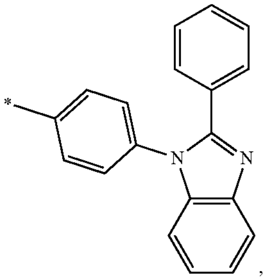
,
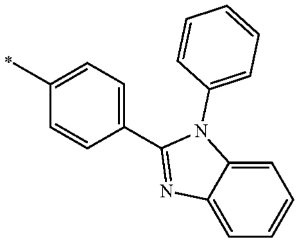
,
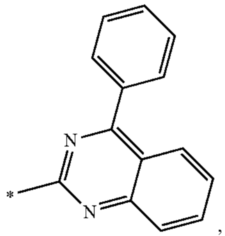
,
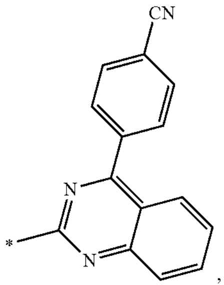
,
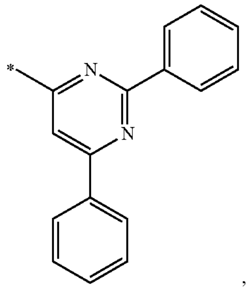
,
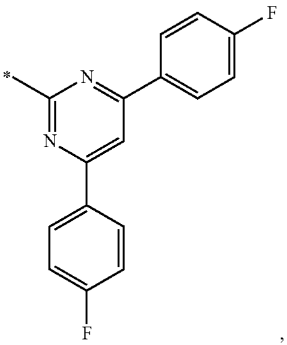
,
-continued
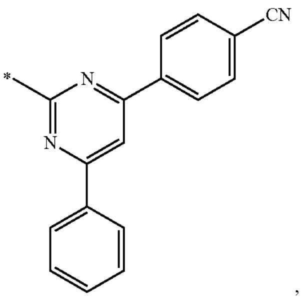
,
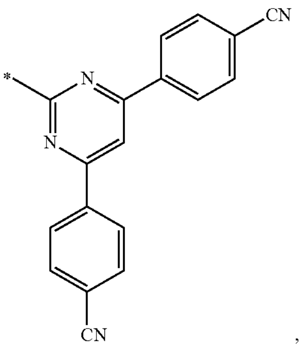
,
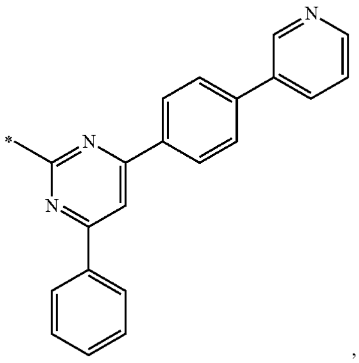
,
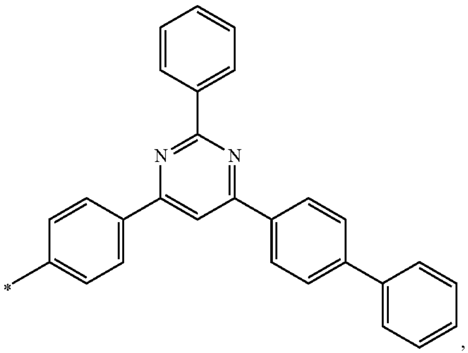
, -continued

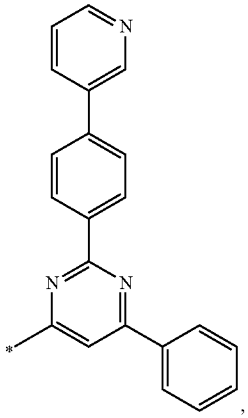,
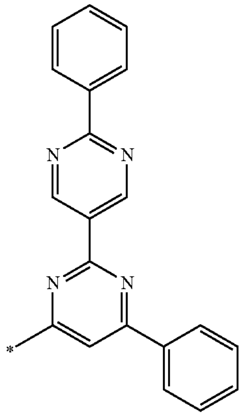,

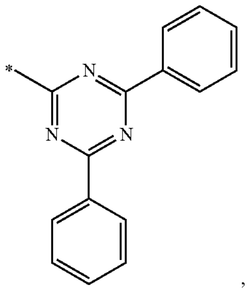,
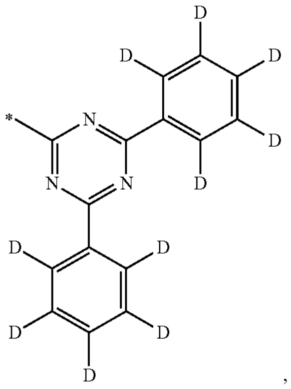,

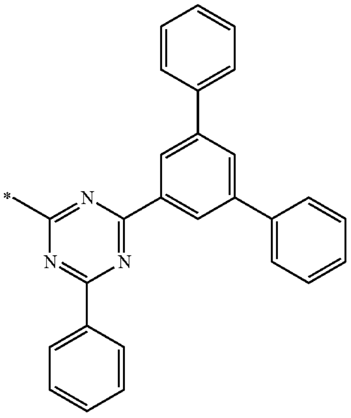,

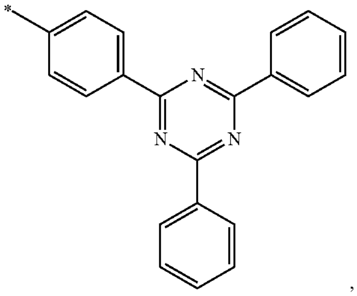,

-continued

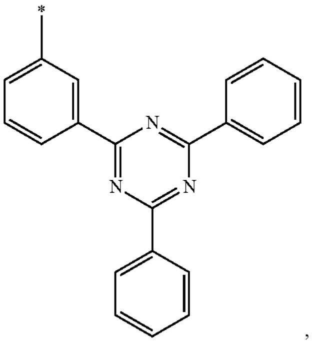,

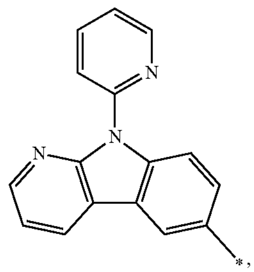,
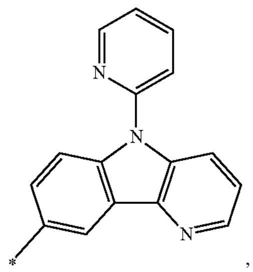,

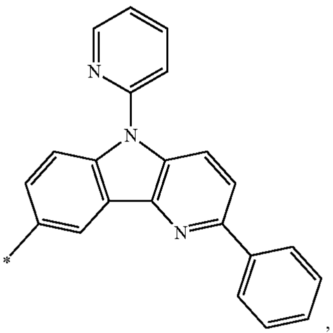,

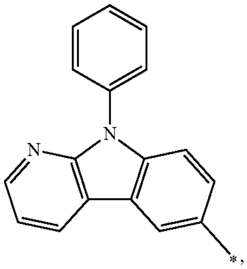, and
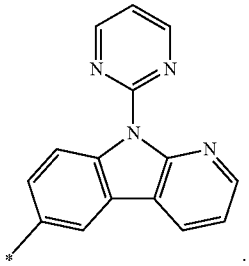.

More preferably, at least one of $Z^1$, $Z^2$, $Z^3$, $Z^6$, $Z^7$, and $Z^8$ in Formula (I) may be a substituted triazine group with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

Preferably, $Z^9$ and $Z^{10}$ in Formula (I) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

In accordance with the present invention, $Z^1$ and $Z^8$ may be the same or different. In accordance with the present invention, $Z^2$ and $Z^7$ may be the same or different. In accordance with the present invention, $Z^3$ and $Z^6$ may be the same or different. In one embodiment, any two of $Z^1$, $Z^2$, $Z^3$, $Z^6$, $Z^7$, and $Z^8$ may be the same substitution as stated above, and the others of $Z^1$, $Z^2$, $Z^3$, $Z^6$, $Z^7$, and $Z^8$ may each independently be a hydrogen atom, a deuterium atom, a halogen group, a cyano group, a nitro group, an alkyl group having 1 to 12 carbon atoms, an alkenyl group having 2 to 12 carbon atoms, or an alkynyl group having 2 to 12 carbon atoms.

For example, $Z^1$, $Z^4$ to $Z^8$ are each independently a hydrogen atom or a deuterium atom, and $Z^2$ and/or $Z^3$ may be the specific aromatic substitution. Or, $Z^1$, $Z^2$, $Z^4$, $Z^5$, $Z^7$, and $Z^8$ are each independently a hydrogen atom or a deuterium atom, and $Z^3$ and $Z^6$ are both the above specific aromatic substitutions.

For example, the compound may be selected from the group consisting of:

Compound I

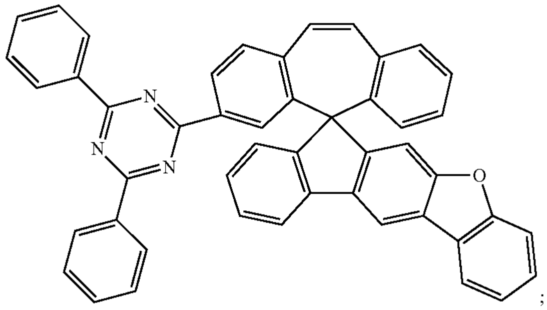

;

Compound II

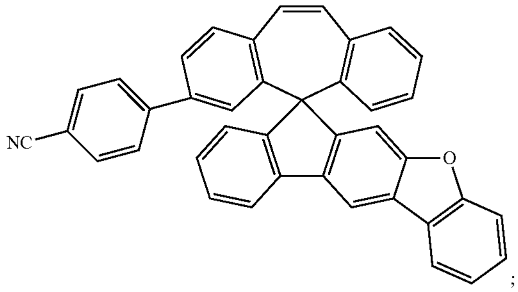

;

Compound III

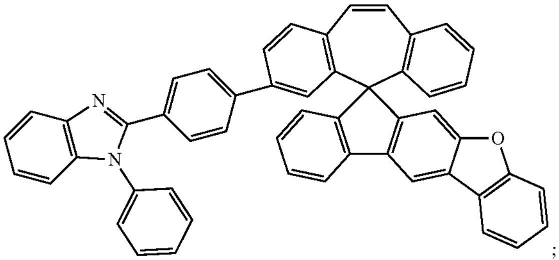

;

Compound IV

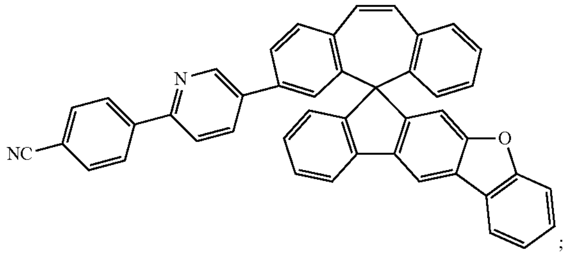

;

-continued

Compound V

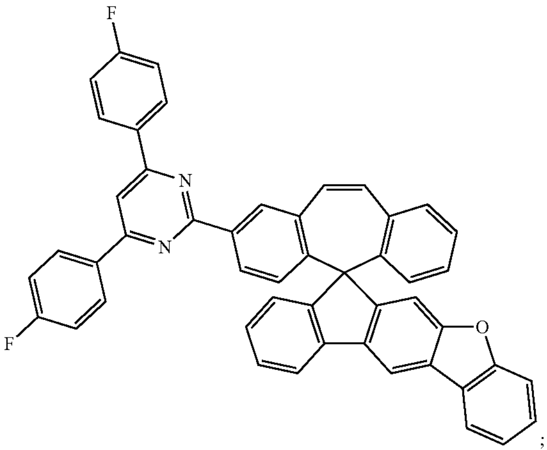

;

Compound VI

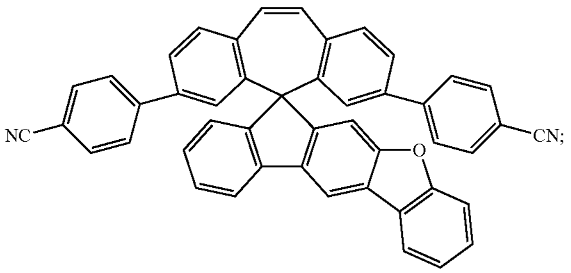

Compound VII

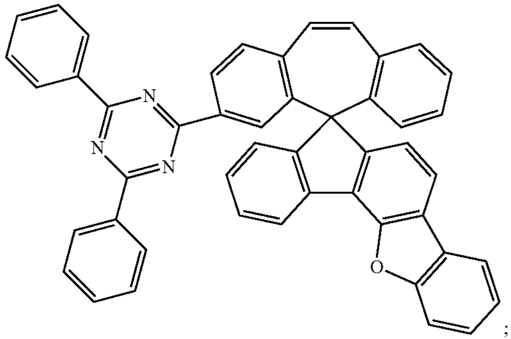

;

Compound VIII

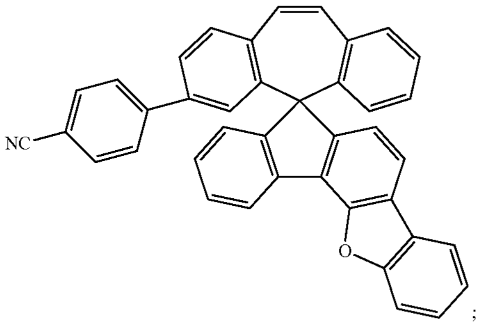

;

-continued
Compound IX
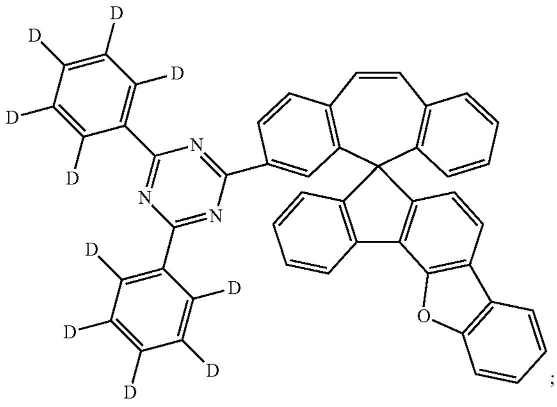
;
Compound X
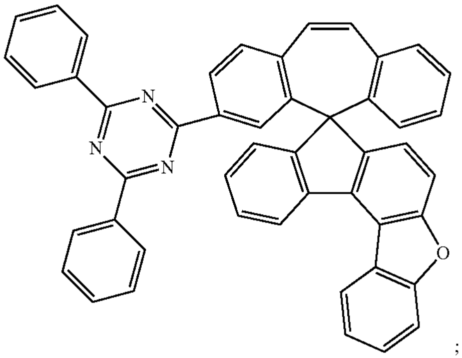
;
Compound XI
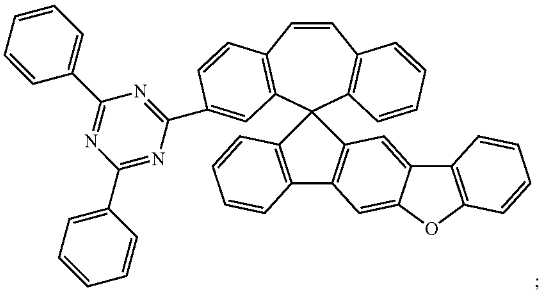
;
Compound XII
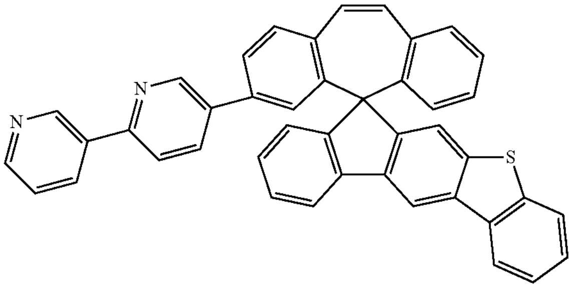
;
-continued
Compound XIII
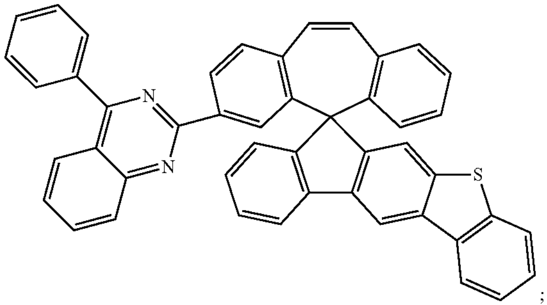
;
Compound XIV
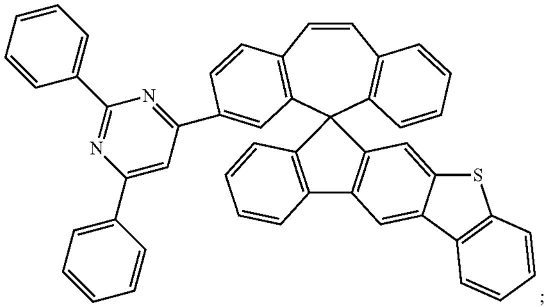
;
Compound XV
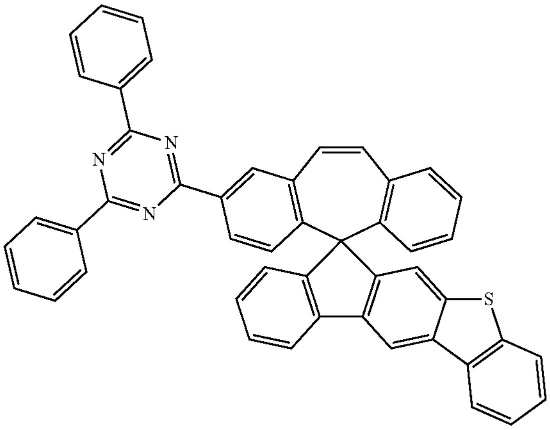
;
Compound XVI
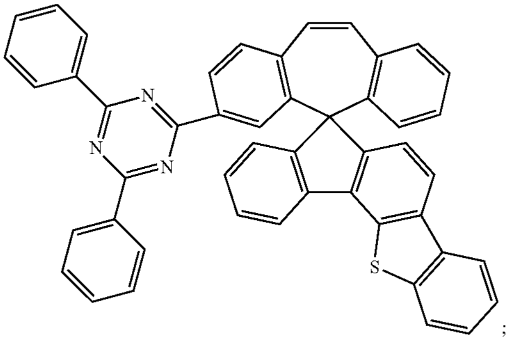
;

-continued
Compound XVII
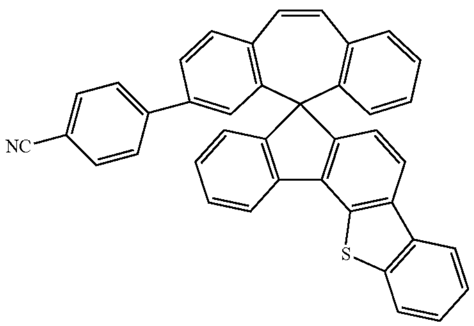
;
Compound XVIII
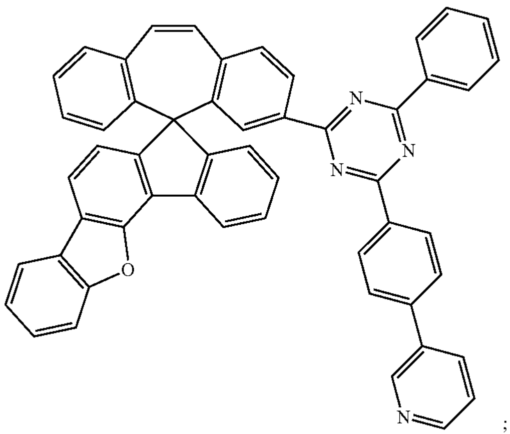
;
Compound XIX
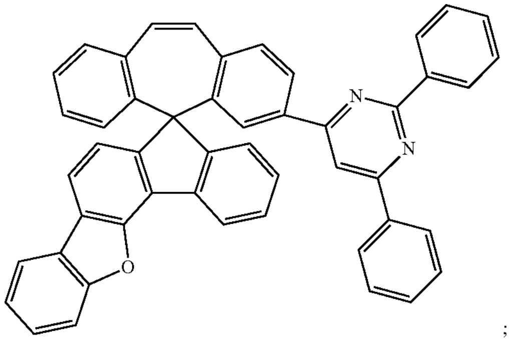
;
Compound XX
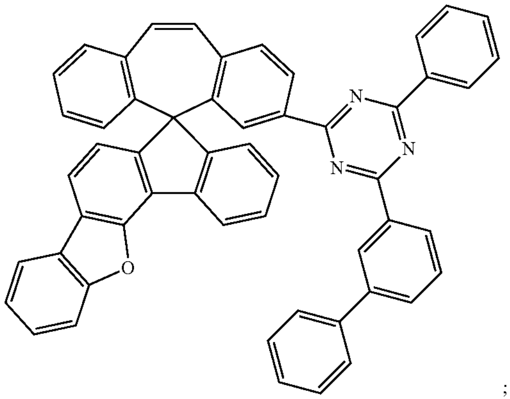
;
-continued
Compound XXI
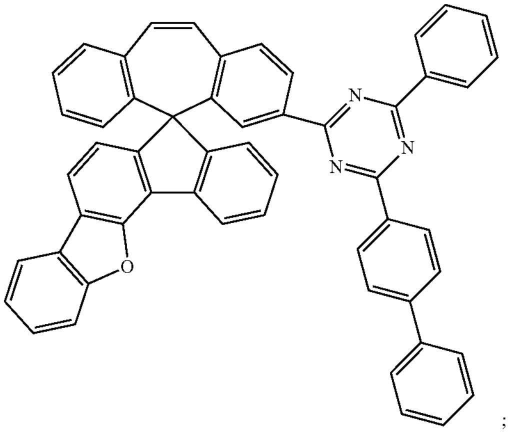
;
Compound XXII
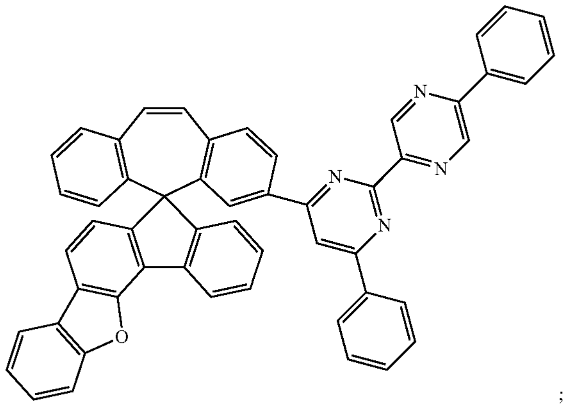
;
Compound XXII
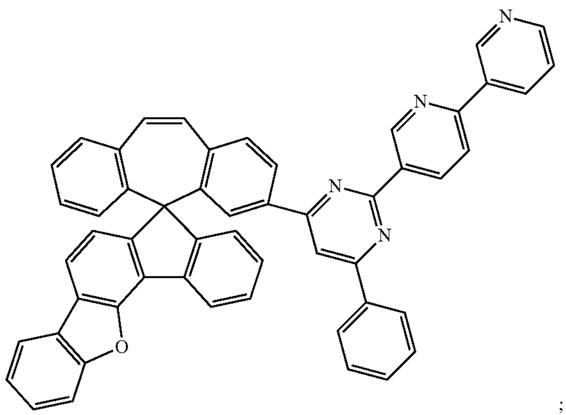
;

-continued
Compound XXIV
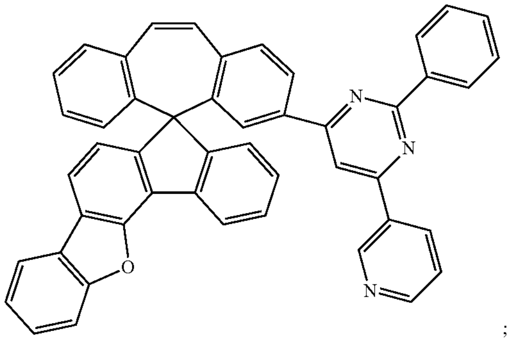
;
Compound XXV
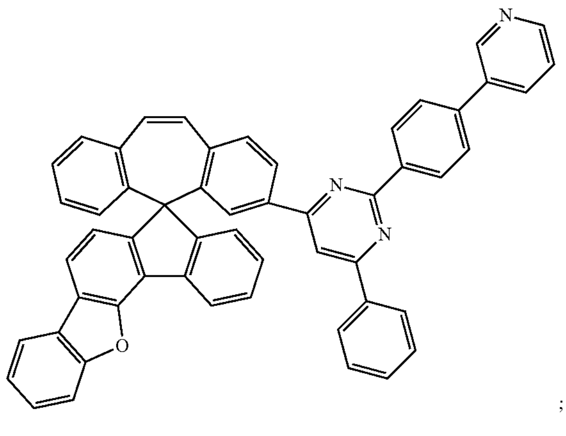
;
Compound XXVI
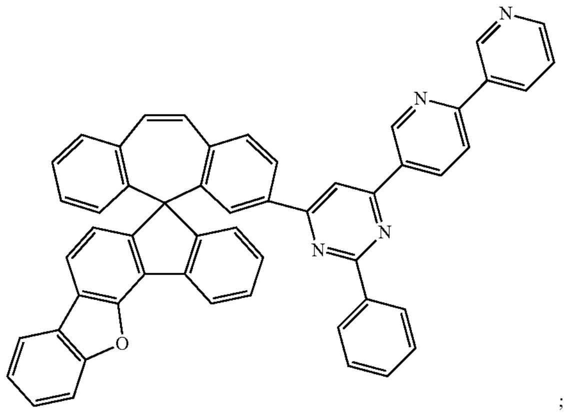
;
Compound XXVII
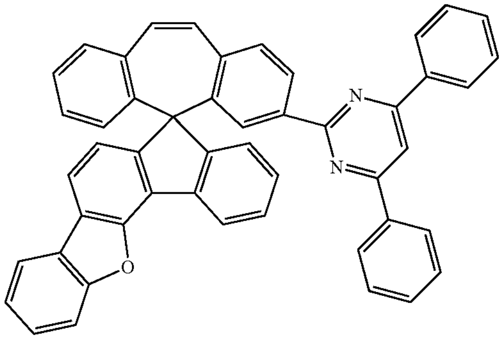
;
-continued
Compound XXVIII
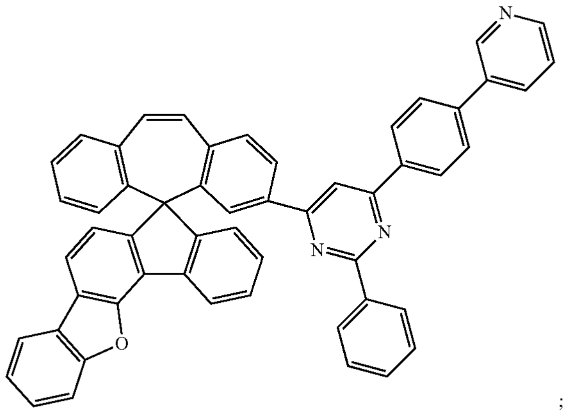
;
Compound XXIX
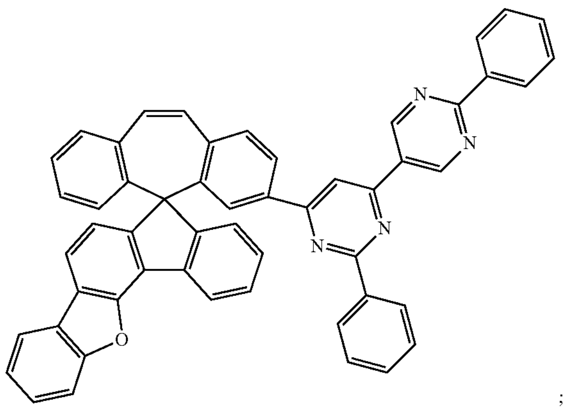
;
Compound XXX
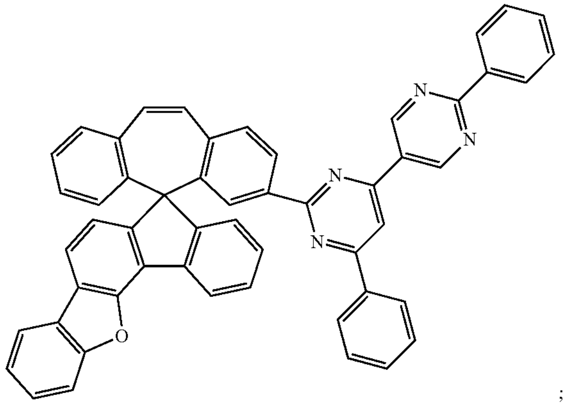
;

-continued
Compound XXXI
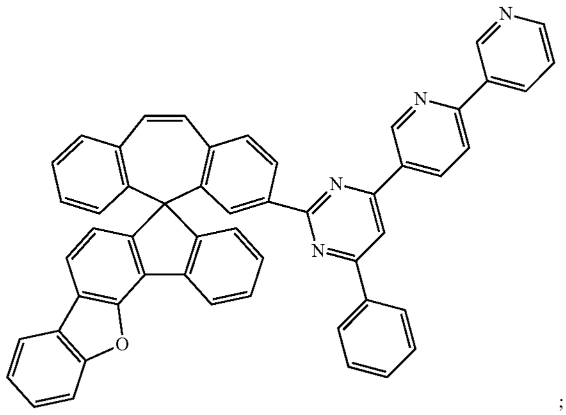
;
Compound XXXII
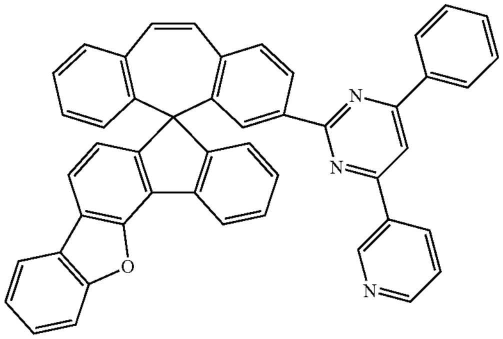
;
Compound XXXIII
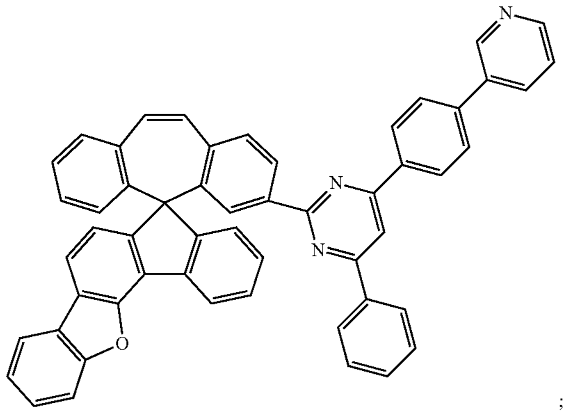
;
Compound XXXIV
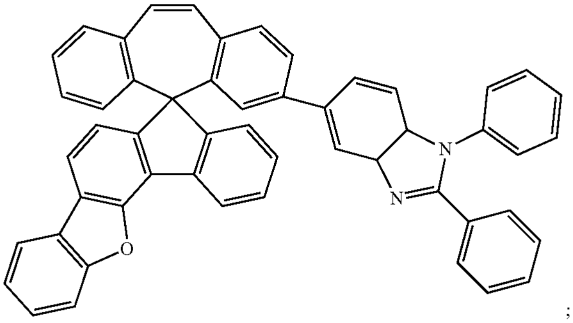
;
-continued
Compound XXXV
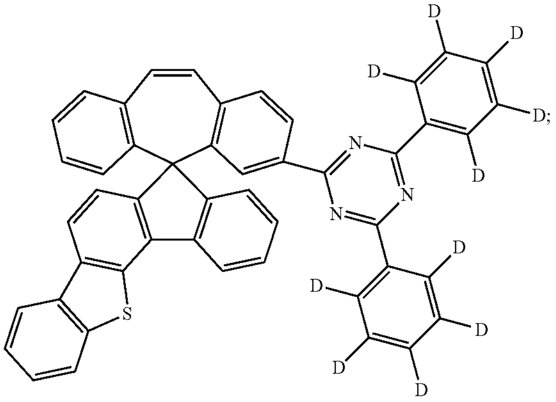
;
Compound XXXVI
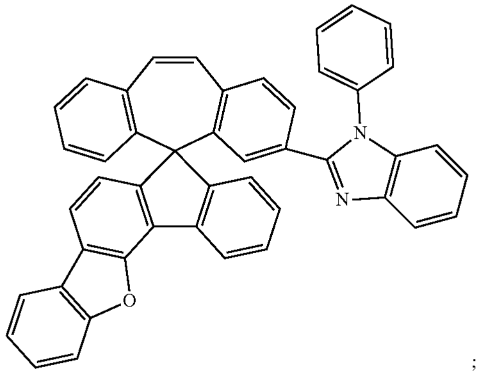
;
Compound XXXVII
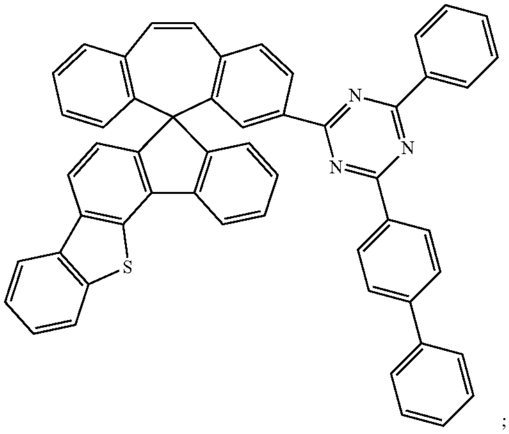
;

-continued
Compound XXXVIII
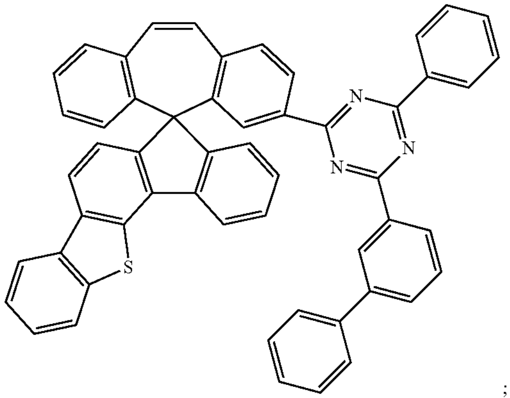
;
Compound XXXIX
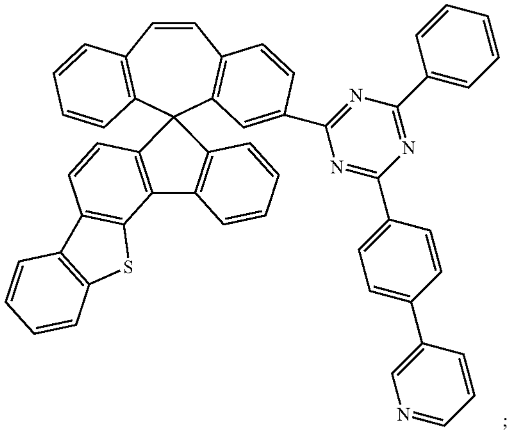
;
Compound XL
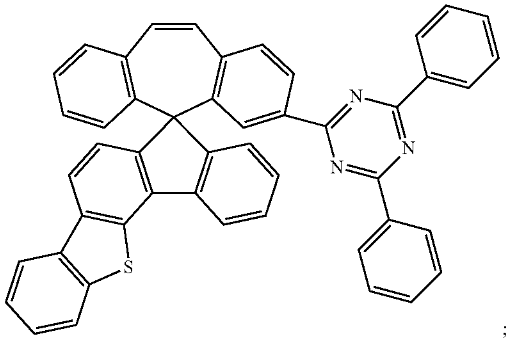
;
Compound XLI
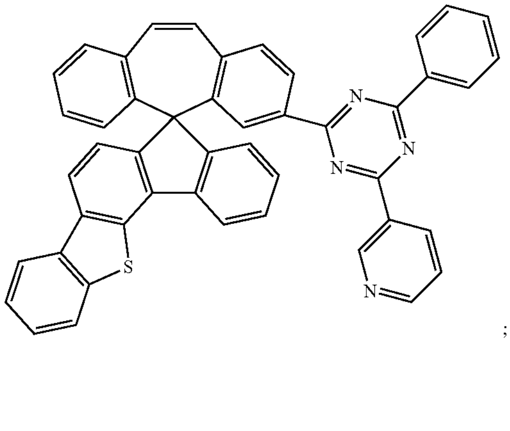
;
-continued
Compound XLII
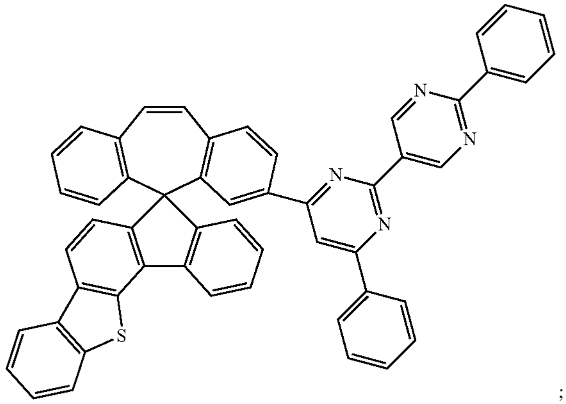
;
Compound XLIII
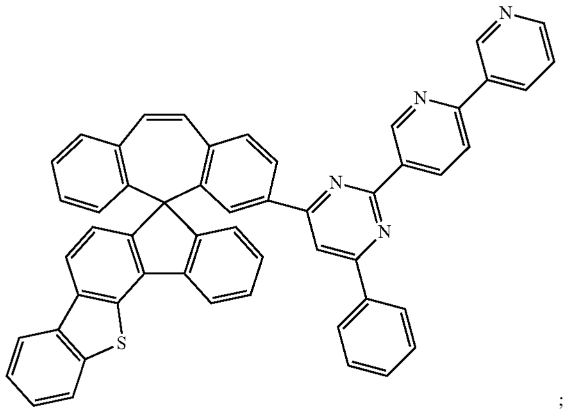
;
Compound XLIV
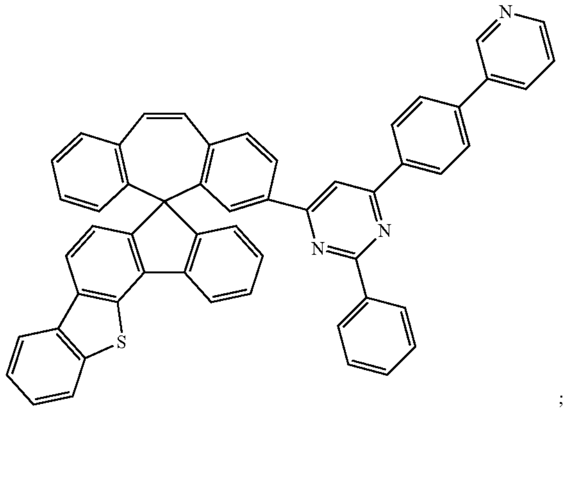
;

-continued
Compound XLV
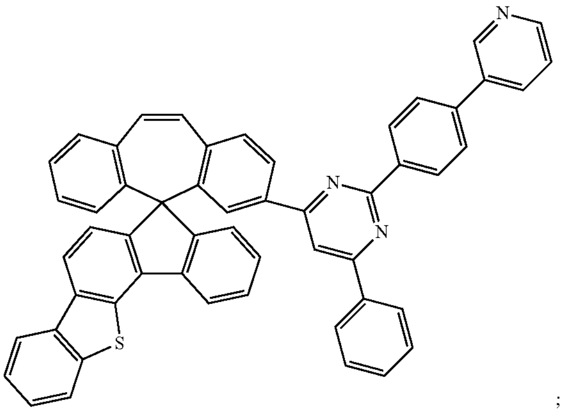
;
Compound XLVI
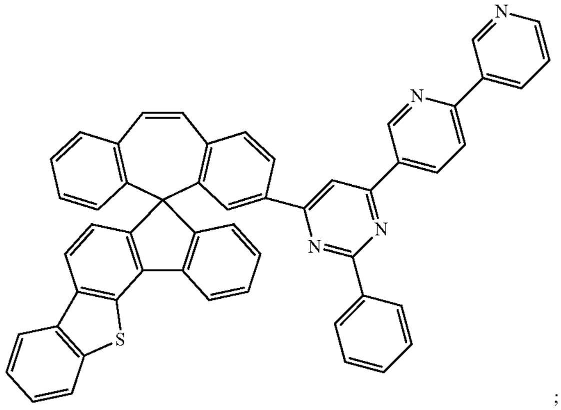
;
Compound XLVII
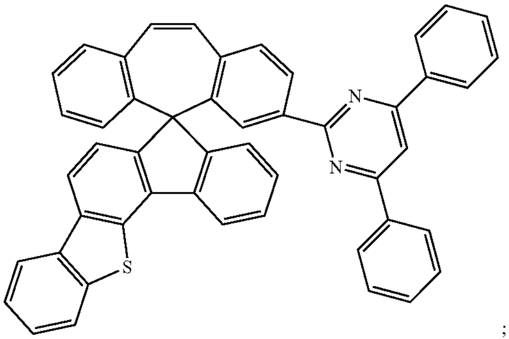
;
Compound XLVIII
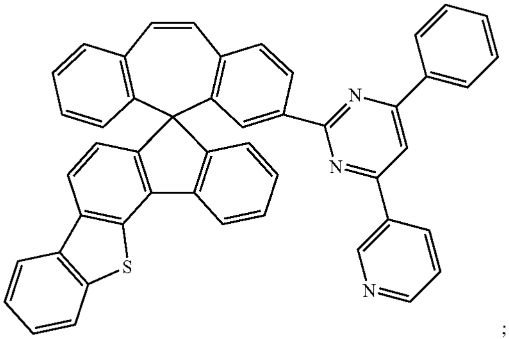
;
-continued
Compound XLIX
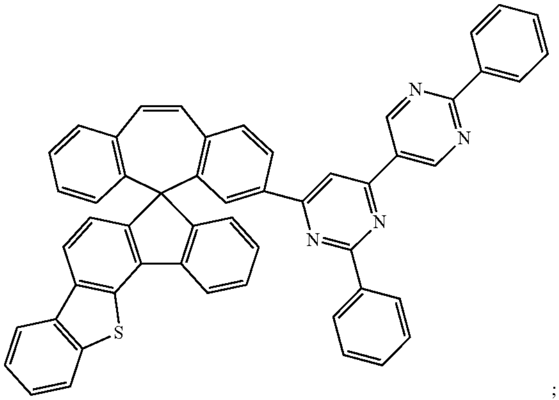
;
Compound L
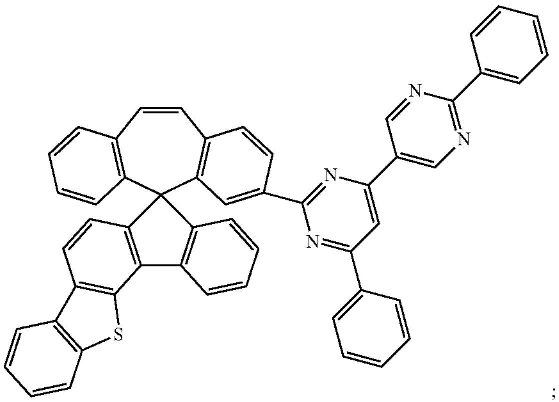
;
Compound LI
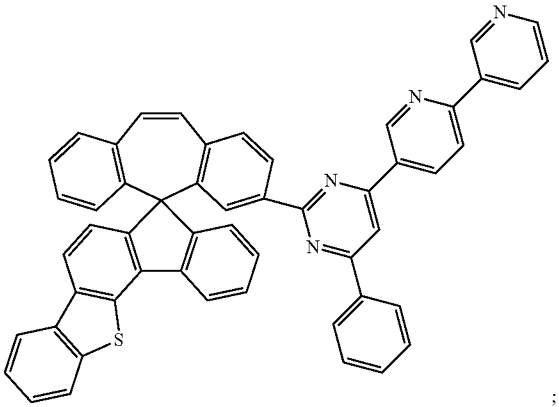
;

-continued
Compound LII
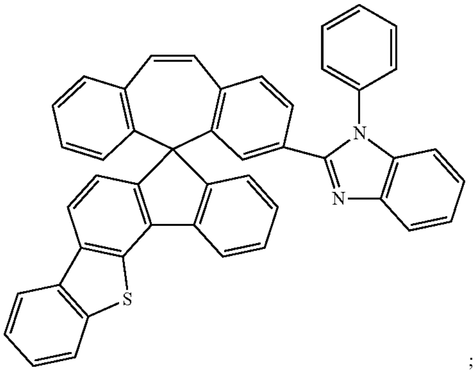
;
Compound LIII
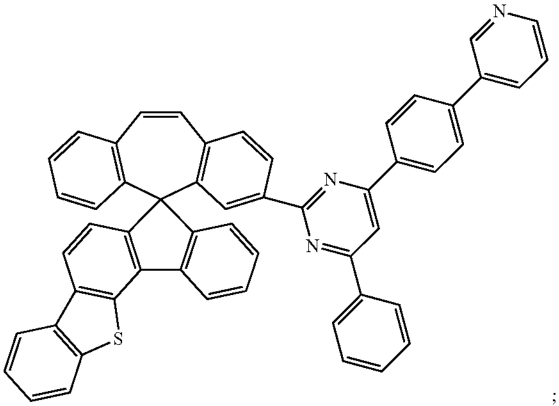
;
Compound LIV
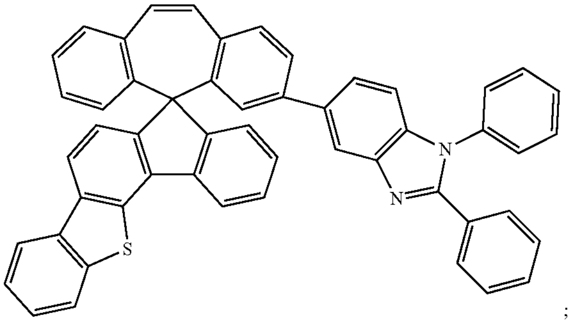
;
Compound LV
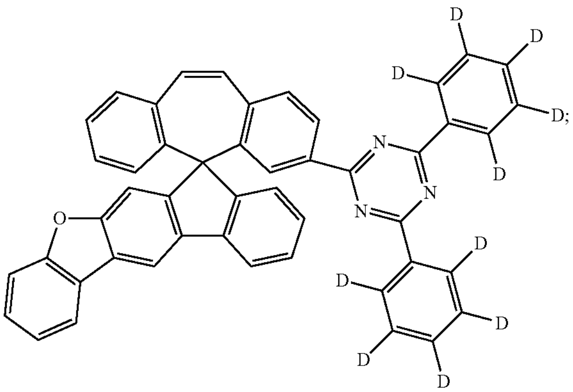
;
-continued
Compound LVI
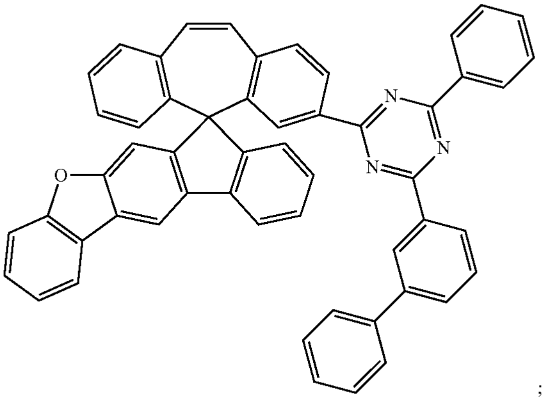
;
Compound LVII
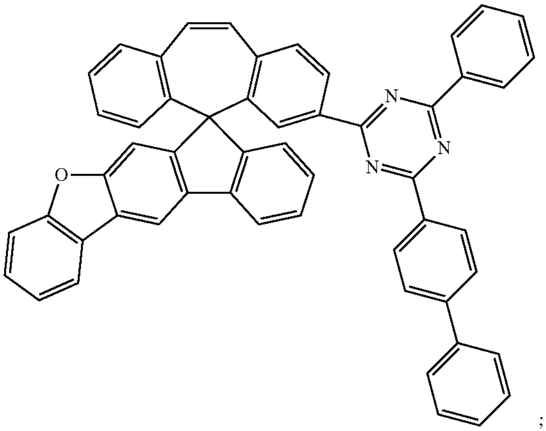
;
Compound LVIII
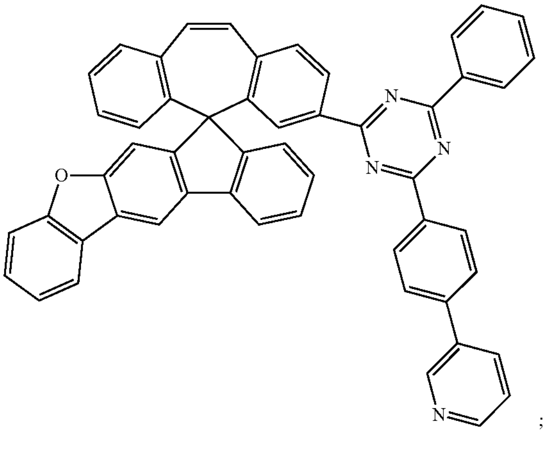
;

-continued
Compound LIX
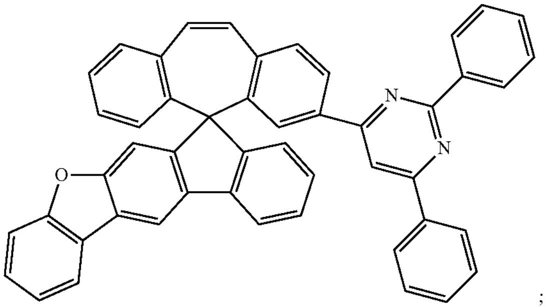
;
Compound LX
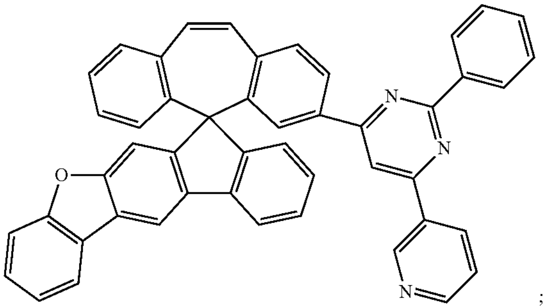
;
Compound LXI
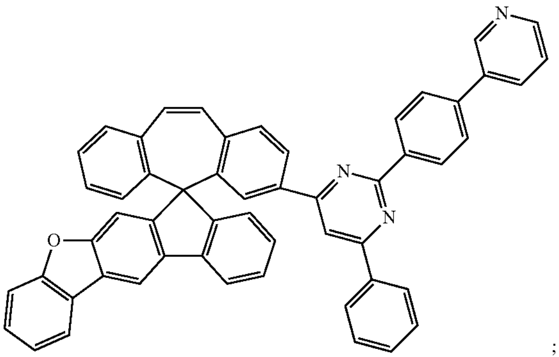
;
Compound LXII
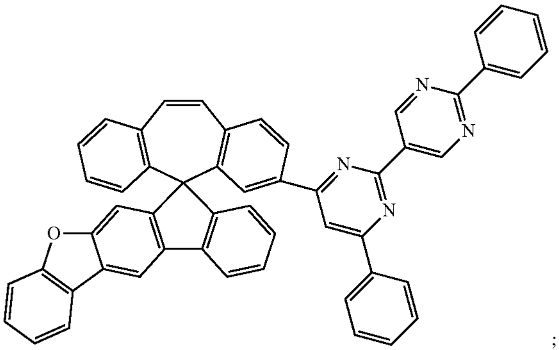
;
-continued
Compound LXIII
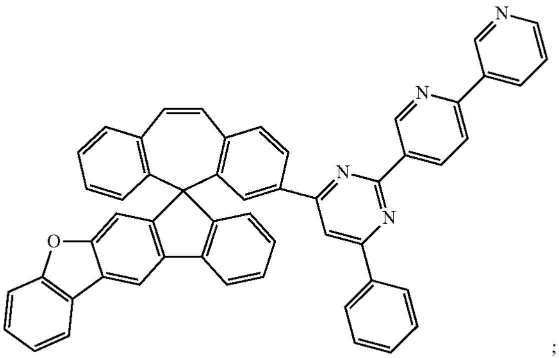
;
Compound LXIV
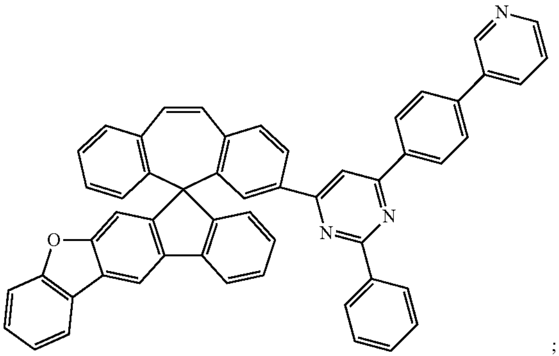
;
Compound LXV
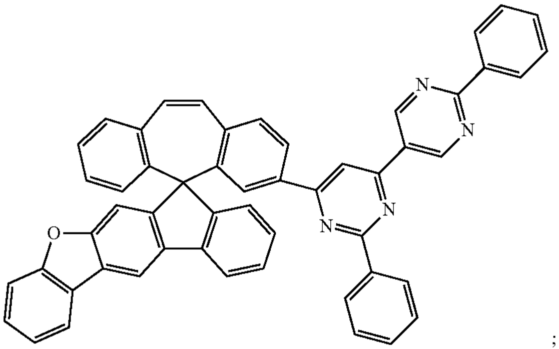
;
Compound LXVI
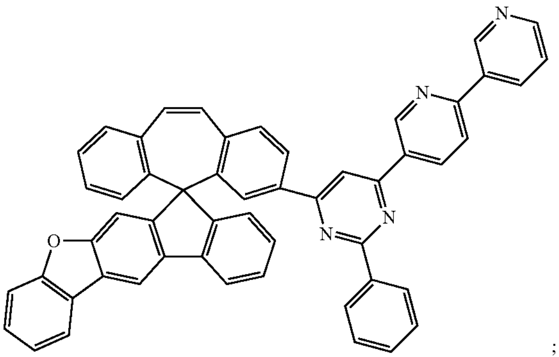
;

-continued
Compound LXVII
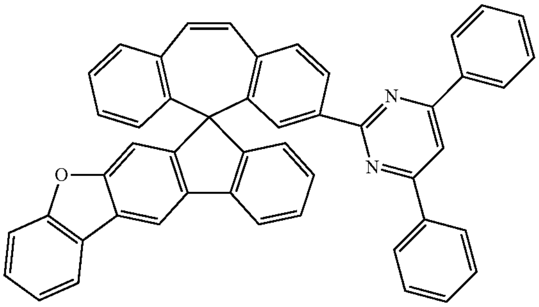
;
Compound LXVIII
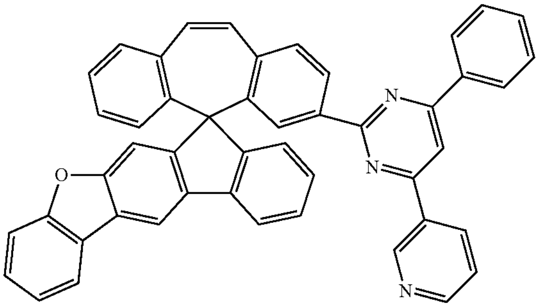
;
Compound LXIX
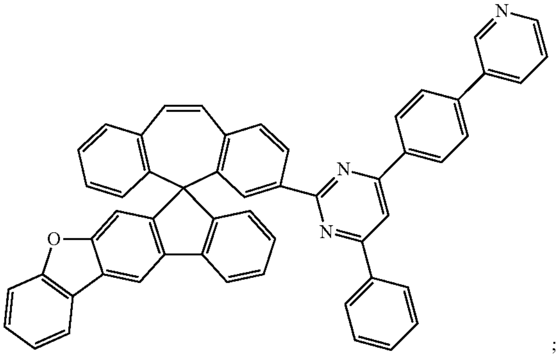
;
Compound LXX
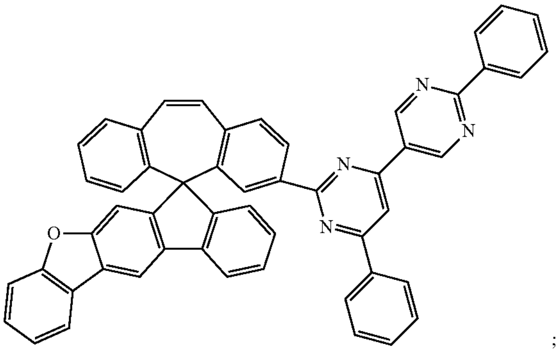
;
-continued
Compound LXXI
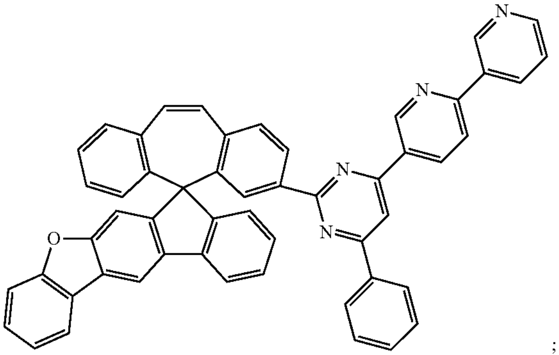
;
Compound LXXII
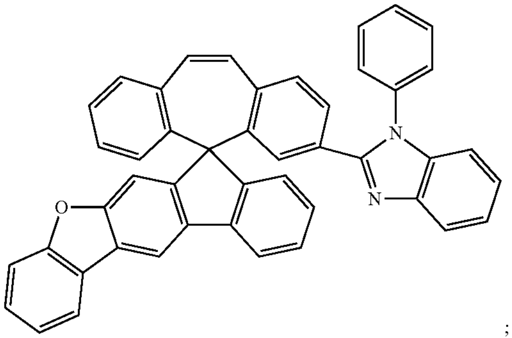
;
Compound LXXIII
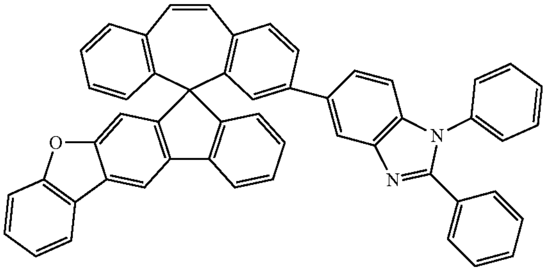
;
Compound LXXIV
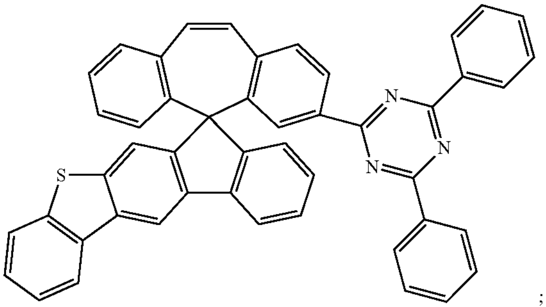
;

-continued
Compound LXXV
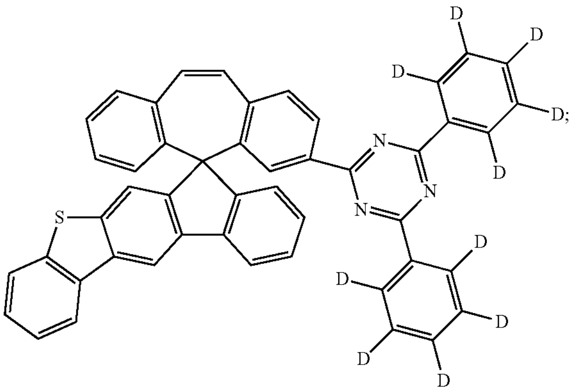
Compound LXXVI
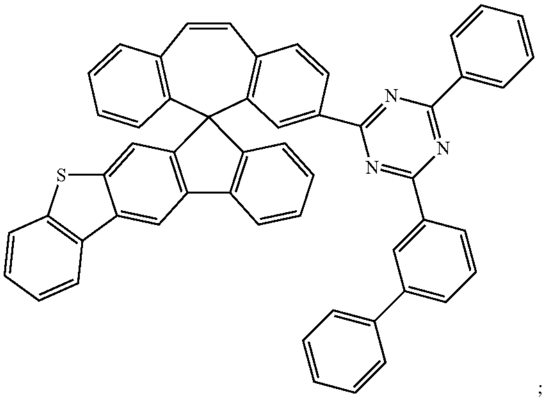
;
Compound LXXVII
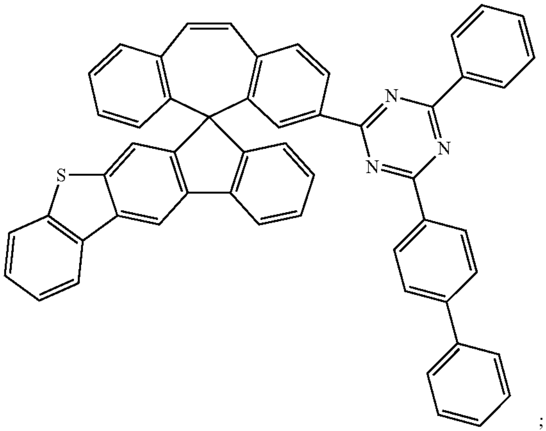
;
-continued
Compound LXXVIII
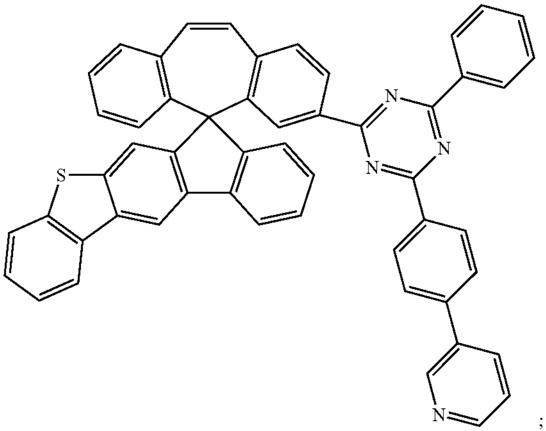
;
Compound LXXIX
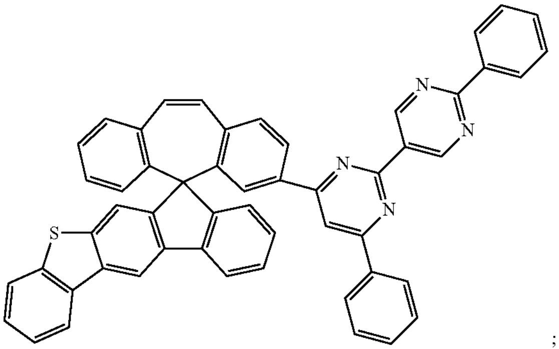
;
Compound LXXX
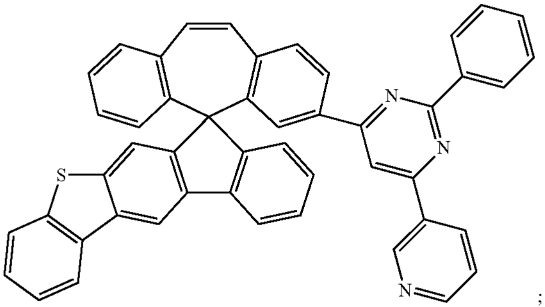
;
Compound LXXXI
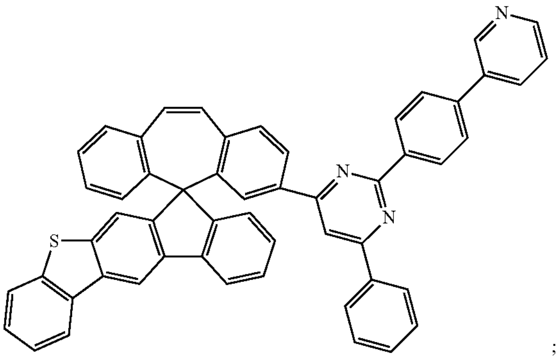
;

-continued
Compound LXXXII
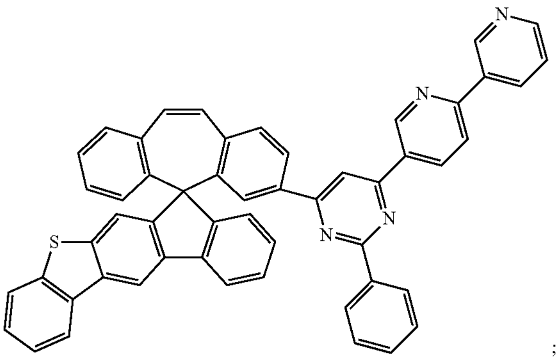
;
Compound LXXXIII
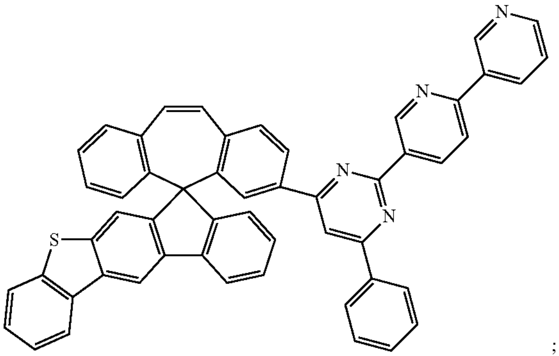
;
Compound LXXXIV
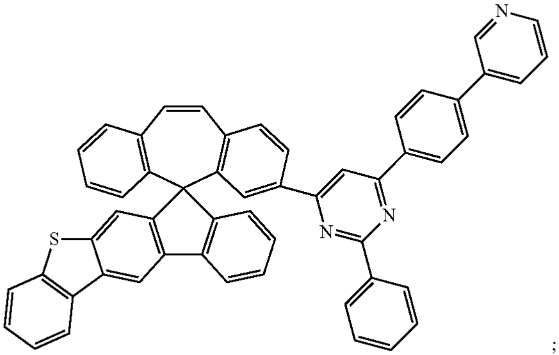
;
Compound LXXXV
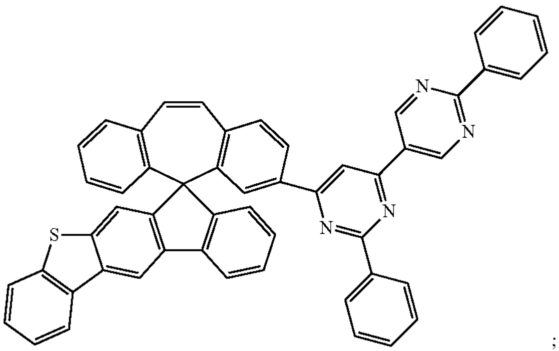
;
-continued
Compound LXXXVI
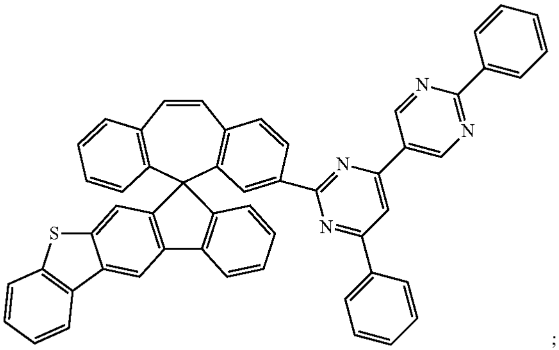
;
Compound LXXXVII
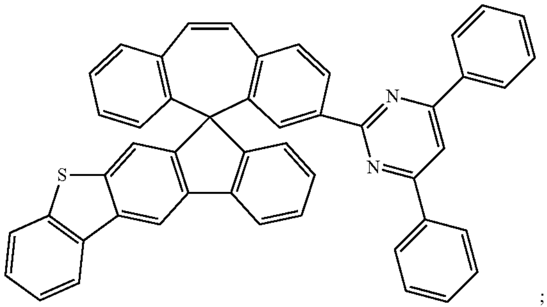
;
Compound LXXXVIII
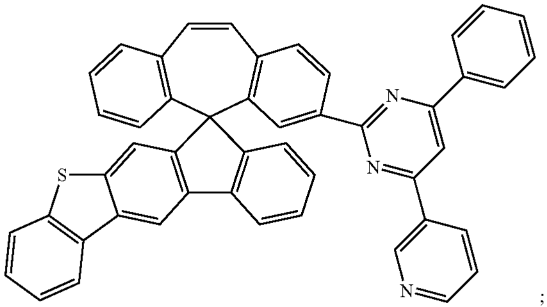
;
Compound LXXXIX
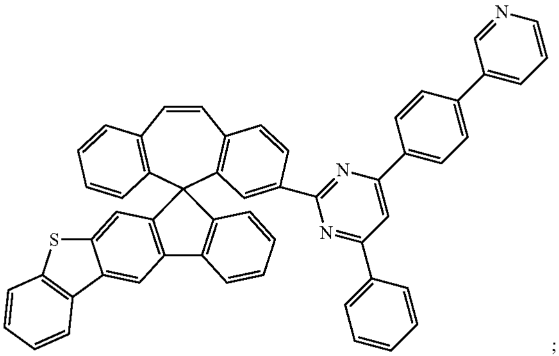
;

-continued
Compound XC
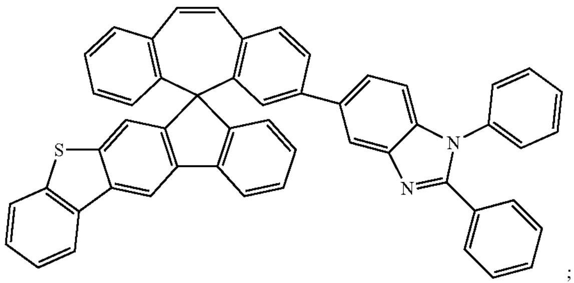
;
Compound XCI
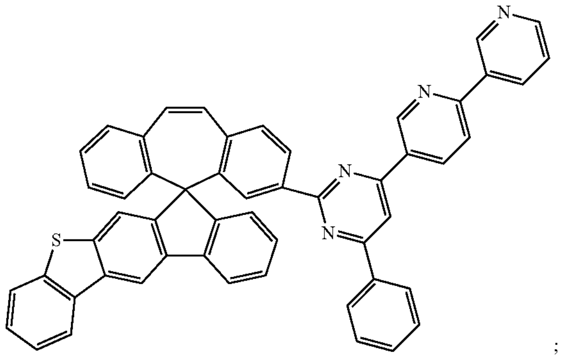
;
Compound XCII
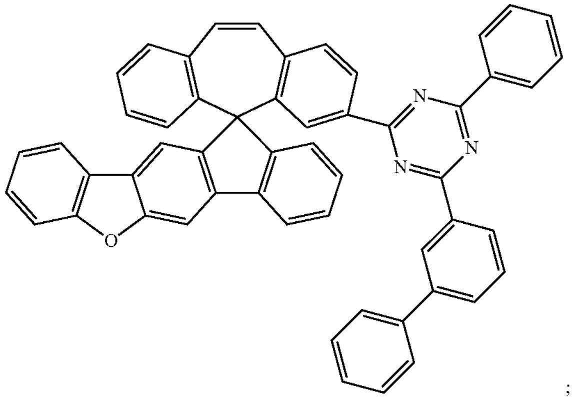
;
Compound XCIII
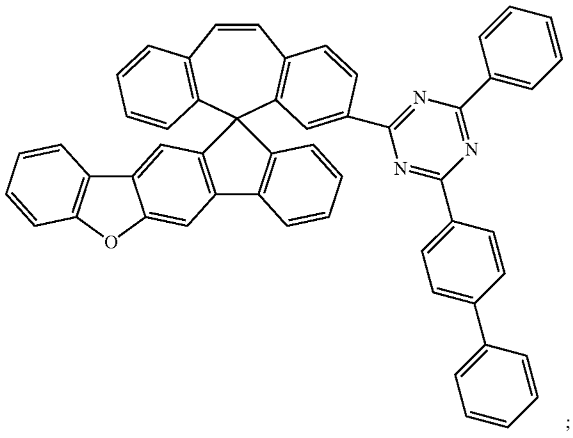
;
-continued
Compound XCIV
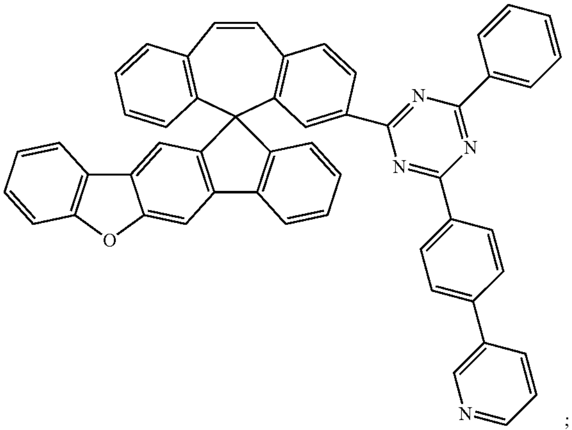
;
Compound XCV
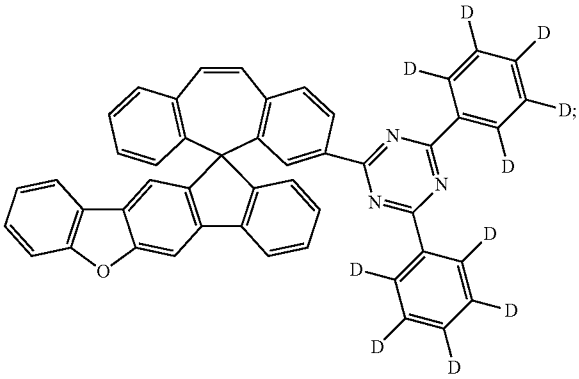
Compound XCVI
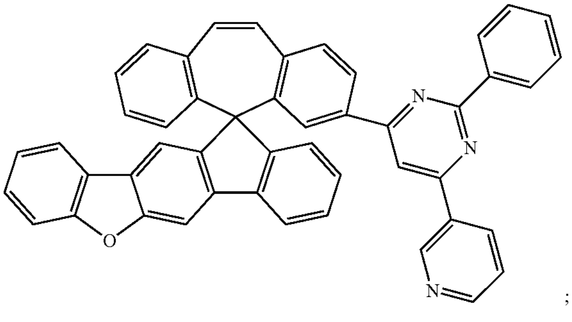
;
Compound XCVII
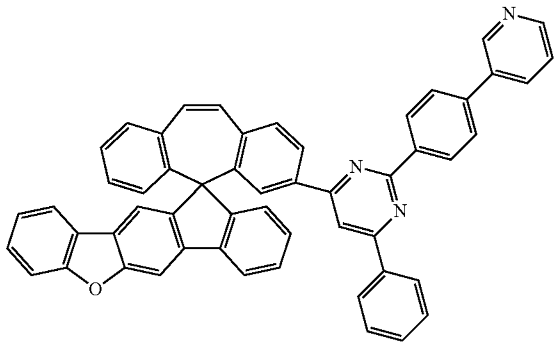
;

Compound XCVIII
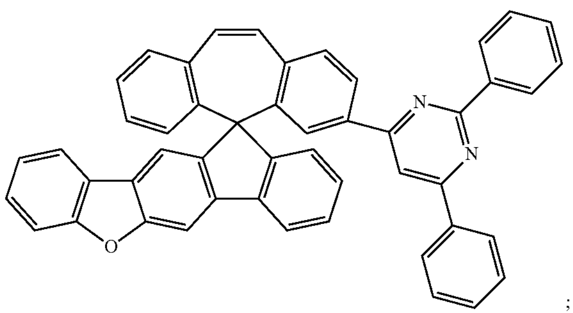
;
Compound XCIX
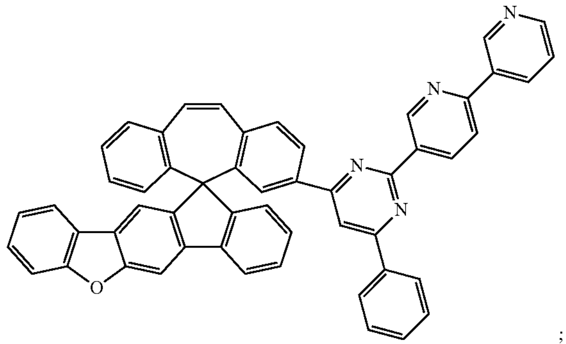
;
Compound C
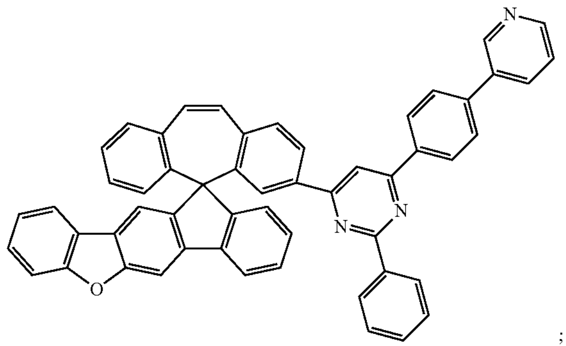
;
Compound CI
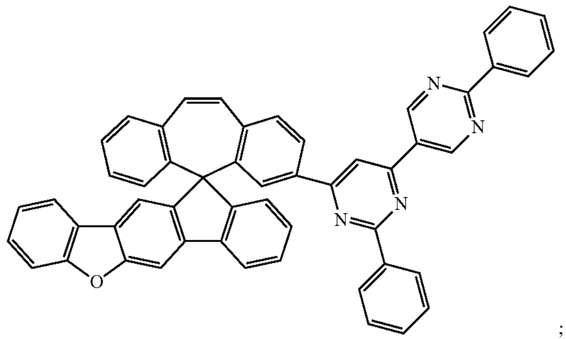
;
Compound CII
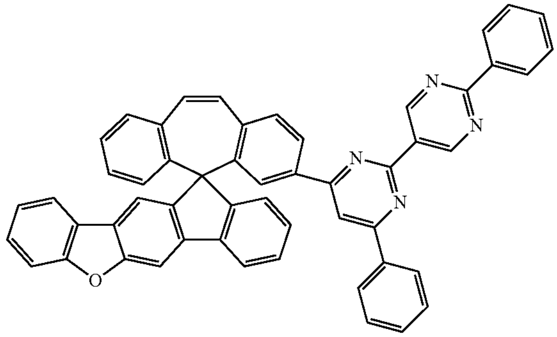
;
Compound CIII
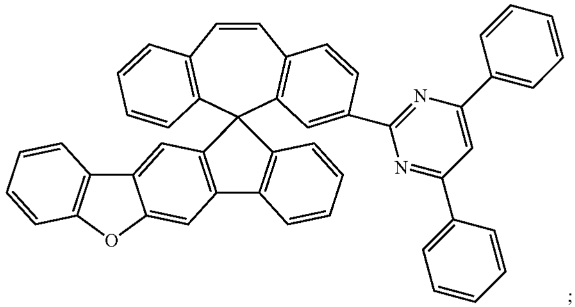
;
Compound CIV
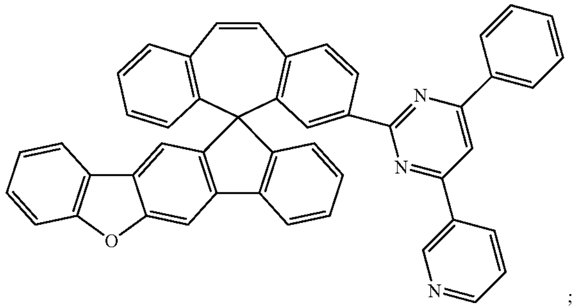
;
Compound CV
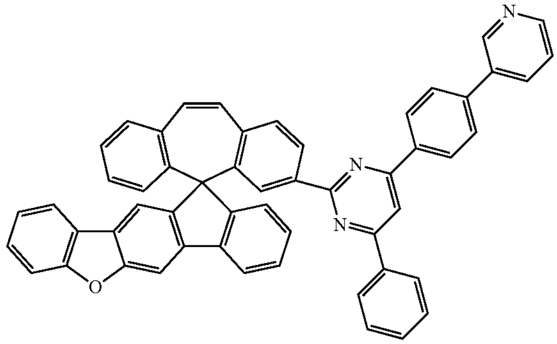
;

Compound CVI
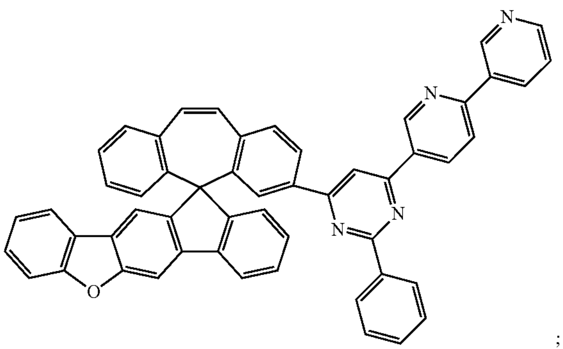
;
Compound CVII
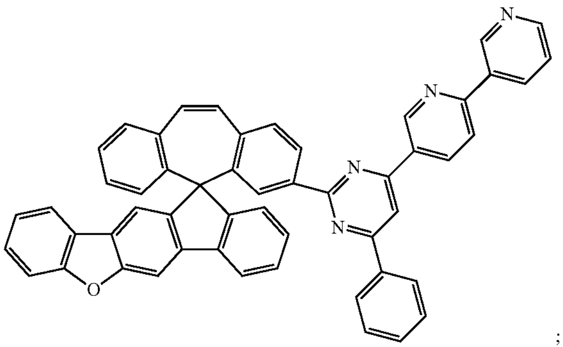
;
Compound CVIII
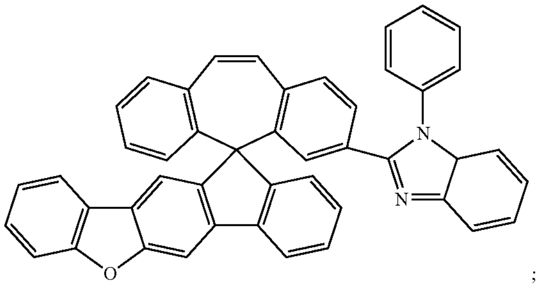
;
Compound CIX
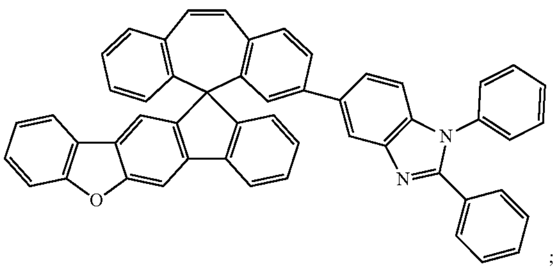
;
Compound CX
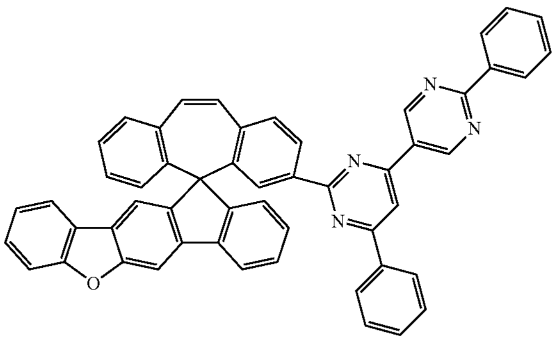
;
Compound CXI
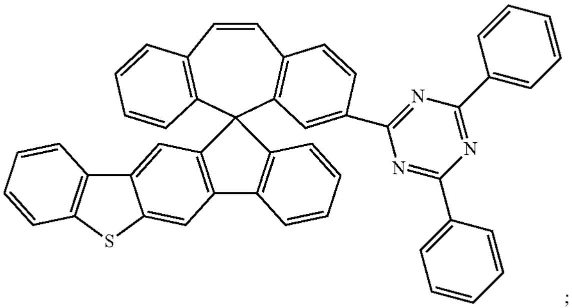
;
Compound CXII
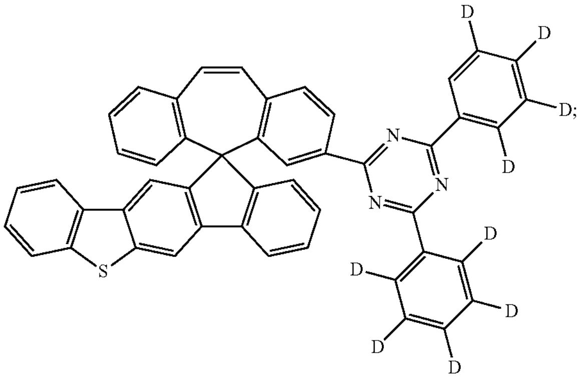
Compound CXIII
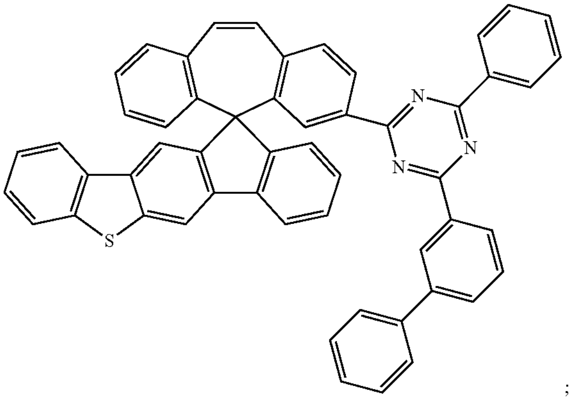
;

-continued
Compound CXIV
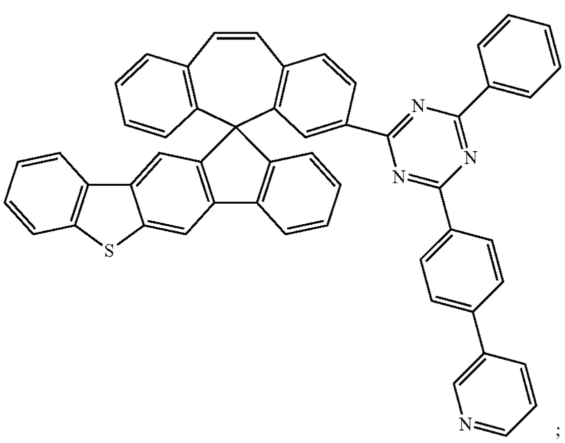
;
Compound CXV
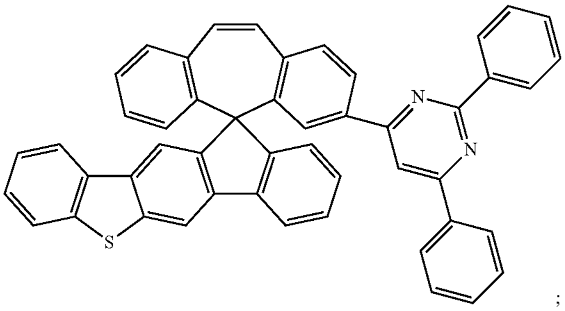
;
Compound CXVI
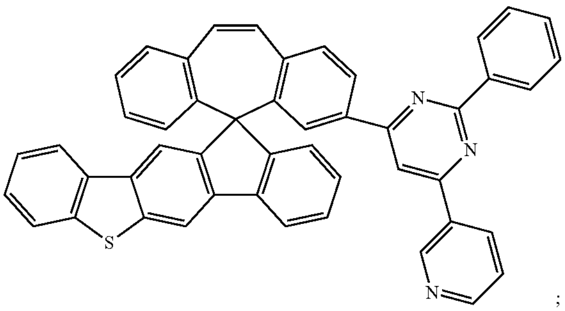
;
Compound CXVII
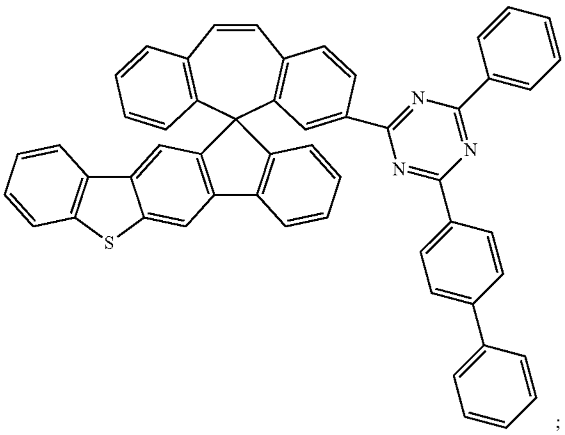
;
-continued
Compound CXVIII
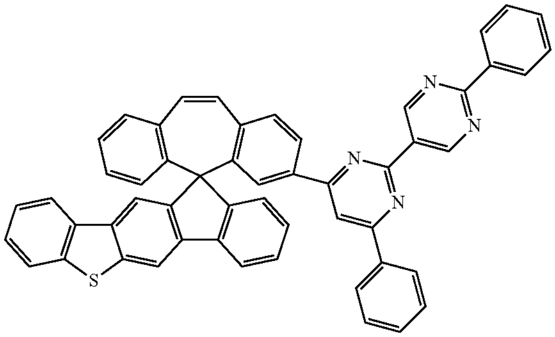
;
Compound CXIX
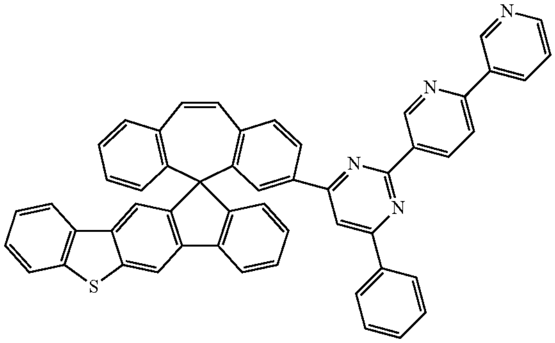
;
Compound CXX
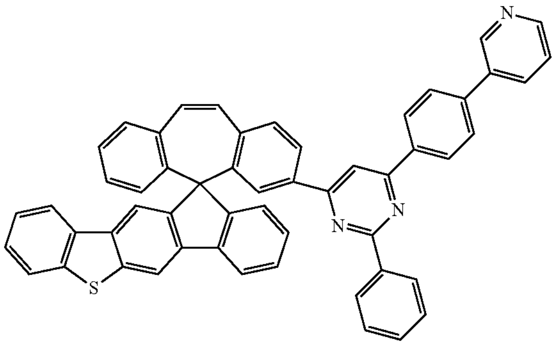
;
Compound CXXI
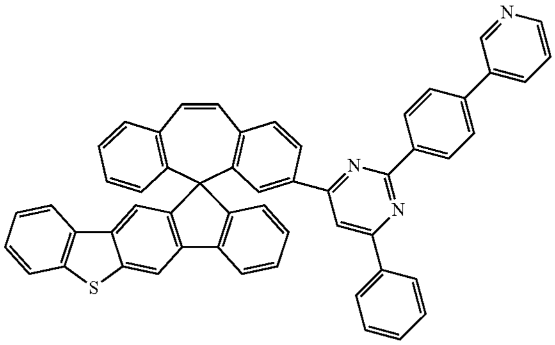
;

-continued
Compound CXXII
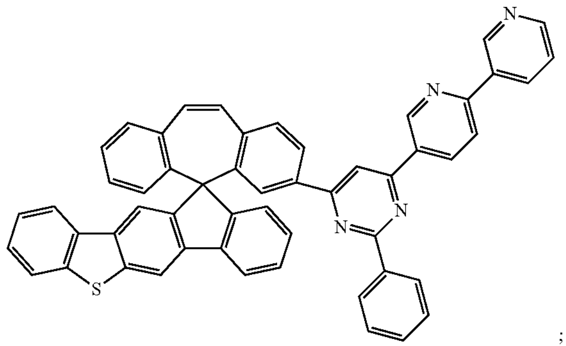
;
Compound CXXIII
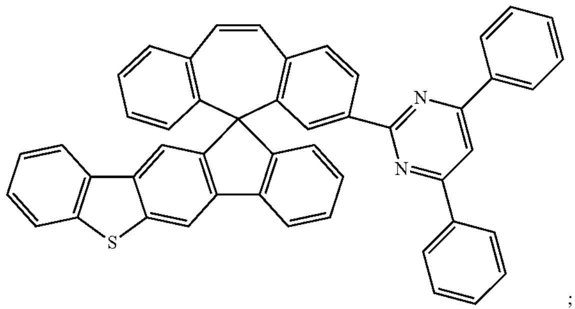
;
Compound CXXIV
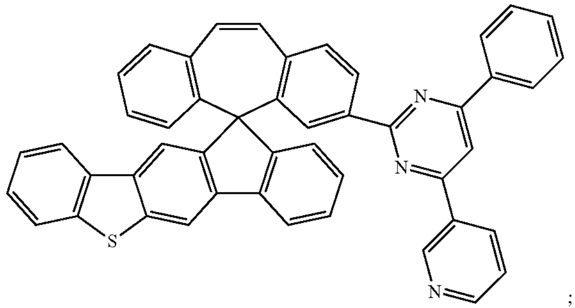
;
Compound CXXV
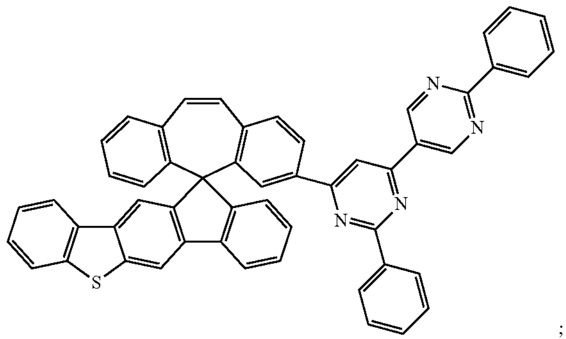
;
-continued
Compound CXXVI
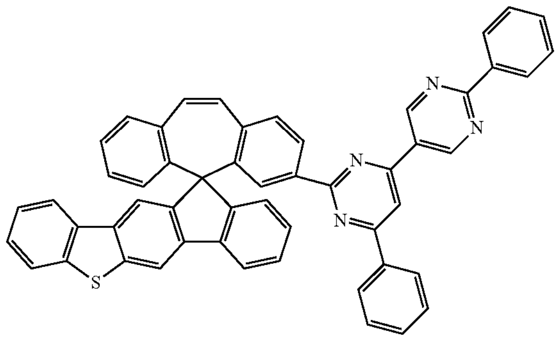
;
Compound CXXVII
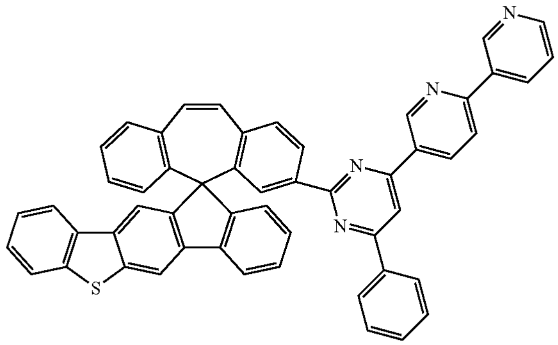
;
Compound CXXVIII
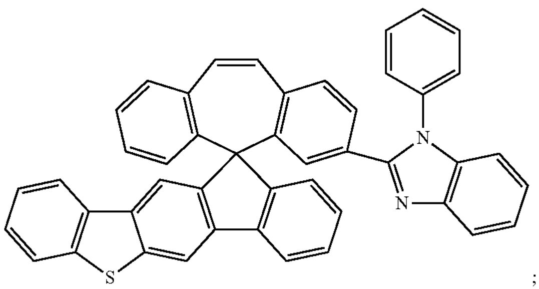
;
Compound CXXIX
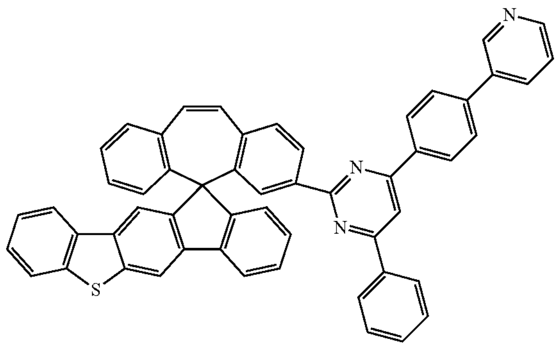
;

-continued
Compound CXXX
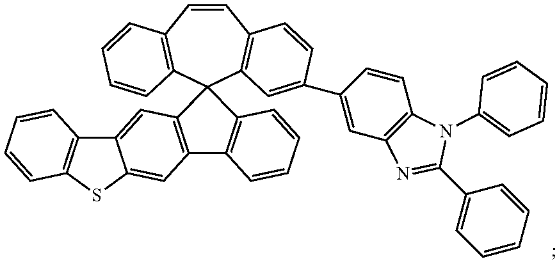
;
Compound CXXXI
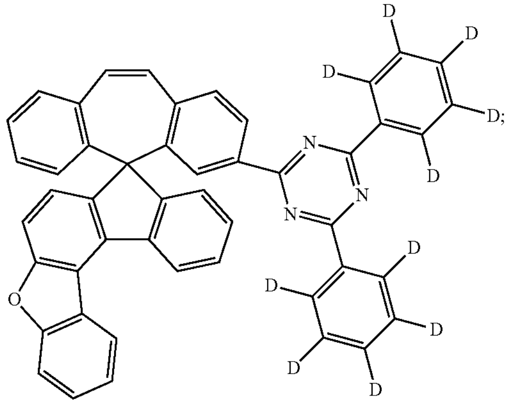
Compound CXXXII
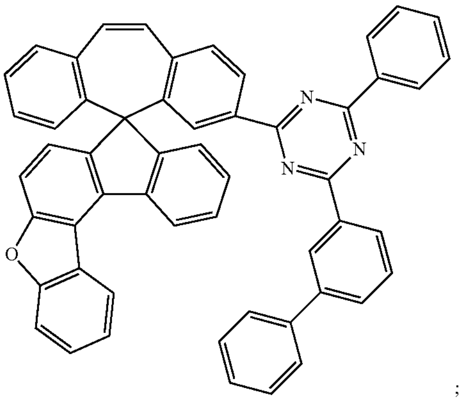
;
Compound CXXXIII
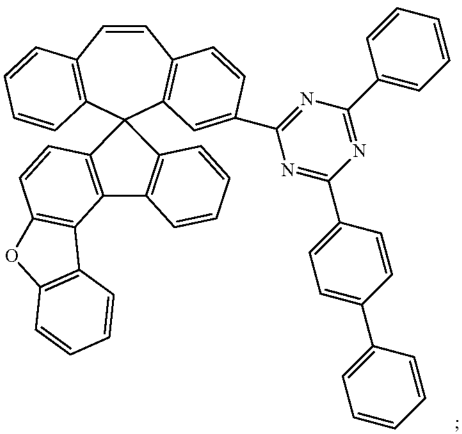
;
-continued
Compound CXXXIV
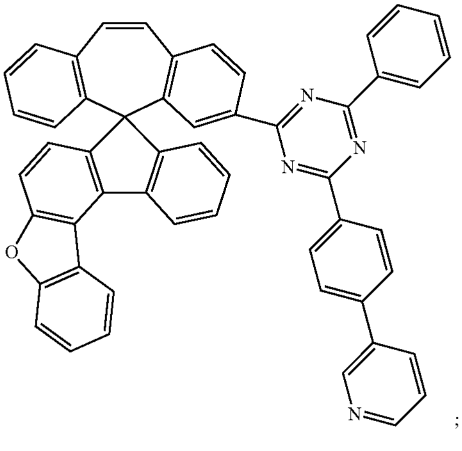
;
Compound CXXXV
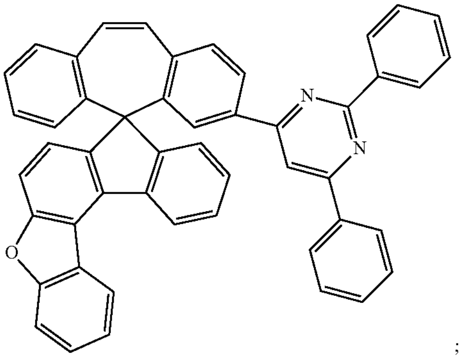
;
Compound CXXXVI
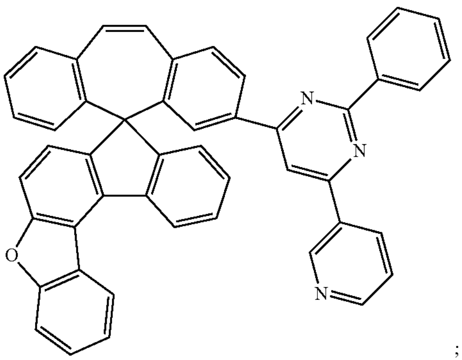
;

-continued
Compound CXXXVII
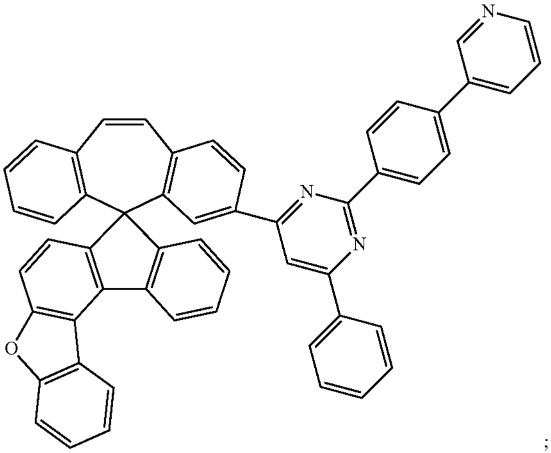
;
Compound CXXXVIII
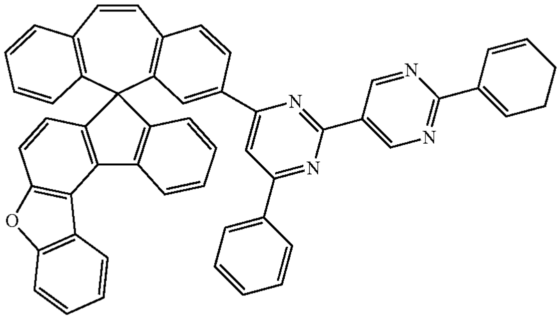
;
Compound CXXXIX
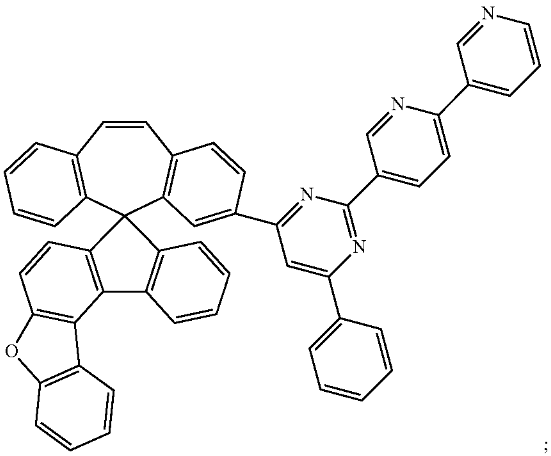
;
-continued
Compound CXL
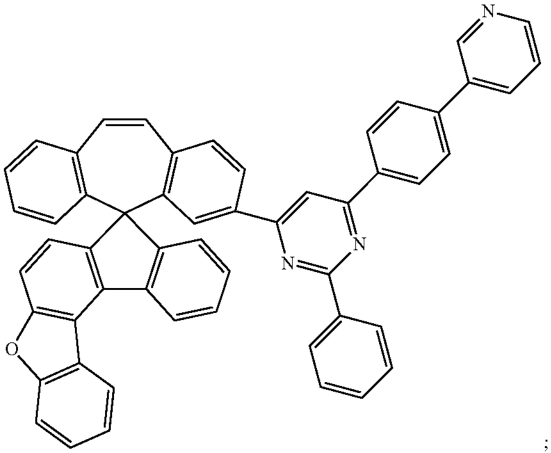
;
Compound CXLI
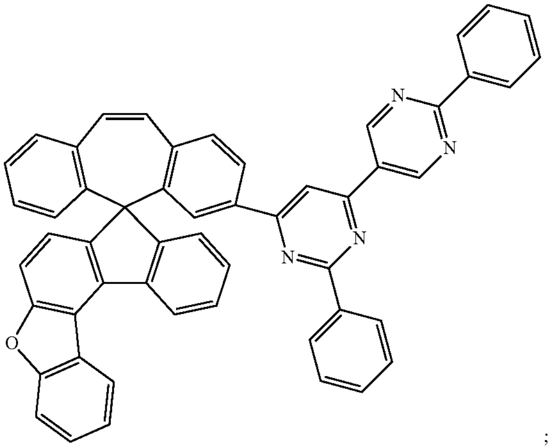
;
Compound CXLII
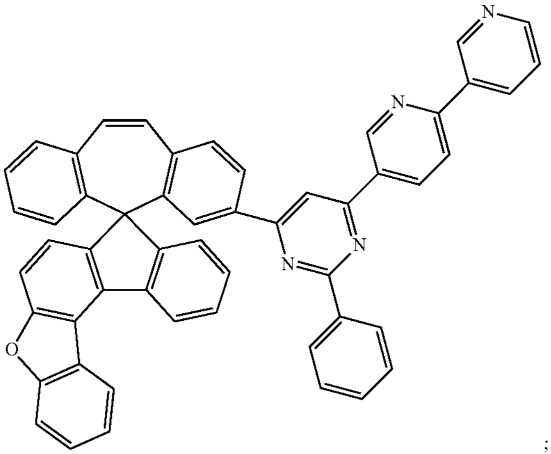
;

-continued
Compound CXLIII
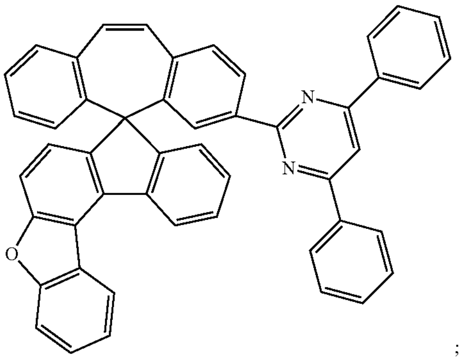
;
Compound CXLIV
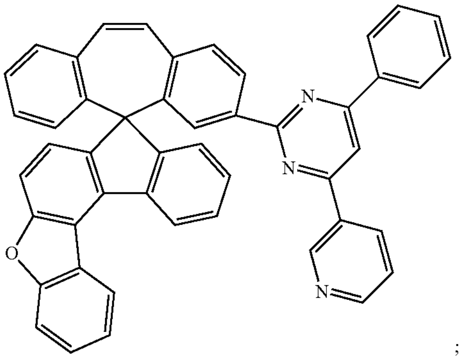
;
Compound CXLV
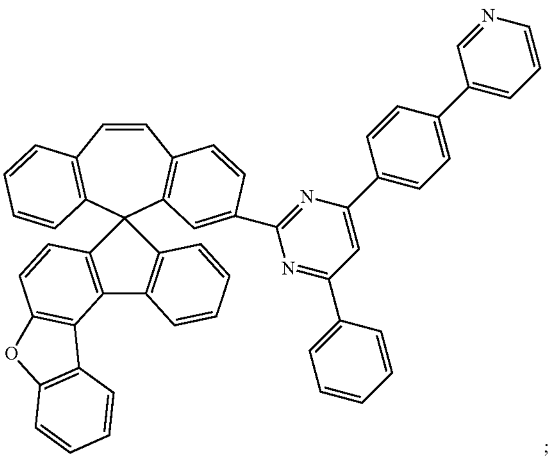
;
-continued
Compound CXLVI
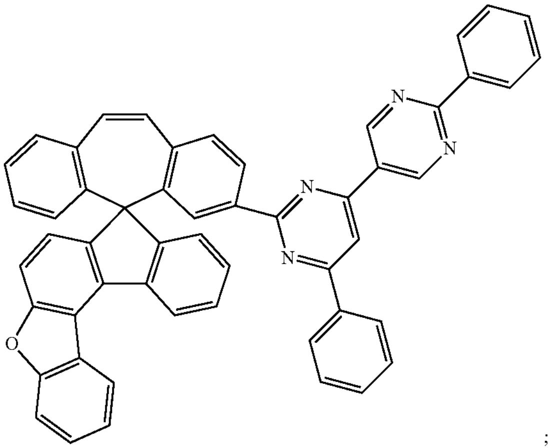
;
Compound CXLVII
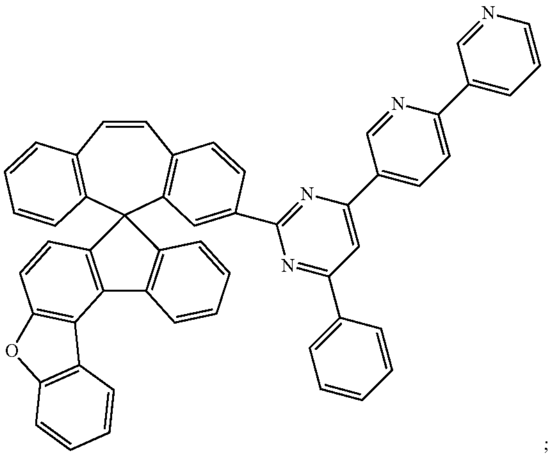
;
Compound CXLVIII
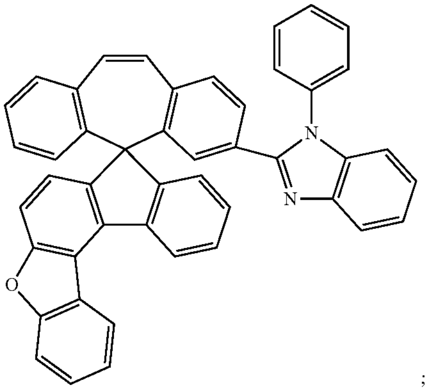
;

-continued
Compound CXLIX
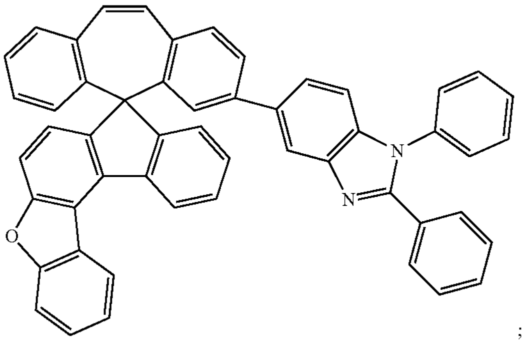
;
Compound CL
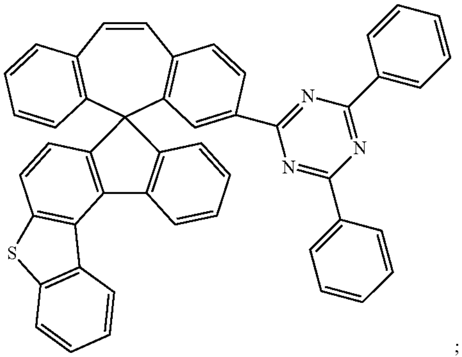
;
Compound CLI
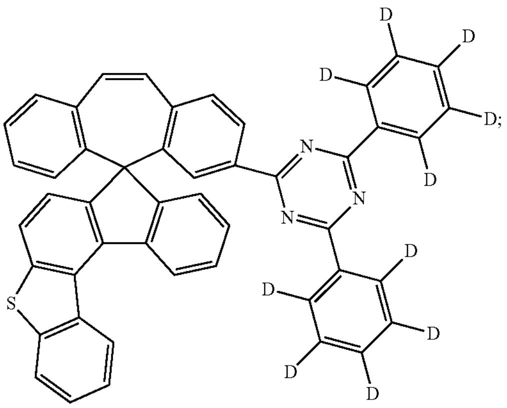
Compound CLII
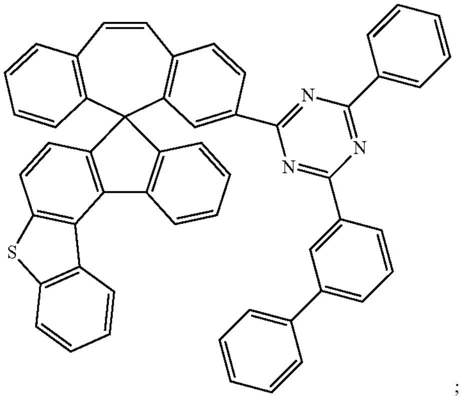
;
-continued
Compound CLIII
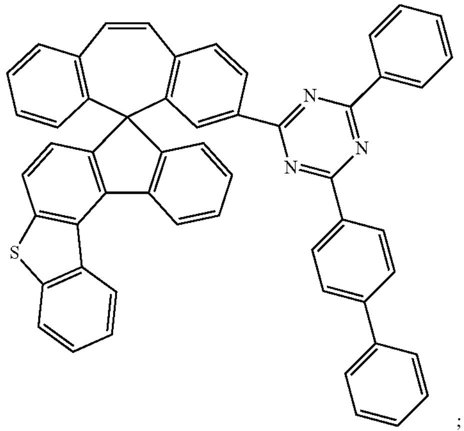
;
Compound CLIV
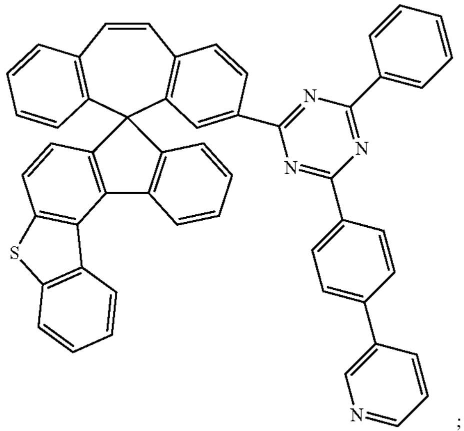
;
Compound CLV
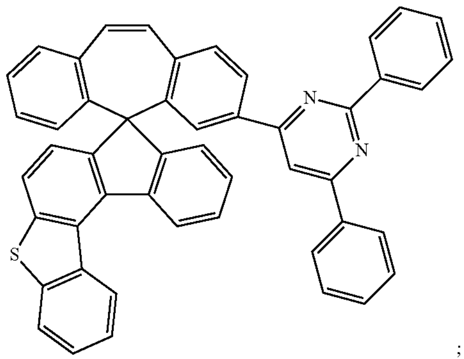
;

-continued
Compound CLVI
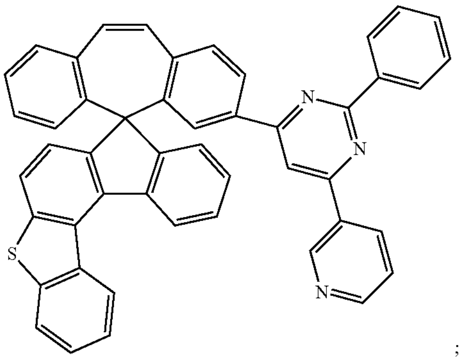
;
Compound CLVII
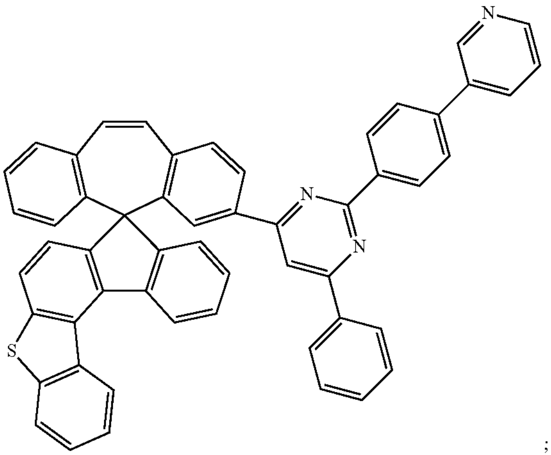
;
Compound CLVIII
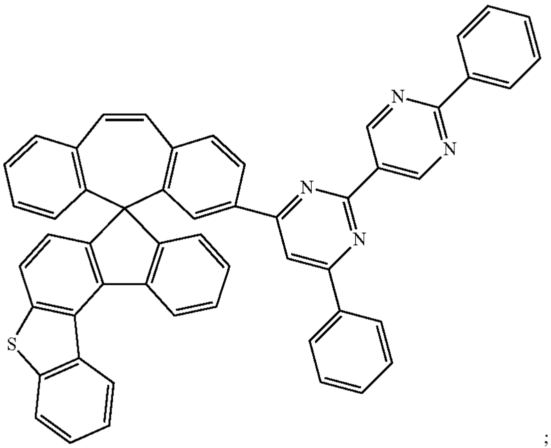
;
-continued
Compound CLIX
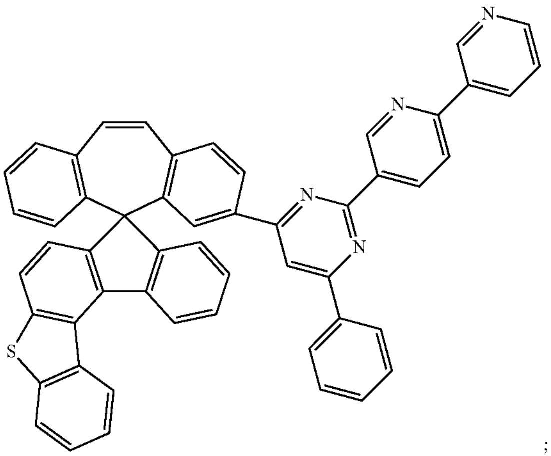
;
Compound CLX
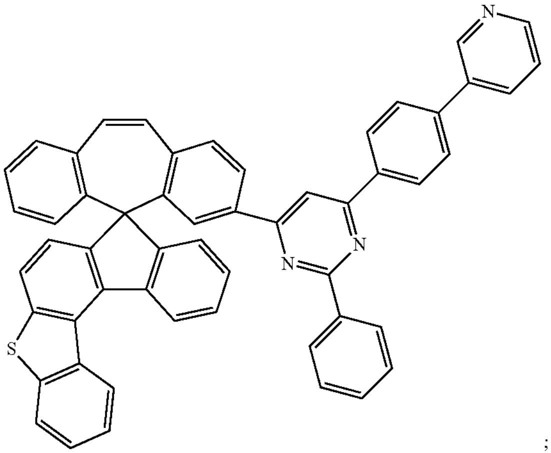
;
Compound CLXI
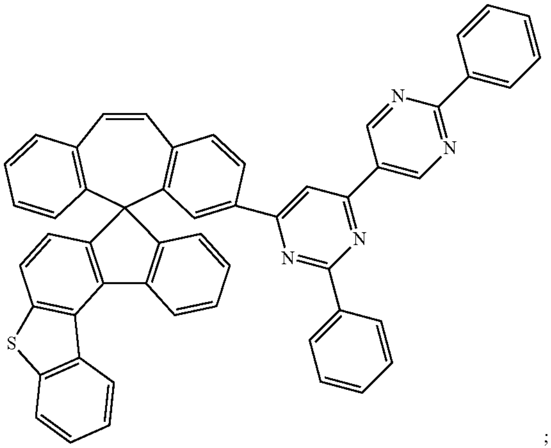
;

-continued
Compound CLXII
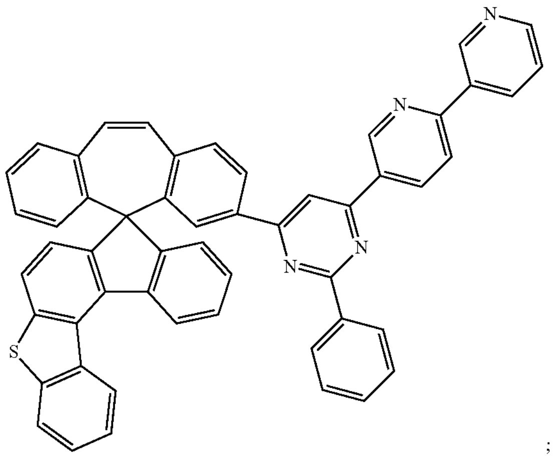
;
Compound CLXIII
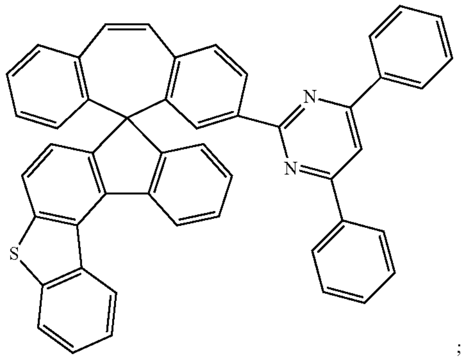
;
Compound CLXIV
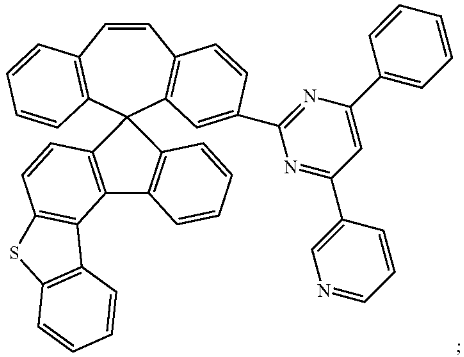
;
-continued
Compound CLXV
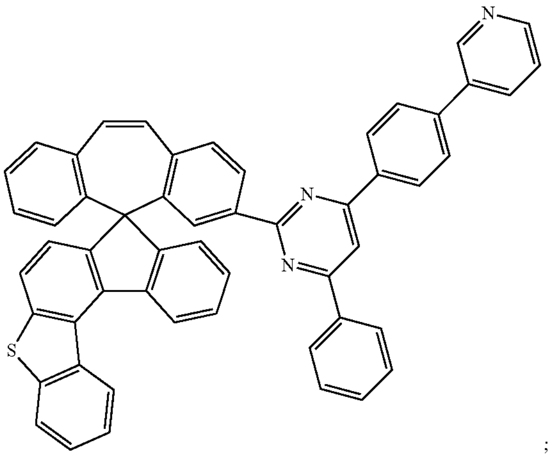
;
Compound CLXVI
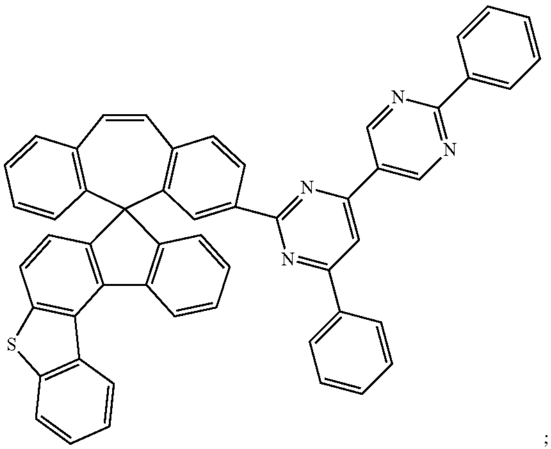
;
Compound CLXVII
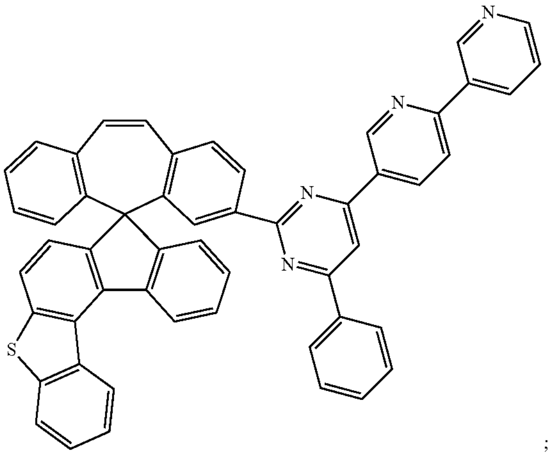
;

Compound CLXVIII
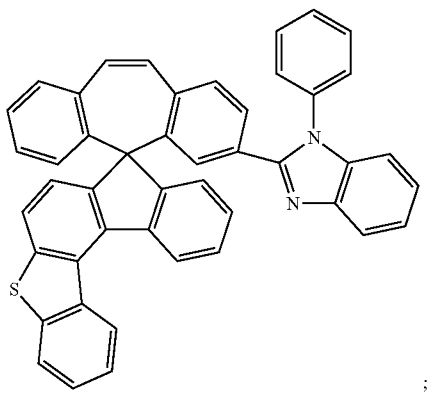
;
Compound CLXIX
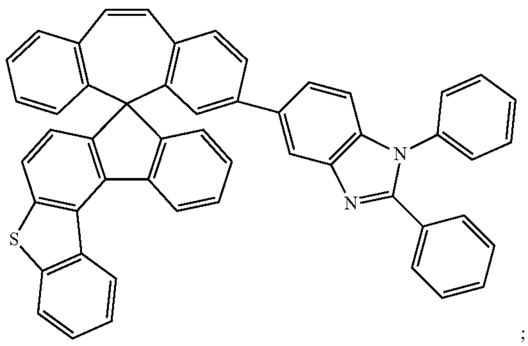
;
Compound CLXX
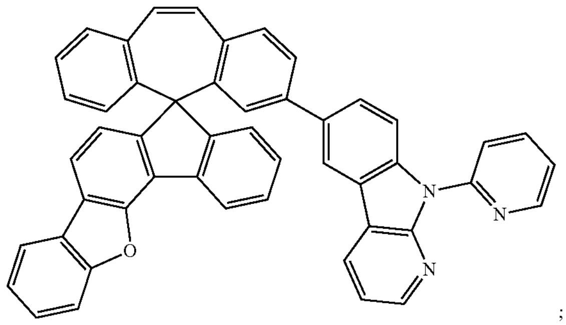
;
Compound CLXXI
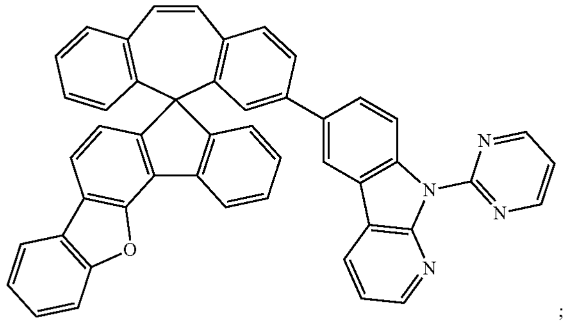
;
Compound CLXXII
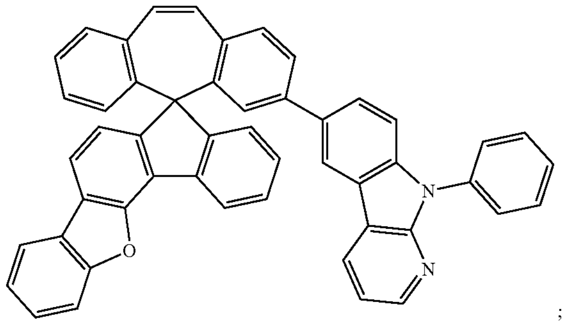
;
Compound CLXXIII
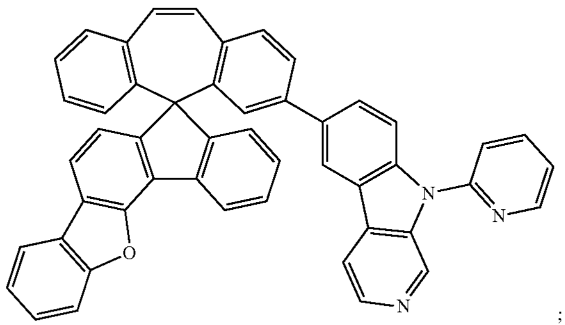
;
Compound CLXXIV
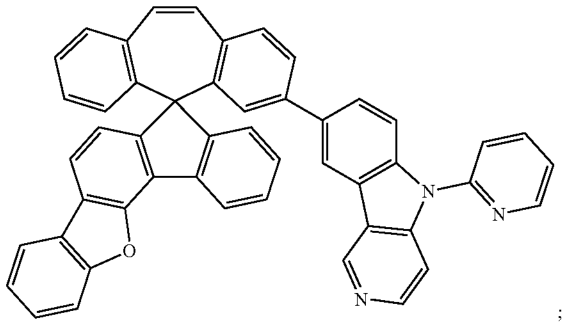
;
Compound CLXXV
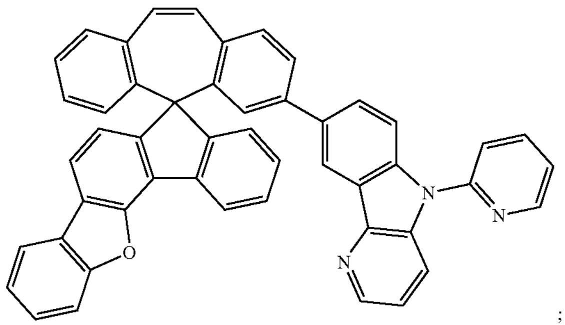
;

-continued
Compound CLXXVI
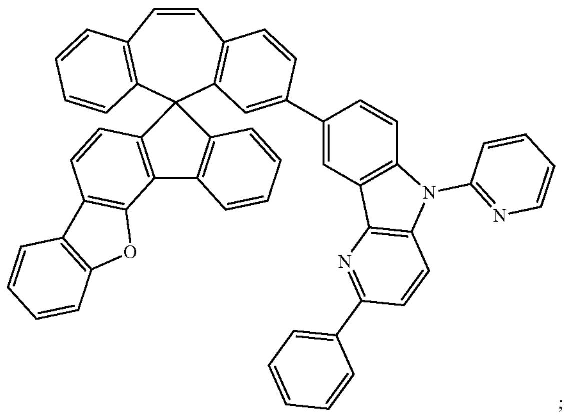
;
Compound CLXXVII
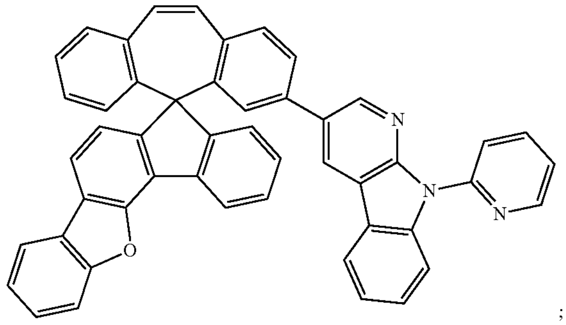
;
Compound CLXXVIII
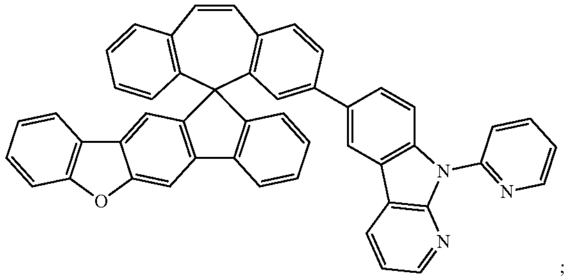
;
Compound CLXXIX
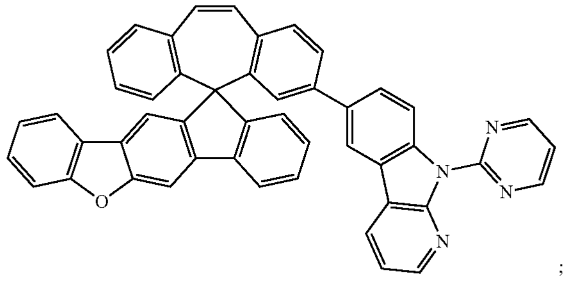
;
-continued
Compound CLXXX
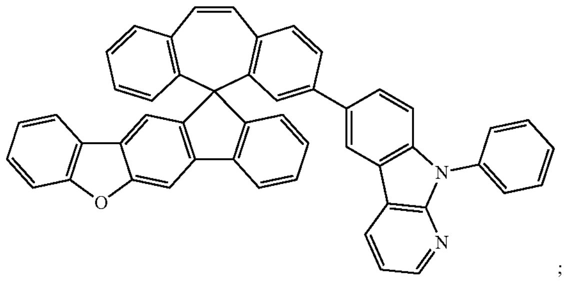
;
Compound CLXXXI
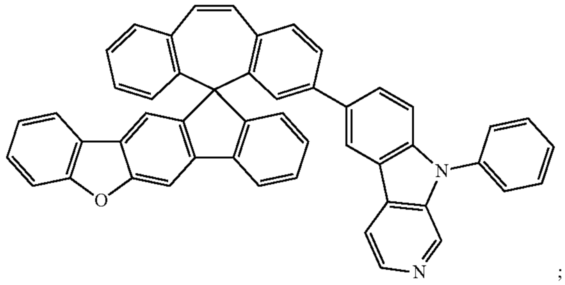
;
Compound CLXXXII
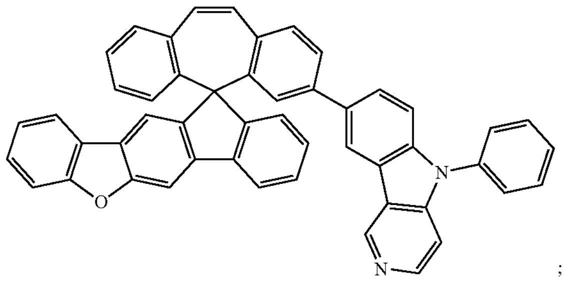
;
Compound CLXXXIII
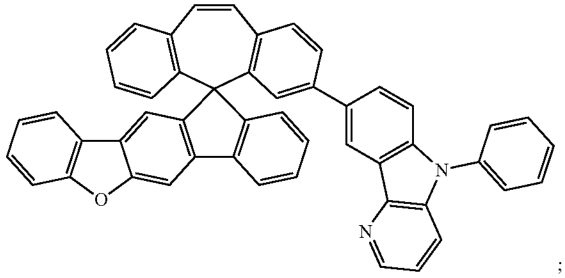
;
Compound CLXXXIV
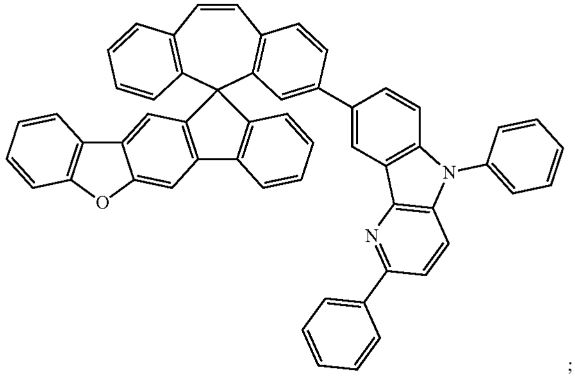
;

Compound CLXXXV
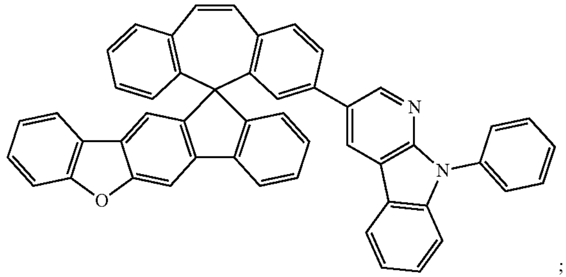
;
Compoound CLXXXVI
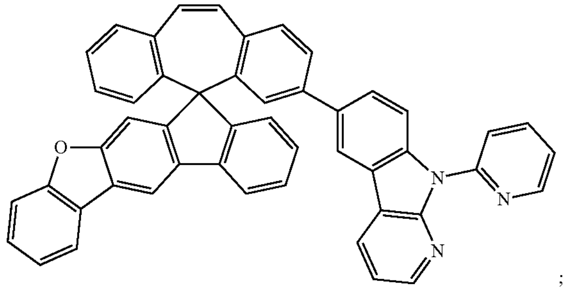
;
Compound CLXXXVII
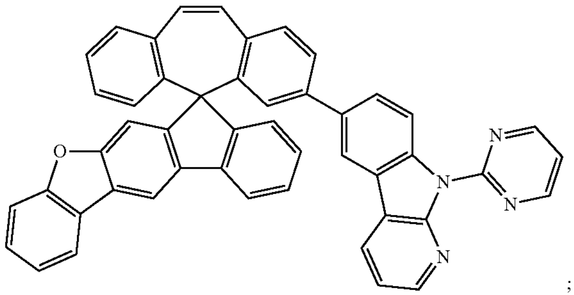
;
Compound CLXXXVIII
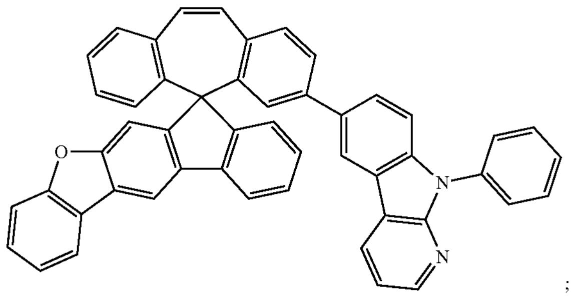
;
Compound CLXXXIX
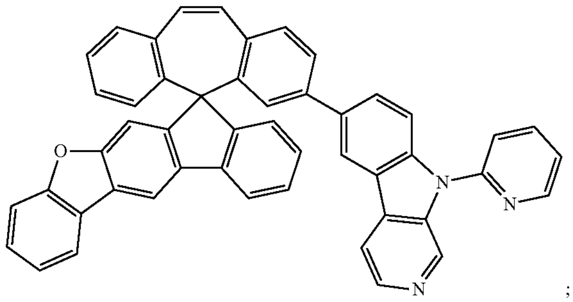
;
Compound CLXXXX
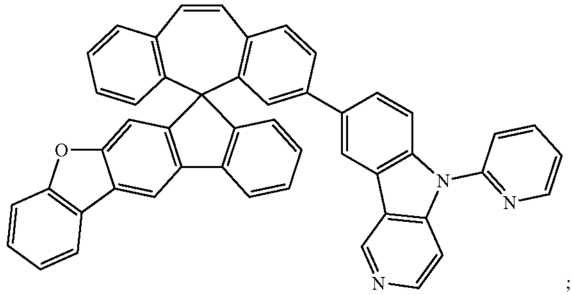
;
Compound CLXXXXI
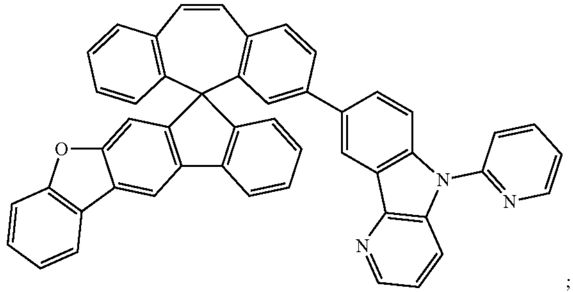
;
Compound CLXXXXII
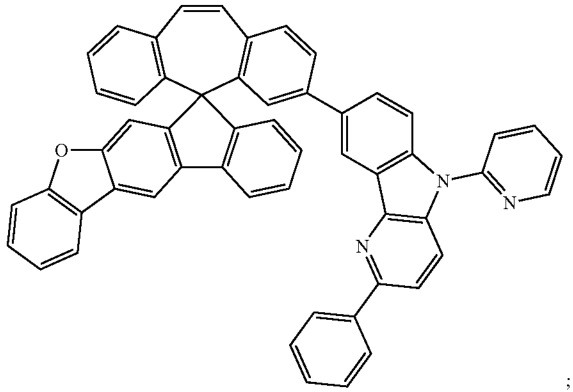
;
Compound CLXXXXIII
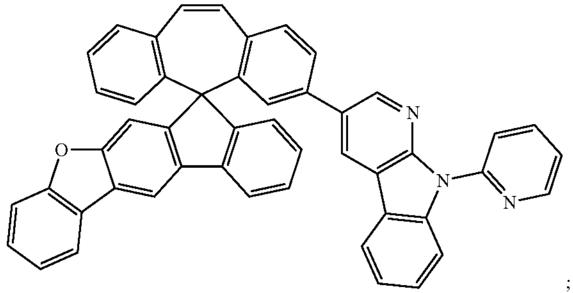
;

-continued
Compound CLXXXXIV
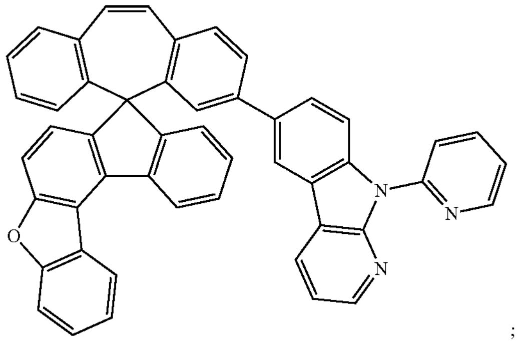
;
Compound CLXXXXV
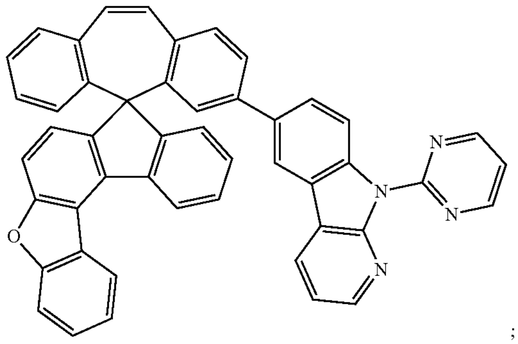
;
Compound CLXXXXVI
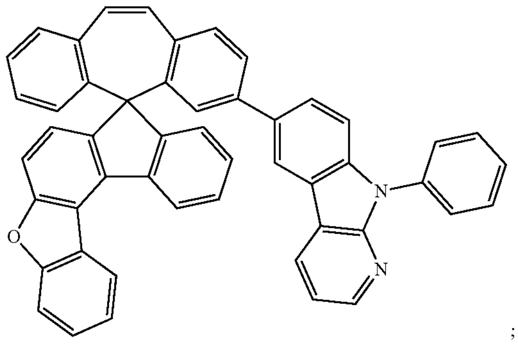
;
Compound CLXXXXVII
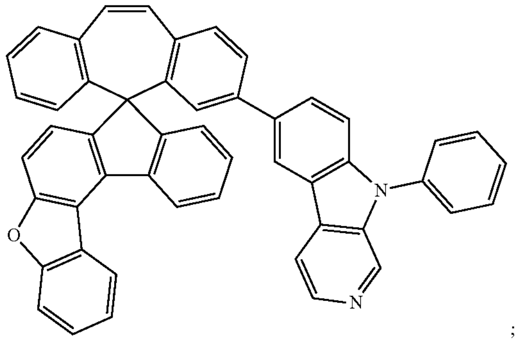
;
-continued
Compound CLXXXXVIII
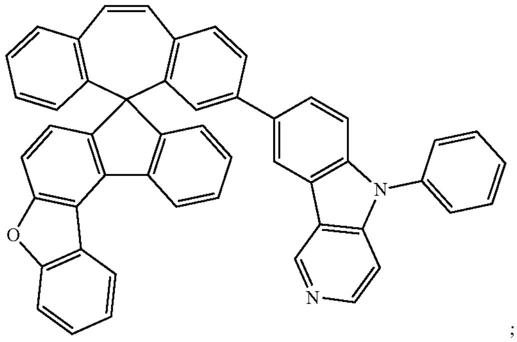
;
Compound CLXXXXIX
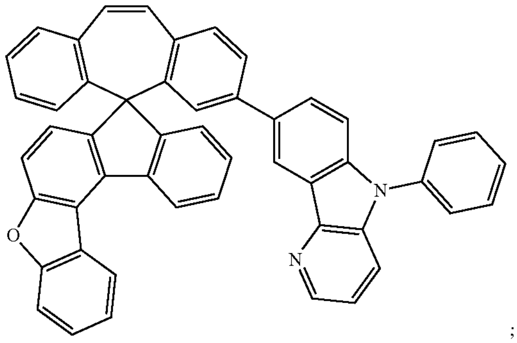
;
Compound CC
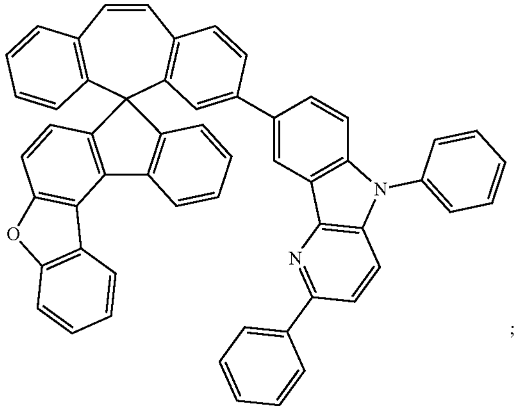
;
Compound CCI
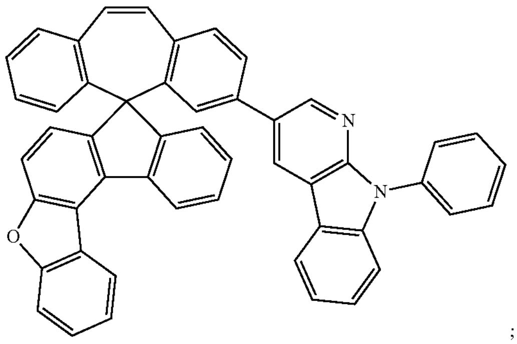
;

-continued
Compound CCII
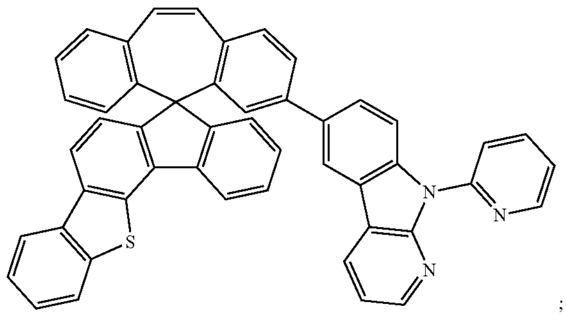
;
Compound CCIII
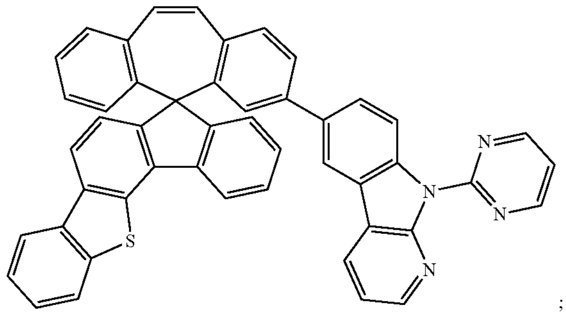
;
Compound CCIV
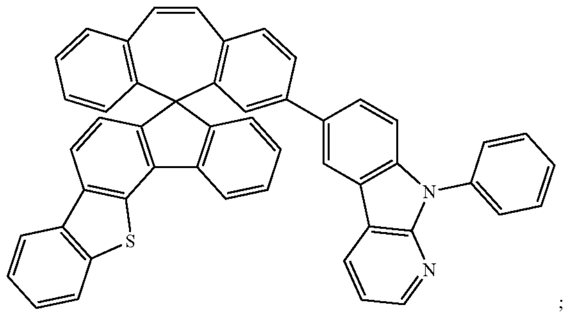
;
Compound CCV
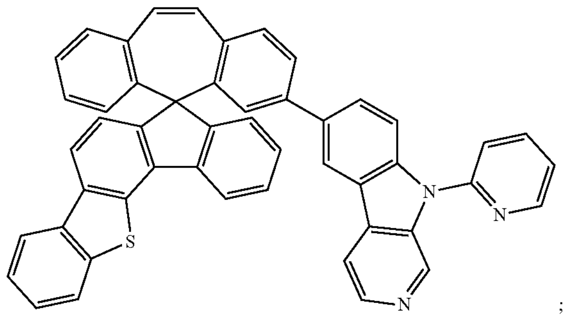
;
-continued
Compound CCVI
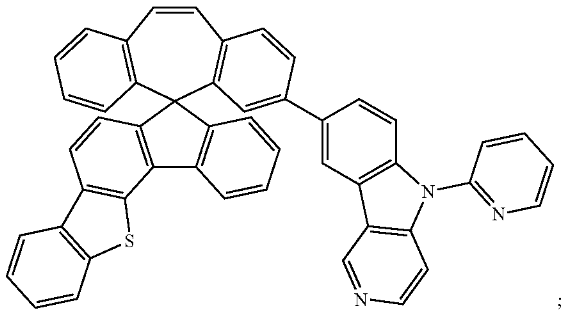
;
Compound CCVII
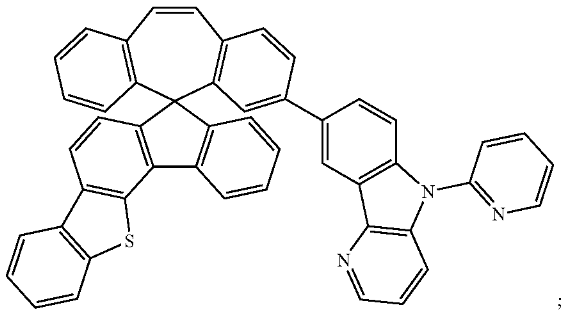
;
Compound CCVIII
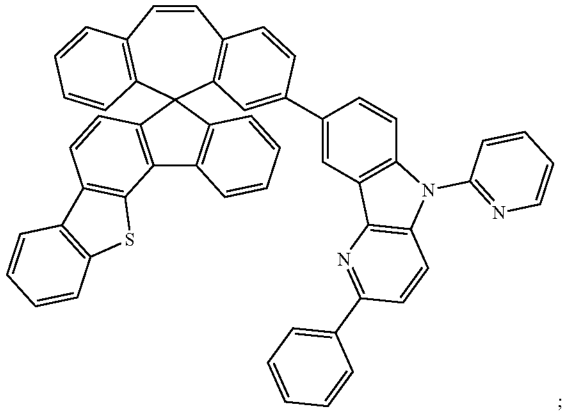
;
Compound CCIX
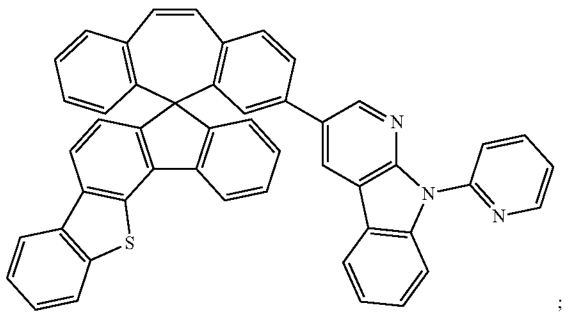
;

-continued
Compound CCX
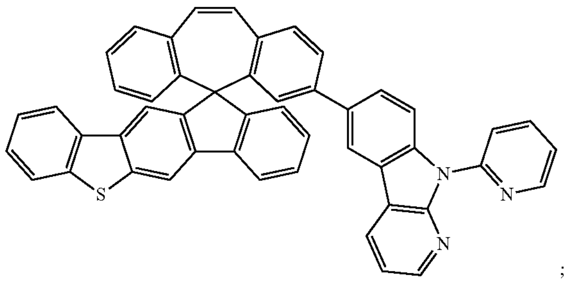
;
Compound CCXI
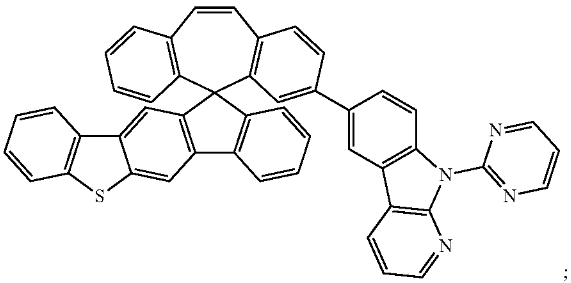
;
Compound CCXII
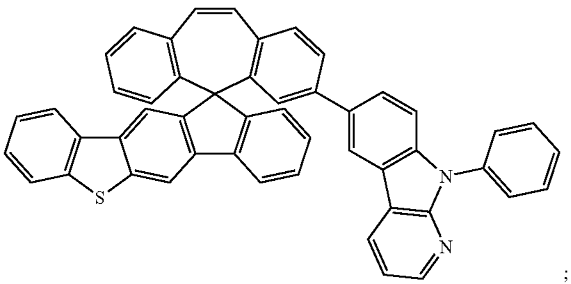
;
Compound CCXIII
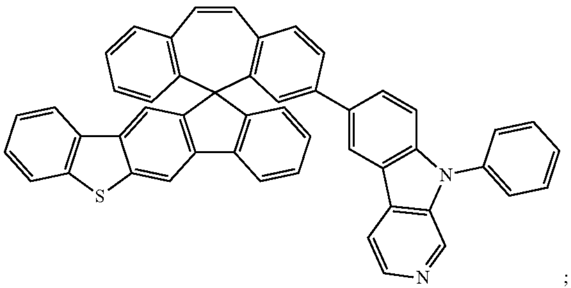
;
Compound CCXIV
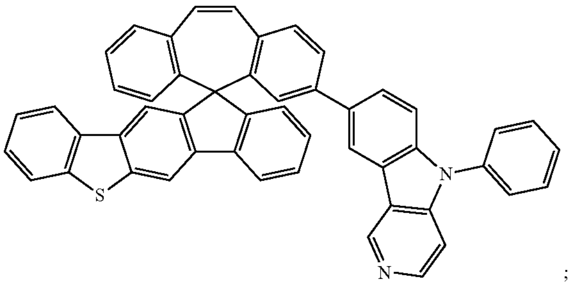
;
-continued
Compound CCXV
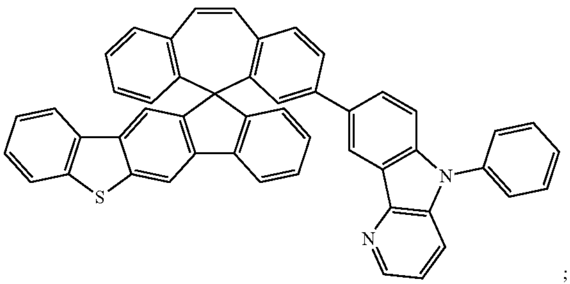
;
Compound CCXVI
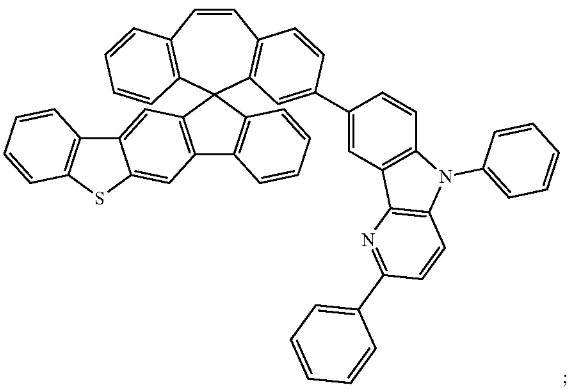
;
Compound CCXVII
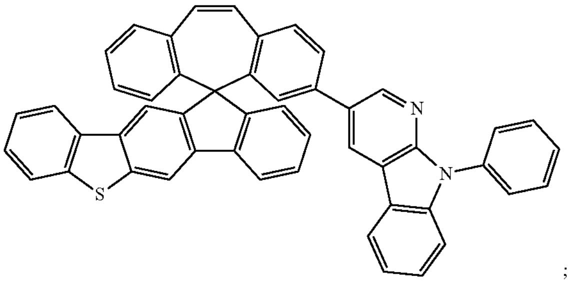
;
Compound CCXVIII
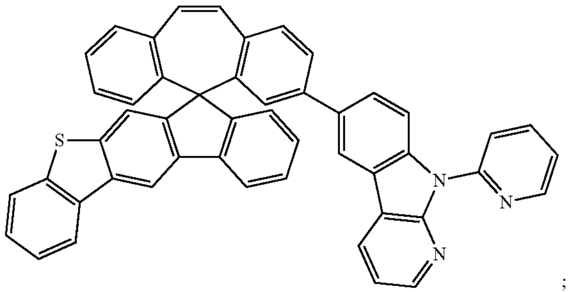
;

-continued
Compound CCXIX
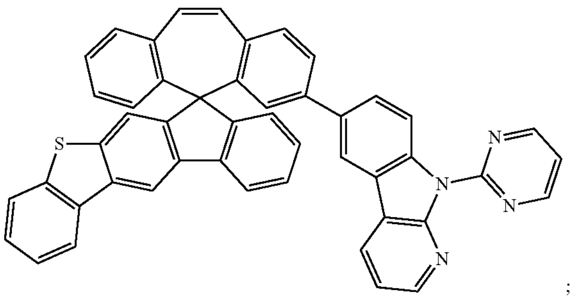
;
Compound CCXX
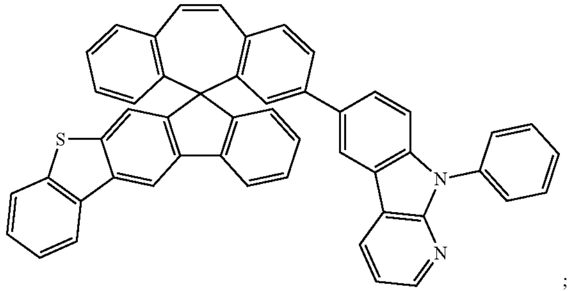
;
Compound CCXXI
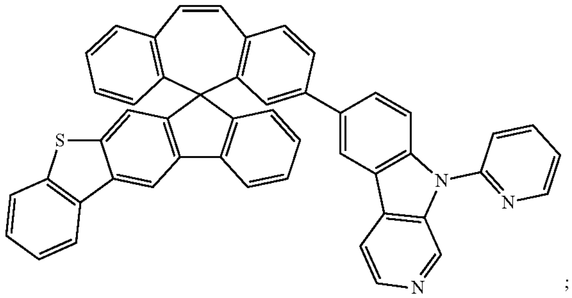
;
Compound CCXXII
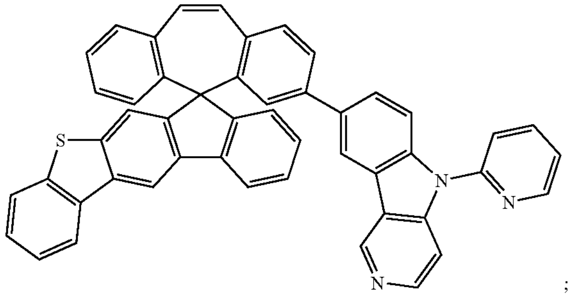
;
Compound CCXXIII
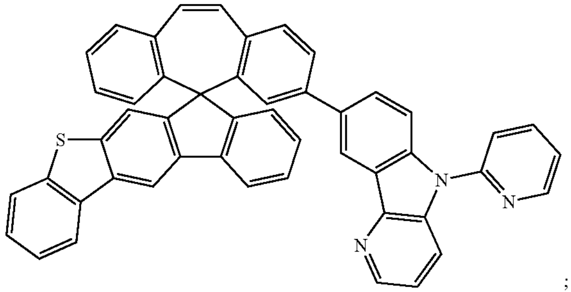
;
-continued
Compound CCXXIV
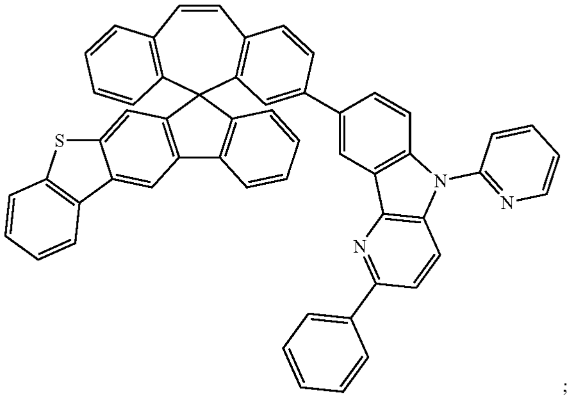
;
Compound CCXXV
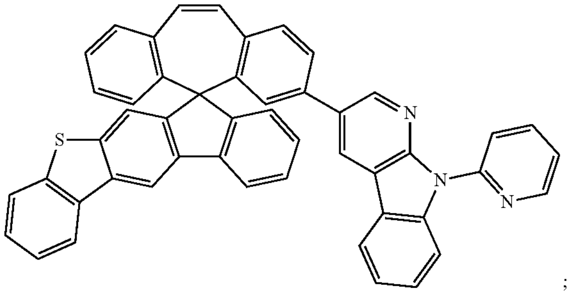
;
Compound CCXXVI
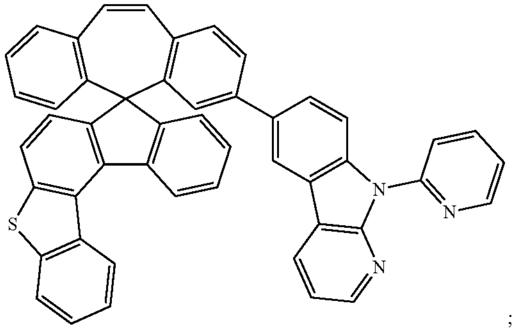
;
Compound CCXXVII
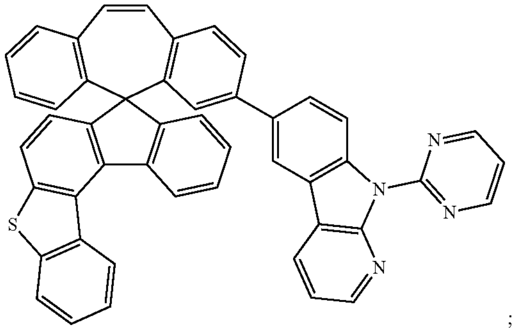
;

-continued

Compound CCXXVIII

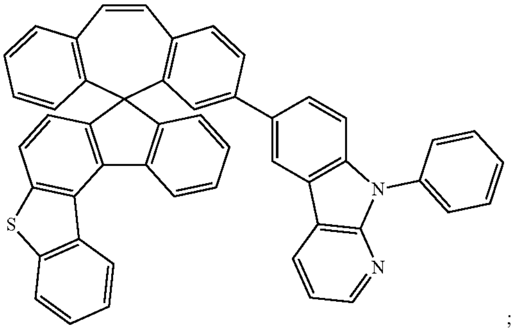

;

Compound CCXXIX

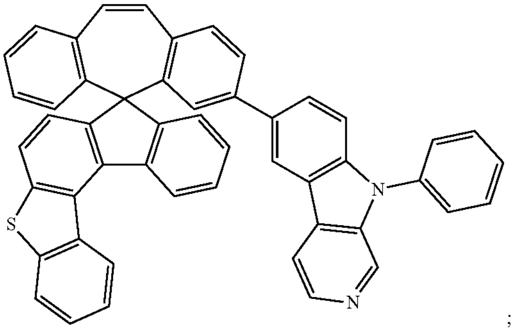

;

Compound CCXXX

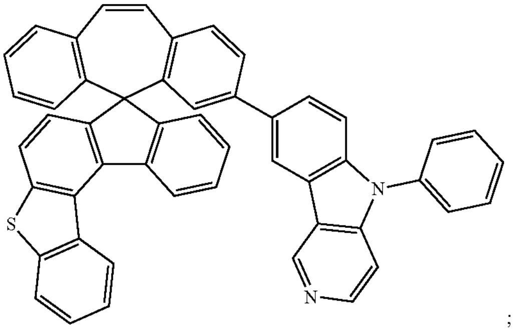

;

Compound CCXXXI

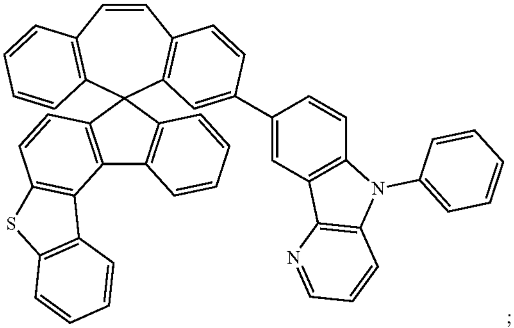

;

-continued

Compound CCXXXII

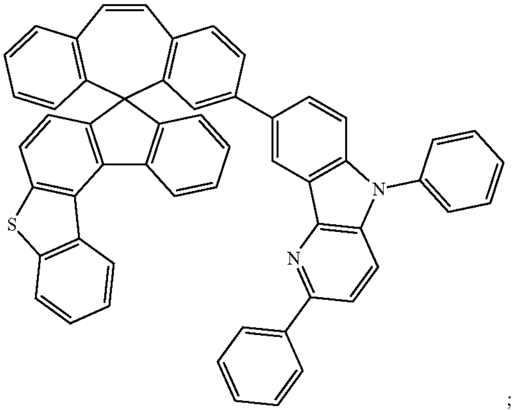

; and

Compound CCXXXIII

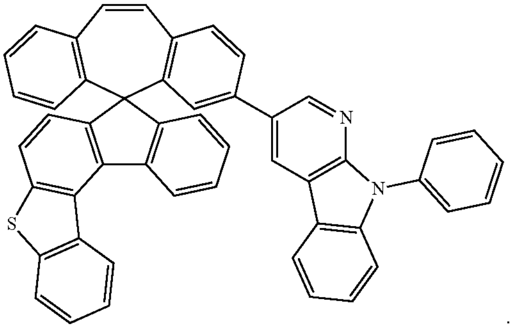

.

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material or a hole blocking layer.

Specifically, the organic light emitting device may comprise:

a hole injection layer formed on the first electrode;

a hole transport layer formed on the hole injection layer;

an emission layer formed on the hole transport layer;

an electron transport layer formed on the emission layer;

an electron injection layer formed between the electron transport layer and the second electrode.

In one embodiment, the organic layer may be the electron transport layer, i.e., the electron transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound such as Compounds I to CCXXXIII. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]imidazole;

bis(2-methyl-8-quinolinolato)(p-phenylphenolato) aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of the foresaid novel compound, 2,9-dimethyl-4,7-diphenyl-1,10-phenanthroline (BCP) or 2,3,5,6-tetramethyl-phenyl-1,4-(bis-phthalimide) (TMPP), but not limited thereto. In another embodiment, the organic layer may be the hole blocking layer, i.e., the hole blocking layer comprises the novel compound as stated above.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4"-tri(N-carbazolyl)-triphenylamine (TCTA), but not limited thereto.

In the presence of such a hole blocking layer and/or an electron blocking layer in an OLED, the OLED has a higher luminous efficiency compared to a typical OLED.

Said first and second hole transport layers may be made of, for example, but not limited to:

$N^1$,$N^{1'}$-(biphenyl-4,4'-diyl)bis($N^1$-(naphthalen-1-yl)-$N^4$,$N^{4'}$-diphenylbenzene-1,4-diamine); or $N^4$,$N^{4'}$-di(naphthalen-1-yl)-$N^4$,$N^{4'}$-diphenylbiphenyl-4,4'-diamine (NPB).

Said first and second hole injection layers may be made of, for example, but not limited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having perylene ligands, fluoranthene ligands or periflanthene ligands. For green OLEDs, the dopant of the emission material is, for example, but not limited to: diaminofluorenes; diaminoanthracenes; or organometallic compounds of iridium (II) having phenylpyridine ligands. For blue OLEDs, the dopant of the emission material is, for example, but not limited to: diaminofluorenes; diaminoanthracenes; diaminopyrenes; or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode. Other objectives, advantages and novel features of the invention will become more apparent from the following detailed description when taken in conjunction with the accompanying drawings.

DETAILED DESCRIPTION OF THE PREFERRED EMBODIMENTS

Figure 1:
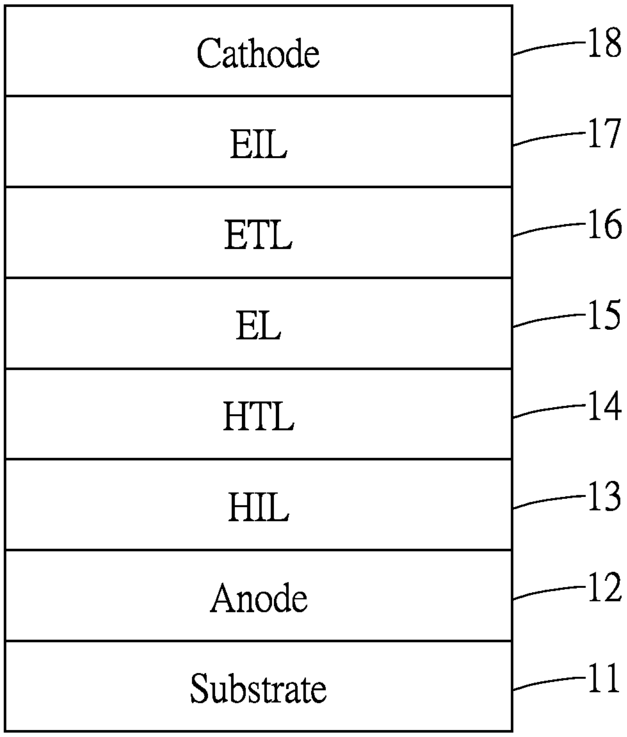
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

Scheme A1

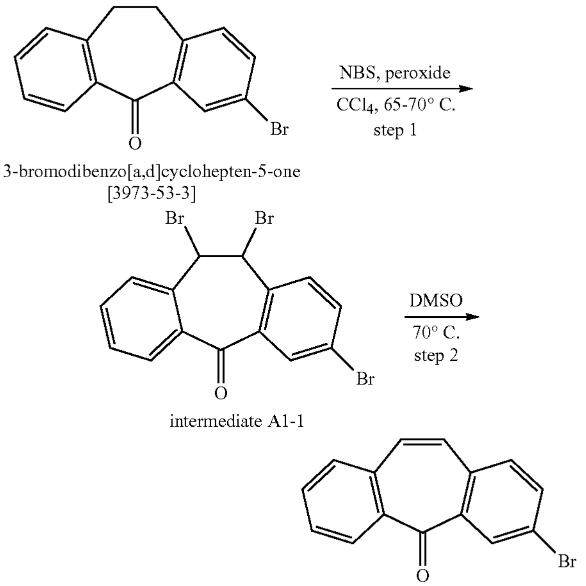

3-bromodibenzo[a,d]cyclohepten-5-one [3973-53-3]

intermediate A1-1 intermediate A1

Step 1: synthesis of Intermediate A1-1

A mixture of 3-bromodibenzo[a,d]cyclohepten-5-one (86 g, 1.0 eq), N-bromosuccinimide (NBS) (106 g, 2 eq), benzyl peroxide (0.7 g, 0.01 eq) in carbon tetrachloride ($CCl_4$) (5 times of starting materials) was heated to about 65° C. to 70° C. The reaction progress was monitored by high performance liquid chromatography (HPLC). After completion of the reaction, the precipitate was separated by filtration and washed with $CH_3OH$, which was then purified by recrystallization. The purified product was concentrated to dryness, whereby white solid products were obtained in a yield of 92.3%.

The solid product was identified as Intermediate A1-1 by a field desorption mass spectroscopy (FD-MS) analysis. FD-MS analysis: $C_{15}H_9Br_3O$: theoretical value of 444.94 and observed value of 444.94.

Step 2: Synthesis of Intermediate A1

Intermediate A1-1 (1.0 eq) in dimethyl sulfoxide (DMSO) (w/v=1/3 to the reactants) was heated to 70° C. The reaction was monitored by HPLC. After completion of the reaction, the reaction mixture was quenched with ice water. The precipitate was separated by filtration and then purified by column chromatography on silica gel. Intermediate A1 was obtained as pale yellow solid in 93% yield.

The pale yellow solid product was identified as Intermediate A1 by FD-MS analysis. FD-MS analysis $C_{15}H_9BrO$: theoretical value 285.14, observed value 285.14.

Synthesis of Intermediate A2

Intermediate A2 used for preparing a novel compound was synthesized in a similar manner as Intermediate A1 through steps 1 and 2, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

Scheme A2

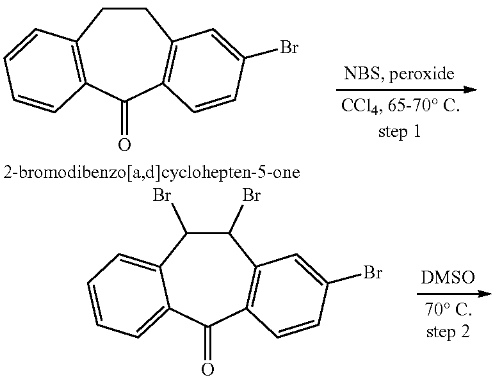

2-bromodibenzo[a,d]cyclohepten-5-one

Intermediate A2-1

-continued

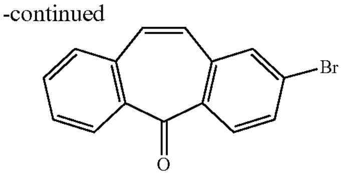
Intermediate A2

Synthesis of Intermediate A3

Intermediate A3 used for preparing a novel compound was synthesized in a similar manner as Intermediate A1 through steps 1 and 2, except that the starting material 3-bromodibenzo[a,d]cyclohepten-5-one was replaced by 3,7-dibromodibenzo[a,d]cyclohepten-5-one (CAS No. 226946-20-9). The synthesis pathway of Intermediate A3 was summarized in Scheme A3. All intermediates were analyzed as described above, and the results were listed in Table 1.

Scheme A3

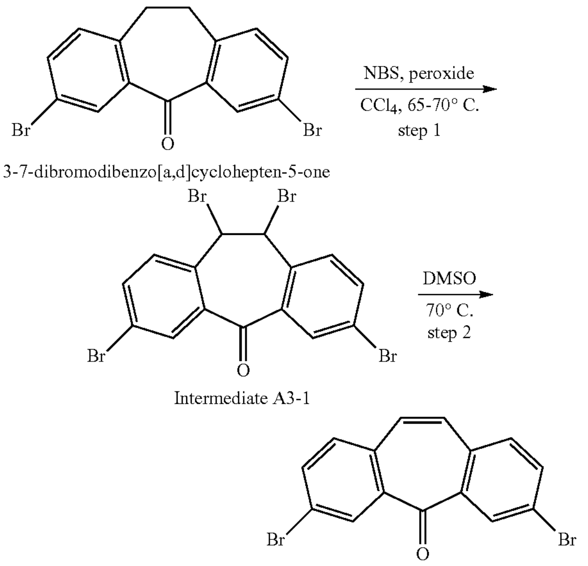

3-7-dibromodibenzo[a,d]cyclohepten-5-one

Intermediate A3-1

Intermediate A3

TABLE 1 chemical structures, yields, formulae, and mass ($M^+$) analyzed by FD-MS of intermediates.

| Intermediate | A1-1 | A1 |
|---|---|---|
| Chemical Structure | 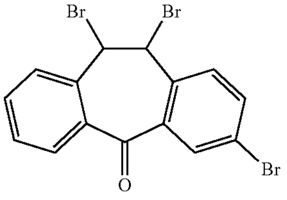 [SMILES: O=C1c2ccccc2C(Br)C(Br)c2ccc(Br)cc21] | 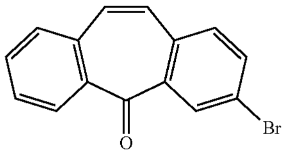 |
| Yield | 92.3% | 93% |
| Formula | $C_{15}H_9Br_3O$ | $C_{15}H_9BrO$ |
| Mass ($M^+$) | 444.94 | 285.14 |

TABLE 1-continued

| chemical structures, yields, formulae, and mass ($M^+$) analyzed by FD-MS of intermediates. | | |
|---|---|---|
| Intermediate | A2-1 | A2 |
| Chemical Structure | 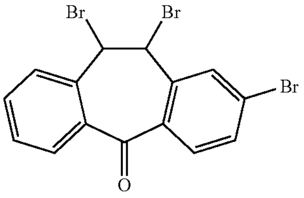 [SMILES: O=C1c2ccccc2C(Br)C(Br)c2cc(Br)ccc21] | 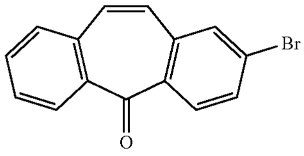 |
| Yield | 91.5% | 87% |
| Formula | $C_{15}H_9Br_3O$ | $C_{15}H_9BrO$ |
| Mass ($M^+$) | 444.94 | 285.14 |
| Intermediate | A3-1 | A3 |
| Chemical Structure | 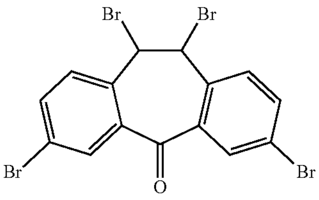 [SMILES: O=C1c2cc(Br)ccc2C(Br)C(Br)c2ccc(Br)cc21] | 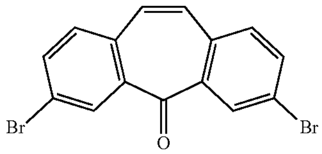 |
| Yield | 93.7% | 90% |
| Formula | $C_{15}H_8Br_4O$ | $C_{15}H_8Br_2O$ |
| Mass ($M^+$) | 523.84 | 364.03 |

Modifications of Intermediates A1 to A3

In addition to the Intermediates A1 to A3, one person skilled in the art can adopt other starting materials and successfully synthesize other desired intermediates through a reaction mechanism similar to Scheme A1 to A3. Applicable modifications of Intermediates A1 to A3 may be, for example, but not limited to, Intermediates A4 to A15 as follows.

Intermediate A4

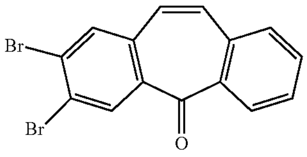

;

Intermediate A5

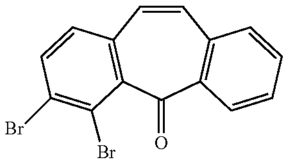

;

Intermediate A6

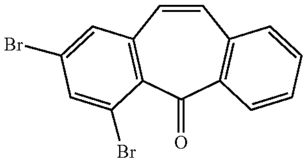

;

-continued

Intermediate A7

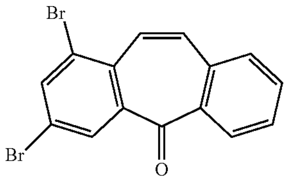

;

Intermediate A8

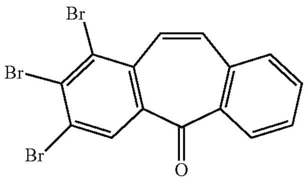

;

Intermediate A9

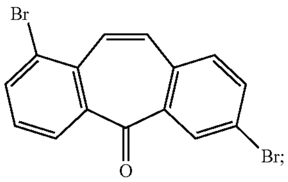

Intermediate A10

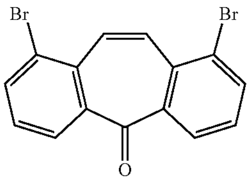

;

-continued

Intermediate A11

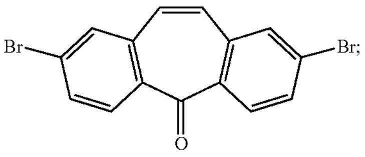

Intermediate A12

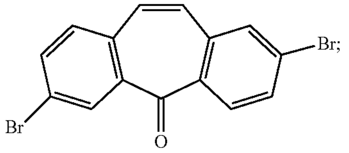

Intermediate A13

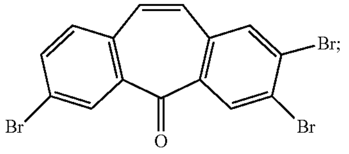

Intermediate A14

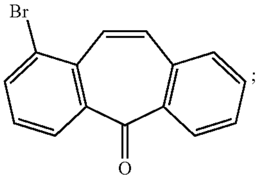

Intermediate A15

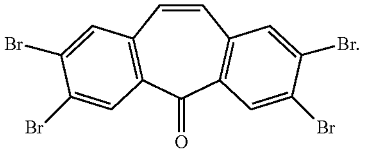

Synthesis of Intermediates B1 to B6

Intermediates B1 to B6 were synthesized by reacting 1-bromo-2-iodobenzene and heteroaryl boronic acid (Reactant An). A general synthesis pathway for Intermediate Bn was summarized in Scheme B. In the following Scheme B, "Reactant An" may be any one of Reactants A1 to A6 as listed in Table 2 or the like, and "Intermediate Bn" may be any one of Intermediates B1 to B6 as listed in Table 2.

Scheme B

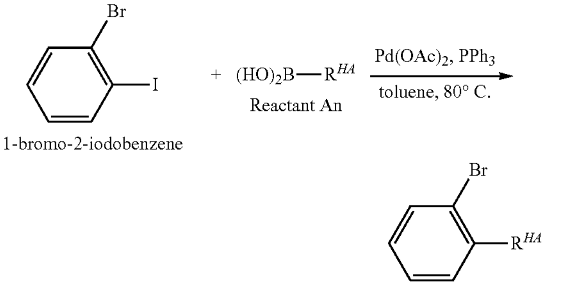

1-bromo-2-iodobenzene

Reactant An

Intermediate Bn $R^{HA}$: heteroaryl ring containing furan or thiofuran group

According to the Scheme B, each of Intermediates B1 to B6 was synthesized by the steps as follows.

1-bromo-2-iodobenzene (1.0 eq), Reactant An (1.2 eq), potassium carbonate (3.0 eq), 200 ml of toluene, $PPh_3$ (0.06 eq) and $Pd(OAc)_2$ (0.015 eq) were mixed and stirred at 80° C. After reaction was completed, the reaction mixture was allowed to be cooled to room temperature, and an organic layer was extracted with saturated aqueous solution of sodium chloride and EA and dried over magnesium sulfate, followed by filtering with silica gel. After a solid prepared by concentrating the filtrate under reduced pressure was suspended in hexane, the suspension was filtered again and washed with hexane to obtain Intermediate Bn. All intermediate Bn, including Intermediates B1 to B6, were analyzed according to the methods as described above, and the results were listed in Table 2.

TABLE 2

Reactant An used for preparing Intermediates B1 to B6, and the chemical structures, yields, formulae, and mass analyzed by FD-MS of Intermediates B1 to B6.

| Reactant An | Intermediate Bn | | |
|---|---|---|---|
| Chemical Structure | Chemical Structure | Yield | Formula/ Mass ($M^+$) |
| 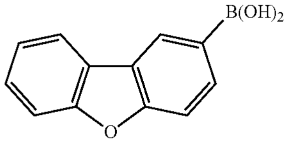 Reactant A1 | 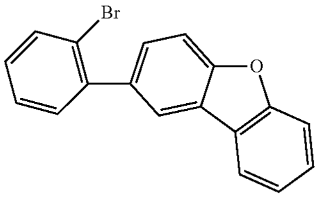 Intermediate B1 | 87% | $C_{18}H_{11}BrO$/ 323.18 |

TABLE 2-continued

Reactant An used for preparing Intermediates B1 to B6, and the chemical structures, yields, formulae, and mass analyzed by FD-MS of Intermediates B1 to B6.

| Reactant An Chemical Structure | Intermediate Bn Chemical Structure | Yield | Formula/ Mass ($M^+$) |
|---|---|---|---|
| 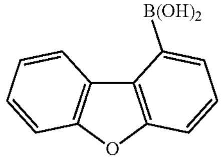 Reactant A2 | 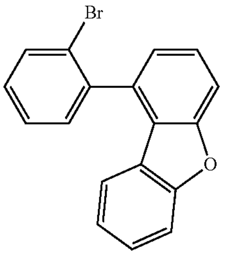 Intermediate B2 | 88% | $C_{18}H_{11}BrO$/ 323.18 |
| 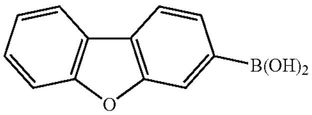 Reactant A3 | 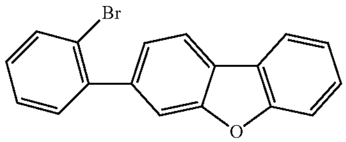 Intermediate B3 | 80% | $C_{18}H_{11}BrO$/ 323.18 |
| 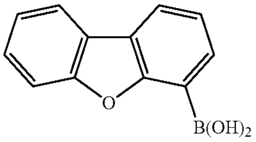 Reactant A4 | 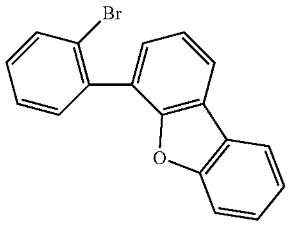 Intermediate B4 | 85% | $C_{18}H_{11}BrO$/ 323.18 |
| 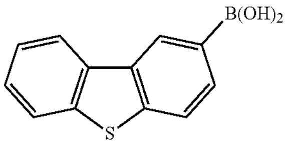 Reactant A5 | 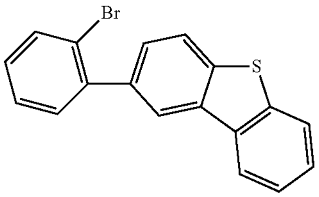 Intermediate B5 | 84% | $C_{18}H_{11}BrS$/ 339.25 |
| 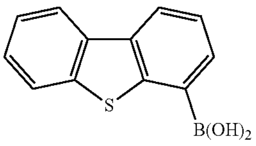 Reactant A6 | 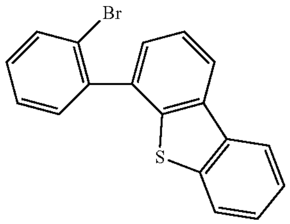 Intermediate B6 | 88% | $C_{18}H_{11}BrS$/ 339.25 |

Modifications of Intermediates B1 to B6

In addition to the Intermediates B1 to B6, one person skilled in the art can adopt any dihalobenzenes other than 1-bromo-2-iodobenzene and any heteroaryl boronic acids other than Reactants A1 to A6 to successfully synthesize other desired Intermediate Bn through a reaction mechanism similar to Scheme B. Applicable modifications of Intermediates B1 to B6 may be, for example, but not limited to, Intermediates B7 and B8 as follows.

Intermediate B7

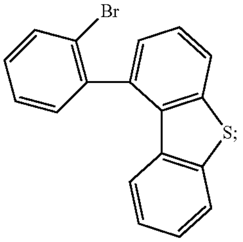

; or

Intermediate B8

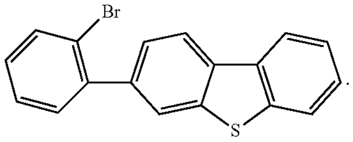

.

Synthesis of Intermediate Cn

The foresaid Intermediates B1 to B8, especially Intermediates B1 to B6, could be further adopted to synthesize Intermediate Cn. A general synthesis pathway for Intermediate Cn was summarized in Scheme C1. In the following Scheme C1, "Intermediate An" may be any one of foresaid Intermediates A1 to A15 or the like, "Intermediate Bn" may be any one of foresaid Intermediates B1 to B8 or the like, and "Intermediate Cn" may be any one of Intermediates C1 to C9 as listed in Table 3-1 or the like. Intermediates C1 to C9 were each synthesized by the following steps.

Scheme C1

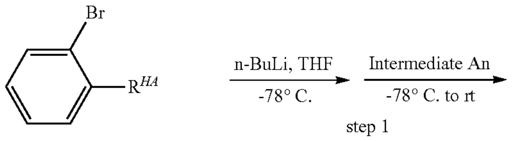

$R^{HA}$: heteroaryl ring containing furan or thiofuran group

Intermediate Bn

-continued

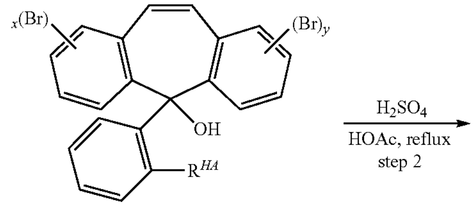

x, y = 0 or 1

Alcohol intermediate Cn-1

Intermediate Cn

Step 1: Synthesis of Intermediate Cn-1

Intermediate Bn (1.0 eq) was dissolved in 120 mL of anhydrous THF (0.4M), and cooled to −78° C. n-Butyllithium (n-BuLi) (2.5 M, 1.0 eq) was slowly added to the above cooled solution, and reaction mass was stirred for 1 h. After 1 h of stirring, Intermediate An (0.7 eq) was added to the reaction solution and stirred for additional 3 h at 25° C. After completion of the reaction, it was quenched by saturated solution of ammonium chloride, and extracted with organic solvent. The organic layer was separated, concentrated, and recrystallized with petroleum ether to obtain a white solid product. The white solid product was identified as Intermediate Cn-1 by FD-MS analysis. Take Intermediate C1-1 as an example, FD-MS analysis: $C_{33}H_{21}BrO_2$: theoretical value 529.42 and observed value 529.42.

Intermediate Cn-1 could be directly used in step 2 without further purification. Each Intermediate Cn-1 synthesized by reacting different Intermediate An with Intermediate Bn was identified by FD-MS. The chemical structure of each Intermediate Cn-1 was listed in Table 3-1.

Step 2: Synthesis of Intermediate Cn

Intermediate Cn-1 (1.0 eq), acetic acid (w/v=1/3 to the reactants) and $H_2SO_4$(5 drops) were mixed, and the mixture was stirred at 110° C. for 6 h. The solvent was then removed under reduced pressure, and the residue was purified with column chromatography. The residual mass was recrystallized with toluene to obtain a white solid product.

The solid product was identified by FD-MS analysis. The chemical structures, yields, formulae, and mass analyzed by FD-MS of Intermediates C1 to C9 were listed in Table 3-1.

TABLE 3-1

Intermediate An and Bn used for preparing Intermediates Cn-1, chemical structures of Intermediates Cn-1, and chemical structures of Intermediates Cn, yields, formulae, and mass analyzed by FD-MS of Intermediates C1 to C9.

| | | Intermediate Cn-1 | | Intermediate Cn | |
|---|---|---|---|---|---|
| Inter-mediate An | Inter-mediate Bn | Chemical Structure | Yield (%) | Chemical Structure/ Formula/ Mass ($M^+$) | Yield (%) |
| A1 | B1 | 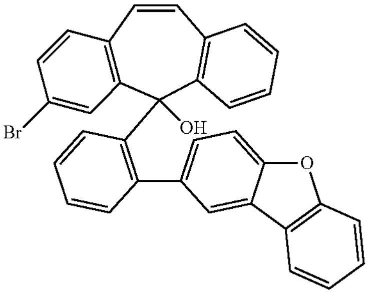 Intermediate C1-1 | 86 | 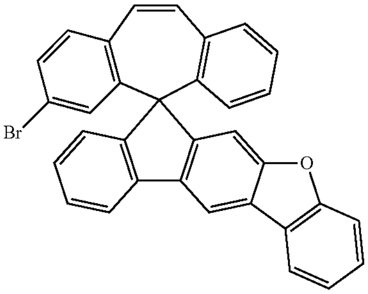 Intermediate C1/ $C_{33}H_{19}BrO$/ 511.41 | 95 |
| A2 | B1 | 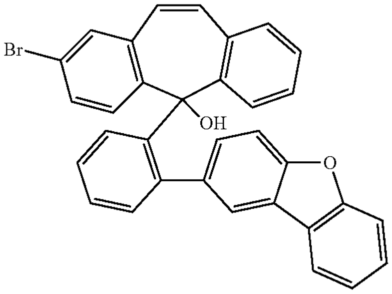 Intermediate C2-1 | 88 | 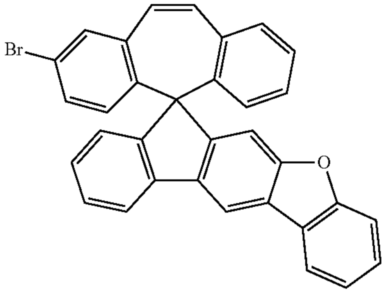 Intermediate C2/ $C_{33}H_{19}BrO$/ 511.41 | 91 |
| A3 | B1 | 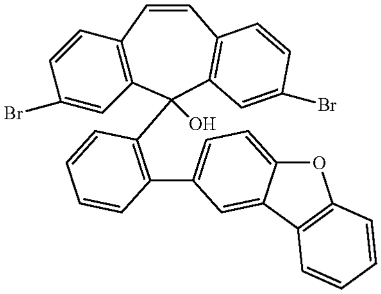 Intermediate C3-1 | 76 | 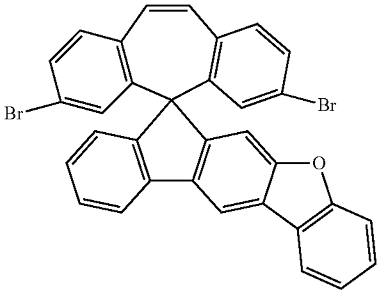 Intermediate C3/ $C_{33}H_{18}Br_2O$/ 590.30 | 81 |

TABLE 3-1-continued

Intermediate An and Bn used for preparing Intermediates Cn-1, chemical structures of Intermediates Cn-1, and chemical structures of Intermediates Cn, yields, formulae, and mass analyzed by FD-MS of Intermediates C1 to C9.

| | | Intermediate Cn-1 | | Intermediate Cn | |
|---|---|---|---|---|---|
| Intermediate An | Intermediate Bn | Chemical Structure | Yield (%) | Chemical Structure/ Formula/ Mass ($M^+$) | Yield (%) |
| A1 | B2 | 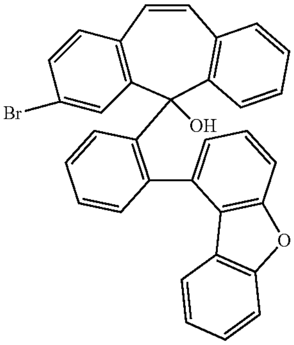 Intermediate C4-1 | 78 | 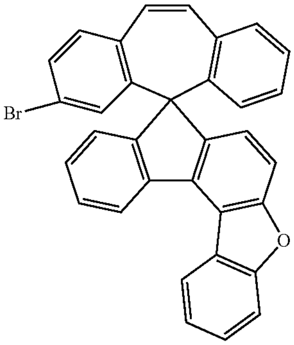 Intermediate C4/ $C_{33}H_{19}BrO$/ 511.41 | 87 |
| A1 | B3 | 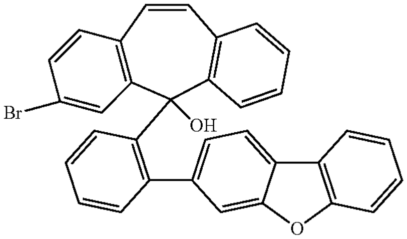 Intermediate C5-1 | 85 | 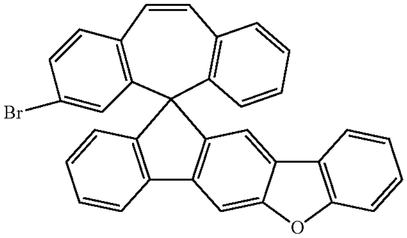 Intermediate C5/ $C_{33}H_{19}BrO$/ 511.41 | 80 |
| A1 | B4 | 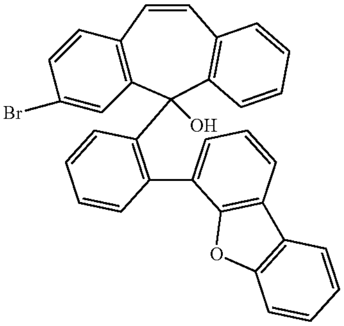 Intermediate C6-1 | 83 | 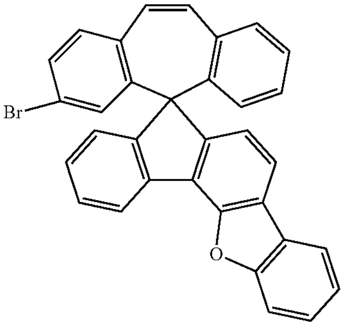 Intermediate C6/ $C_{33}H_{19}BrO$/ 511.41 | 95 |

TABLE 3-1-continued

Intermediate An and Bn used for preparing Intermediates Cn-1, chemical structures of Intermediates Cn-1, and chemical structures of Intermediates Cn, yields, formulae, and mass analyzed by FD-MS of Intermediates C1 to C9.

| Intermediate An | Intermediate Bn | Intermediate Cn-1 Chemical Structure | Intermediate Cn-1 Yield (%) | Intermediate Cn Chemical Structure/Formula/Mass ($M^+$) | Intermediate Cn Yield (%) |
|---|---|---|---|---|---|
| A1 | B5 | 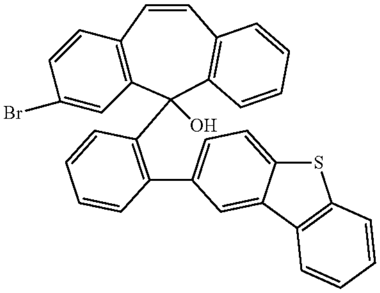 Intermediate C7-1 | 78 | 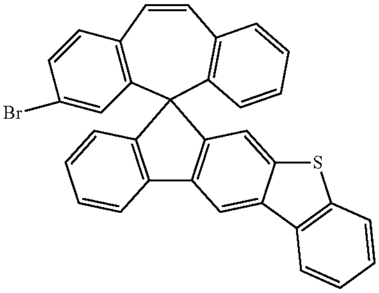 Intermediate C7/ $C_{33}H_{19}BrS$/ 527.48 | 93 |
| A2 | B5 | 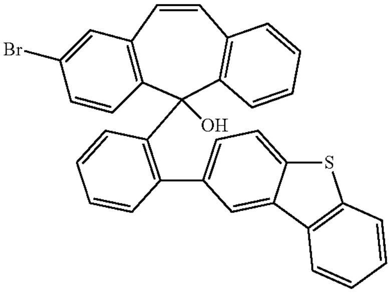 Intermediate C8-1 | 88 | 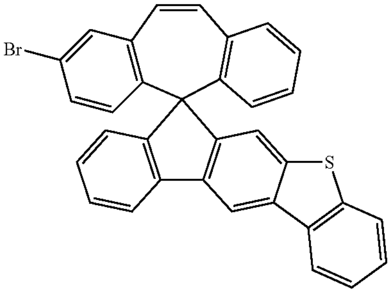 Intermediate C8/ $C_{33}H_{19}BrS$/ 527.48 | 85 |
| A1 | B6 | 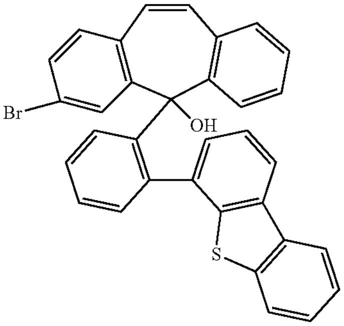 Intermediate C9-1 | 75 | 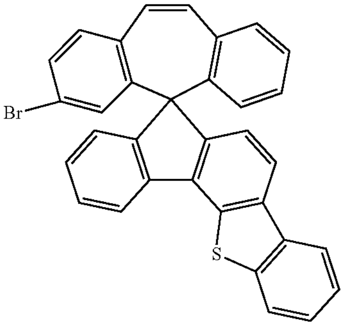 Intermediate C9/ $C_{33}H_{19}BrS$/ 527.48 | 88 |

Modifications of Intermediates C1 to C9

In addition to the Intermediates C1 to C9, one person skilled in the art can adopt any intermediate An other than Intermediates A1 to A3 and any Intermediate Bn other than Intermediates B1 to B6 to successfully synthesize other desired Intermediate Cn through a reaction mechanism similar to Scheme C1. Applicable modifications of Intermediates C1 to C9 may be, for example, but not limited to, Intermediates C10 to C26 as follows.

-continued
Intermediate C10
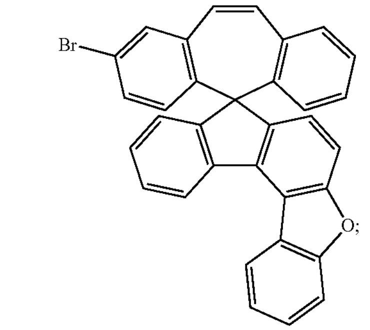
Intermediate C11
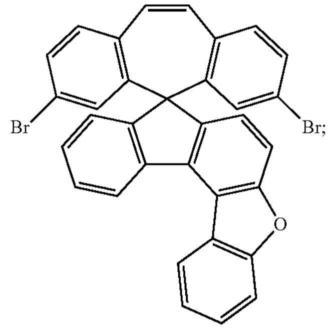
Intermediate C12
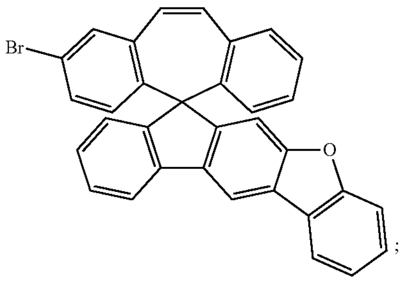
Intermediate C13
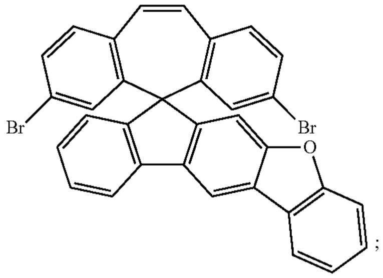
Intermediate C14
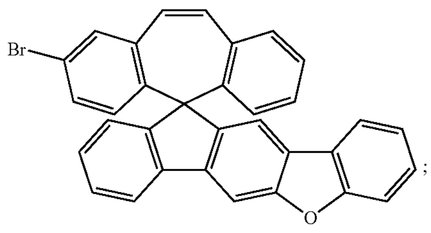
Intermediate C15
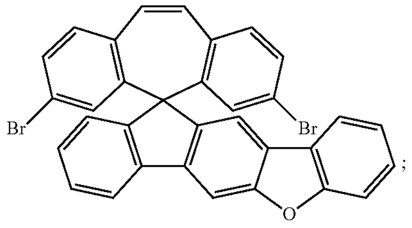
Interemdiate C16
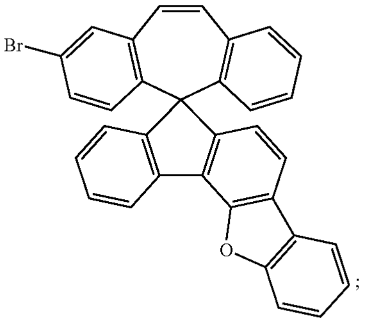
Intermediate C17
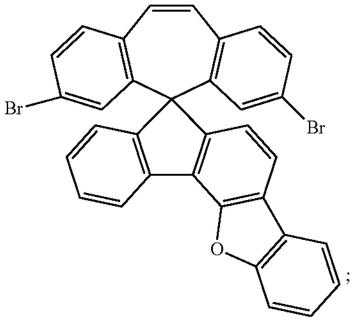
Intermediate C18
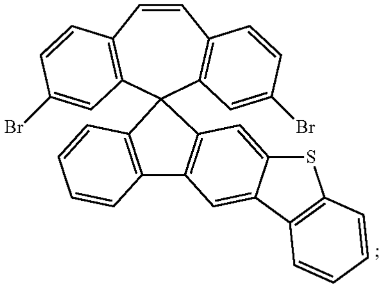
Intermediate C19
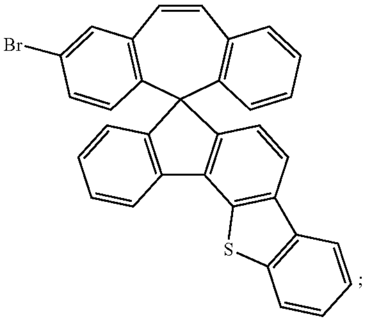

-continued

Intermediate C20

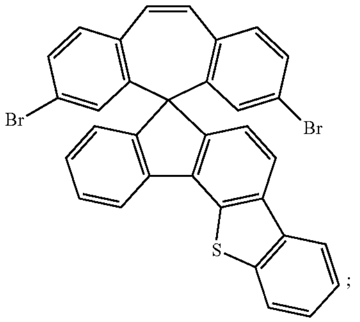

;

Intermediate C21

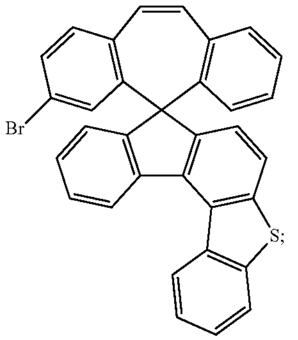

;

Intermediate C22

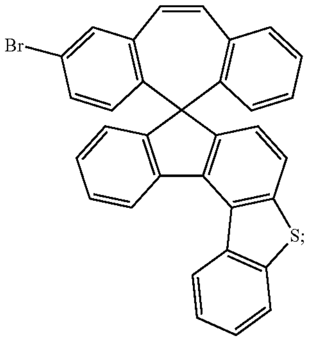

;

Intermediate C23

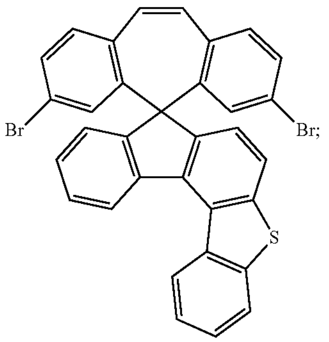

;

Intermediate C24

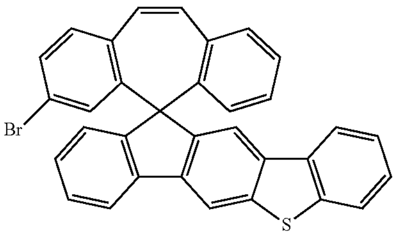

;

-continued

Intermediate C25

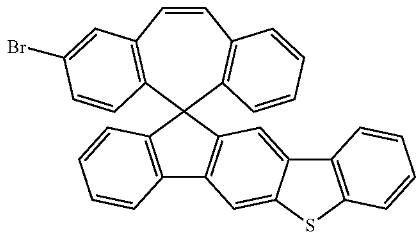

;

Intermediate C26

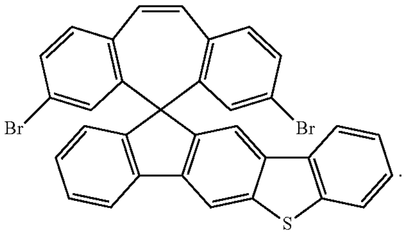

.

Synthesis of Intermediate Cn-B

The foresaid Intermediate Cn could be further modified into an Intermediate Cn-B through Miyaura borylation reaction. "Intermediate Cn-B" was directed to a compound derived from Intermediate Cn whose bromo group was replaced by (pinacolato)boron group. A synthesis pathway of Intermediate Cn-B was summarized in Scheme C1-B. Intermediate Cn-B was synthesized by the following steps.

Scheme C1-B

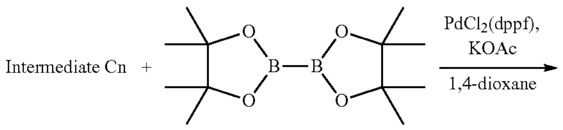

bis(pinacolato)diboron

Intermediate Cn-B

A mixture of bis(pinacolato)diboron (1.2 eq), Intermediate Cn (1.0 eq), 1,1-bis(diphenylphosphino)-ferrocene dichloropalladium (II) ($PdCl_2$(dppf)) (0.015 eq), and potassium acetate (KOAc) (3.0 eq) in anhydrous 1,4-dioxane (0.3 M) was stirred at 110° C. for 8 hours under nitrogen atmosphere. After cooling to room temperature, the solvent was then removed under reduced pressure, and the residue was purified via column chromatography to obtain a pale yellow solid product.

The pale yellow solid product was identified by FD-MS analysis. The chemical structures, yields, formulae, and mass analyzed by FD-MS of Intermediates Cn-B were listed in Table 3-2.

TABLE 3-2

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass ($M^+$) |
| 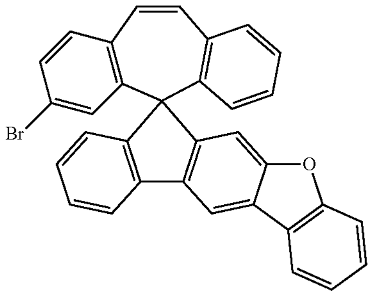 Intermediate C1 | 95 | 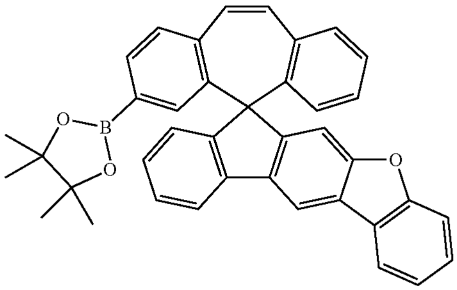 Intermediate C1-B | 98 | $C_{39}H_{31}BO_3$/ 558.47 |
| 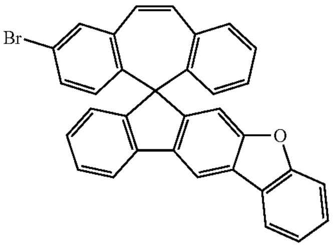 Intermediate C2 | 91 | 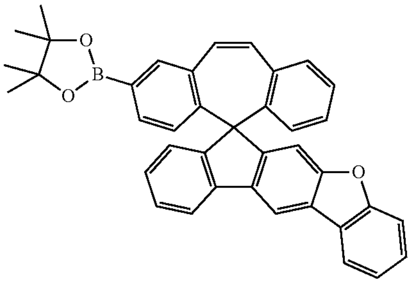 Intermediate C2-B | 98 | $C_{39}H_{31}BO_3$/ 558.47 |
| 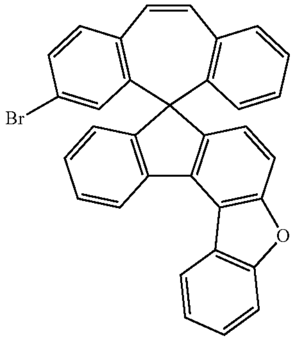 Intermediate C4 | 87 | 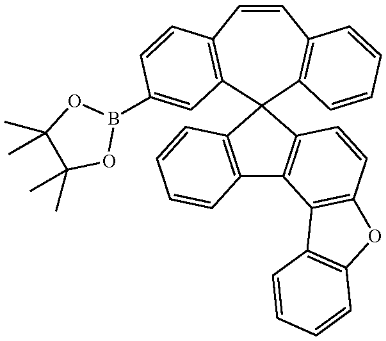 Intermediate C4-B | 93 | $C_{39}H_{31}BO_3$/ 558.47 |
| 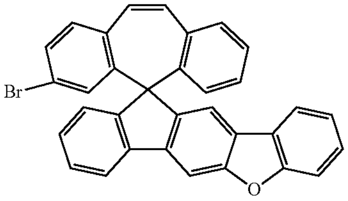 Intermediate C5 | 80 | 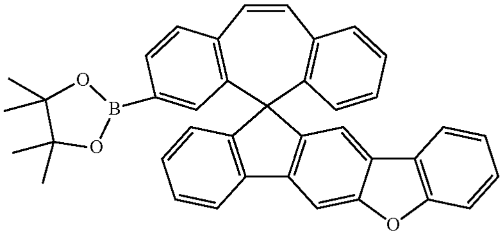 Intermediate C5-B | 90 | $C_{39}H_{31}BO_3$/ 558.47 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass ($M^+$) |
| 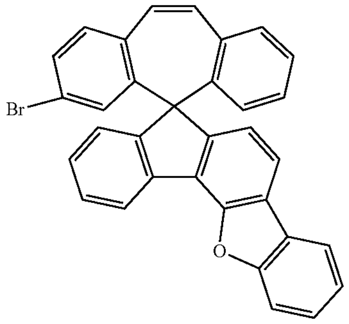 Intermediate C6 | 95 | 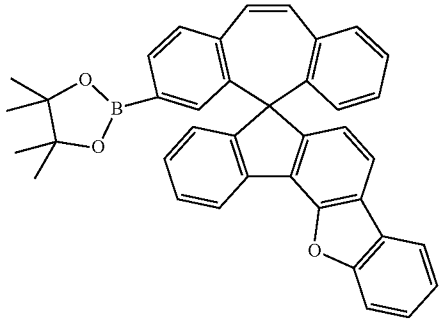 Intermediate C6-B | 90 | $C_{39}H_{31}BO_3$/ 558.47 |
| 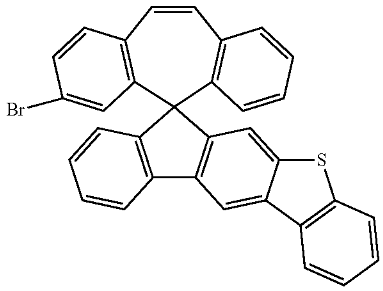 Intermediate C7 | 93 | 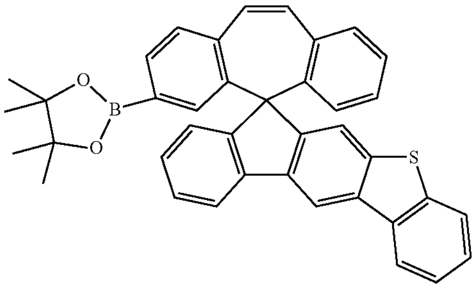 Intermediate C7-B | 91 | $C_{39}H_{31}BO_2S$/ 574.54 |
| 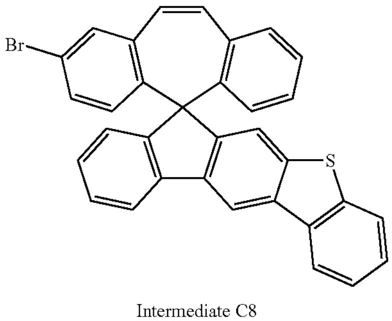 Intermediate C8 | 85 | 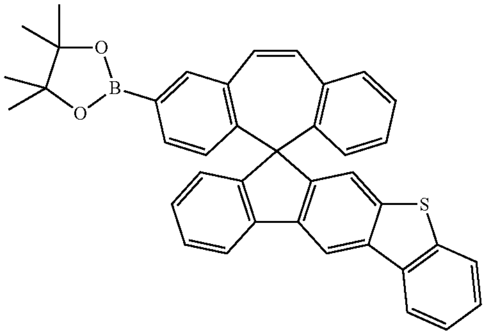 Intermediate C8-B | 91 | $C_{39}H_{31}BO_2S$/ 574.54 |
| 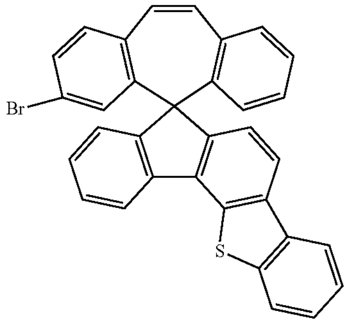 Intermediate C9 | 88 | 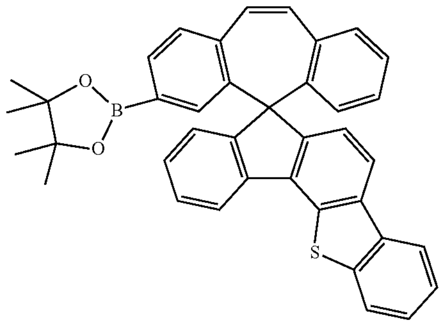 Intermediate C9-B | 92 | $C_{39}H_{31}BO_2S$/ 574.54 |

Modifications of Intermediate Cn-B

In addition to the Intermediate Cn-B, one person skilled in the art can adopt any one of foresaid Intermediates Cn to undergo a Miyaura borylation reaction to successfully synthesize other desired intermediate as follows.

Intermediate C10-B

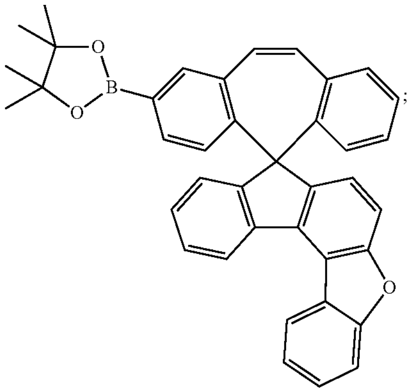

;

Intermediate C16-B

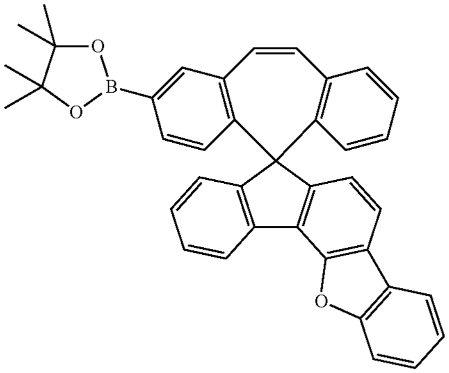

;

-continued

Intermediate C21-B

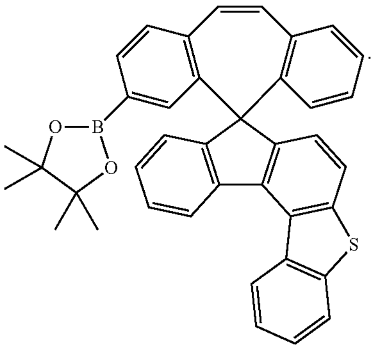

.

Synthesis of Novel Compounds

Each of the foresaid Intermediates Cn and Cn-B could be reacted with various reactants to synthesize various claimed novel compounds. The general synthesis pathway of the claimed novel compound was summarized in Scheme I. In the following Scheme I, "Reactant B" may be any one of Reactants B1 to B25 as listed in Table 4, and "Intermediate C" may be any one of the foresaid Intermediates Cn and Cn-B or the like. The compounds were each synthesized by the following steps.

Scheme I

Pd(OAc)$_2$,
P(Cy$_2$)(2-biPh)

Reactant Bn + Intermediate C → Claimed Compound

K$_2$CO$_3$,
toluene/EtOH

TABLE 4
| chemical structure and CAS No. of Reactants B1 to B25. | | | | |
|---|---|---|---|---|
| Reactant No. | Reactant B1 | Reactant B2 | Reactant B3 | Reactant B4 |
| Chemical Structure | 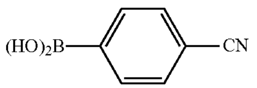 [SMILES: N#Cc1ccc(B(O)O)cc1] | 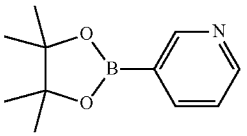 | 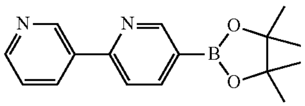 [SMILES: CC1(C)OB(c2ccc(-c3cccnc3)nc2)OC1(C)C] | 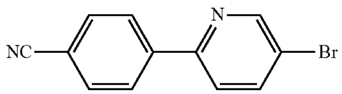 |
| CAS No. | [126747-14-6] | [329214-79-1] | [1260106-29-3] | [916653-46-8] |
| Reactant No. | Reactant B5 | Reactant B6 | Reactant B7 | Reactant B8 |
| Chemical Structure | 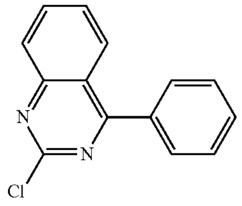 [SMILES: Clc1nc(-c2ccccc2)c2ccccc2n1] | 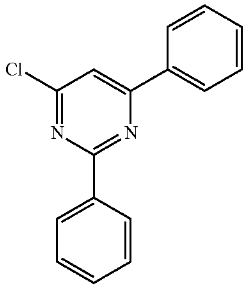 [SMILES: Clc1cc(-c2ccccc2)nc(-c2ccccc2)n1] | 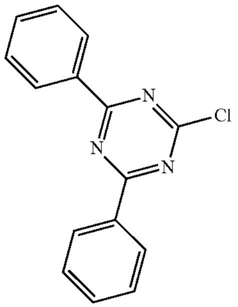 [SMILES: Clc1nc(-c2ccccc2)nc(-c2ccccc2)n1] | 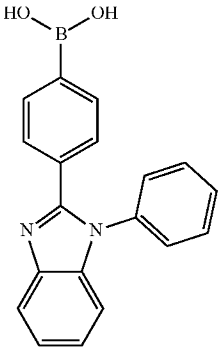 [SMILES: OB(O)c1ccc(-c2nc3ccccc3n2-c2ccccc2)cc1] |
| CAS No. | [29874-83-7] | [29509-91-9] | [3842-55-5] | [952514-79-3] |
| Reactant No. | Reactant B9 | Reactant B10 | Reactant B11 | Reactant B12 |
| Chemical Structure | 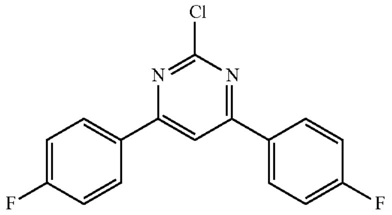 [SMILES: Fc1ccc(-c2cc(-c3ccc(F)cc3)nc(Cl)n2)cc1] | 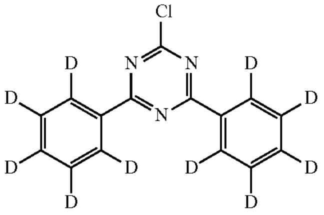 [SMILES: [2H]c1c([2H])c([2H])c(-c2nc(Cl)nc(-c3c([2H])c([2H])c([2H])c([2H])c3[2H])n2)c([2H])c1[2H]] | 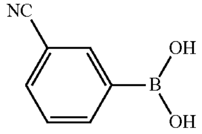 [SMILES: N#Cc1cccc(B(O)O)c1] | 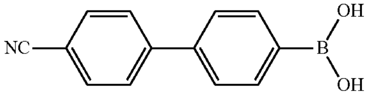 |

TABLE 4-continued
chemical structure and CAS No. of Reactants B1 to B25.
| | | | | |
|---|---|---|---|---|
| CAS No. | [1588407-97-9] | [1300115-09-6] | [150255-96-2] | [406482-73-3] |
| Reactant No. Chemical Structure | Reactant B13 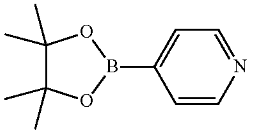 | Reactant B14 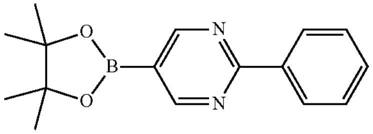 [SMILES: CC1(C)OB(c2cnc(-c3ccccc3)nc2)OC1(C)C] | Reactant B15 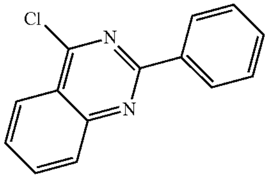 [SMILES: Clc1nc(-c2ccccc2)nc2ccccc12] | Reactant B16 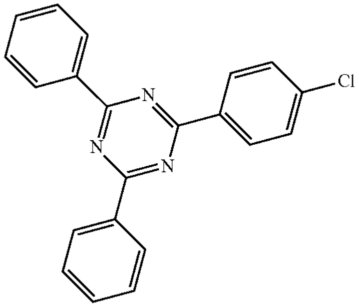 [SMILES: Clc1ccc(-c2nc(-c3ccccc3)nc(-c3ccccc3)n2)cc1] |
| CAS No. | [181219-01-2] | [1319255-85-0] | [6484-25-9] | [3114-52-1] |
| Reactant No. | Reactant B17 | Reactant B18 | Reactant B19 | Reactant B20 |
| Chemical Structure | 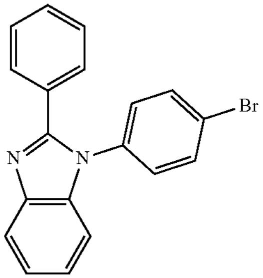 [SMILES: Brc1ccc(-n2c(-c3ccccc3)nc3ccccc32)cc1] | 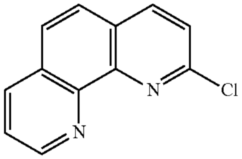 [SMILES: Clc1ccc2ccc3cccnc3c2n1] | 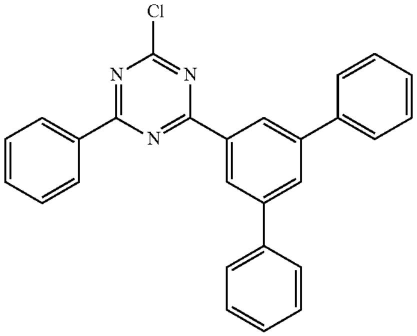 [SMILES: Clc1nc(-c2ccccc2)nc(-c2cc(-c3ccccc3)cc(-c3ccccc3)c2)n1] | 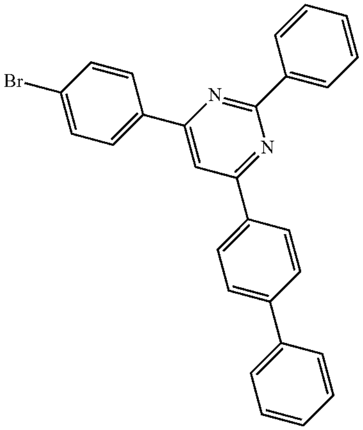 [SMILES: Brc1ccc(-c2cc(-c3ccc(-c4ccccc4)cc3)nc(-c3ccccc3)n2)cc1] |
| CAS No. | [867044-33-5] | [7089-68-1] | [1616231-57-2] | [1421599-34-9] |
| Reactant No. | Reactant B21 | Reactant B22 | Reactant B23 | Reactant B24 |

TABLE 4-continued
| chemical structure and CAS No. of Reactants B1 to B25. | | | | |
| --- | --- | --- | --- | --- |
| Chemical Structure | 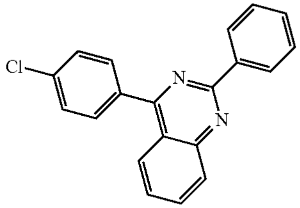 [SMILES: Clc1ccc(-c2nc(-c3ccccc3)nc3ccccc23)cc1] | 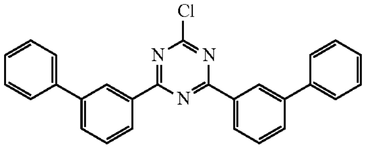 [SMILES: Clc1nc(-c2cccc(-c3ccccc3)c2)nc(-c2cccc(-c3ccccc3)c2)n1] | 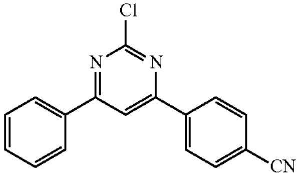 [SMILES: N#Cc1ccc(-c2cc(-c3ccccc3)nc(Cl)n2)cc1] | 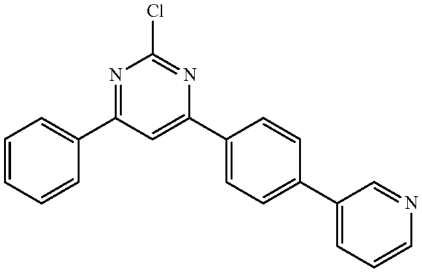 [SMILES: Clc1nc(-c2ccccc2)cc(-c2ccc(-c3cccnc3)cc2)n1] |
| CAS No. | [99682-89-0] | | | |
| Reactant No. | Reactant B25 | | | |
| Chemical Structure | 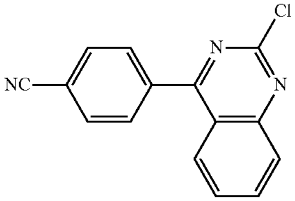 [SMILES: N#Cc1ccc(-c2nc(Cl)nc3ccccc23)cc1] | | | |

A mixture of Intermediate C (1.0 eq), $Pd(OAc)_2$ (0.01 eq), $P(Cy)_2$(2-biphenyl) (0.04 eq), toluene/ethanol (0.5M, v/v=10/1), 3.0 M potassium carbonate solution, and Reactant Bn (2.1 eq) was stirred at 100° C. for 12 h under nitrogen atmosphere. After the completion of the reaction, water and toluene were added to the reaction mass. Subsequently, the organic layer was recovered by solvent extraction operation and dried over sodium sulfate. The solvent was then removed from the organic layer under reduced pressure, and the resulting residue was purified by silica gel column chromatography. The obtained residue was recrystallized with toluene to obtain white solid as the claimed novel compound.

Figure 2:
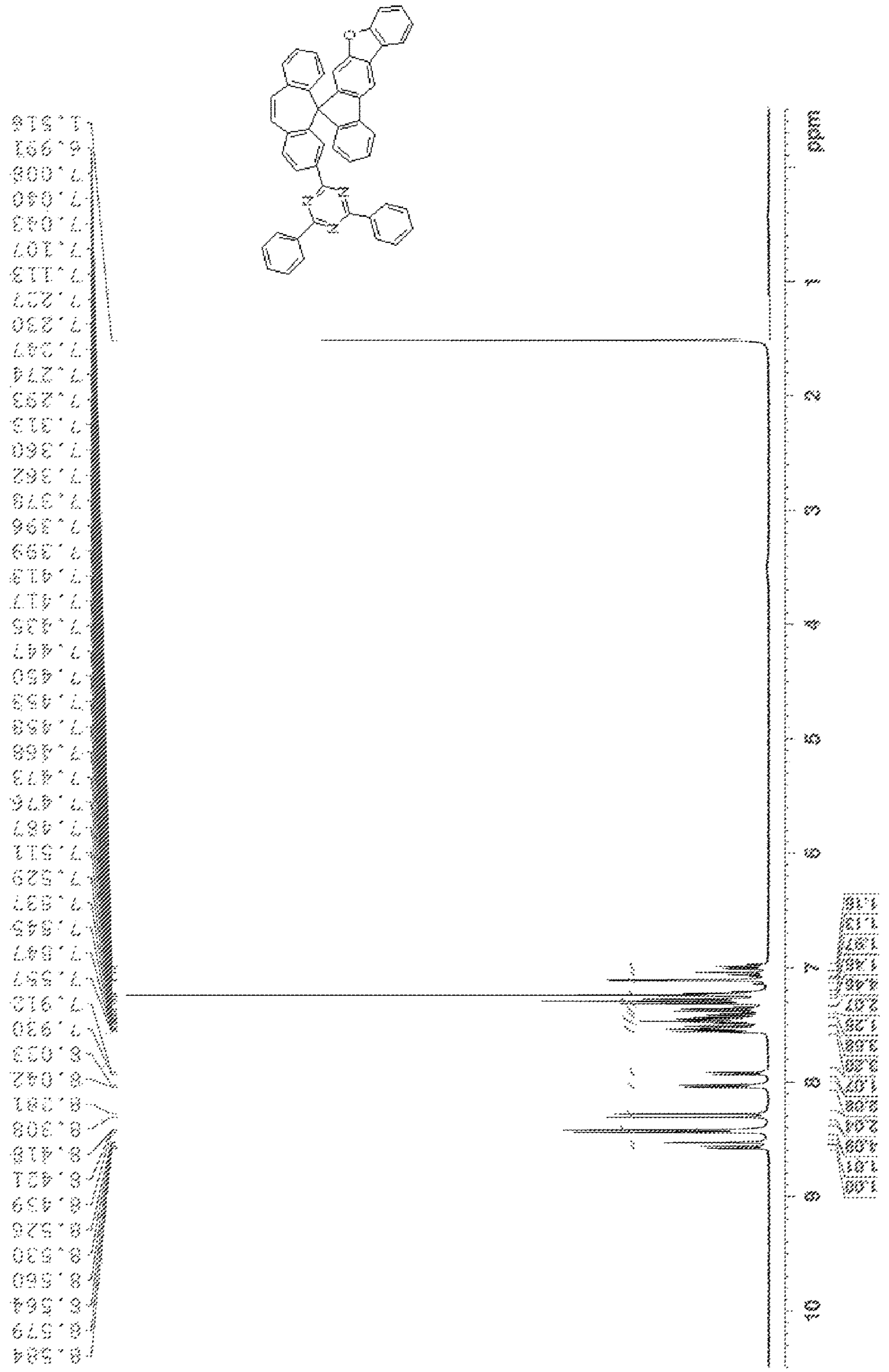
FIGS. 2 to 18 are respectively $^1H$ nuclear magnetic resonance (NMR) spectra of Compounds I to XVII.
Figure 3:
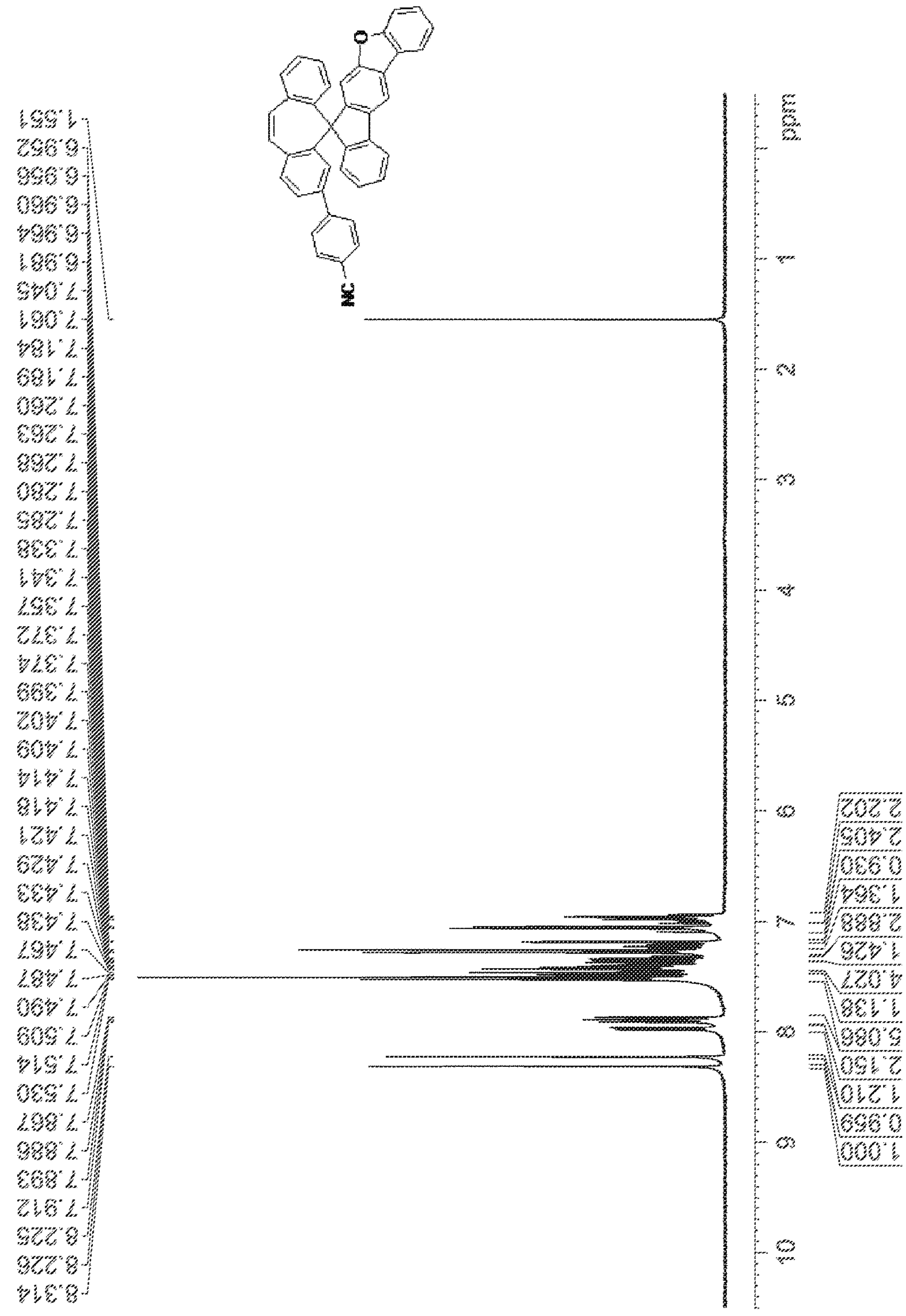
Figure 4:
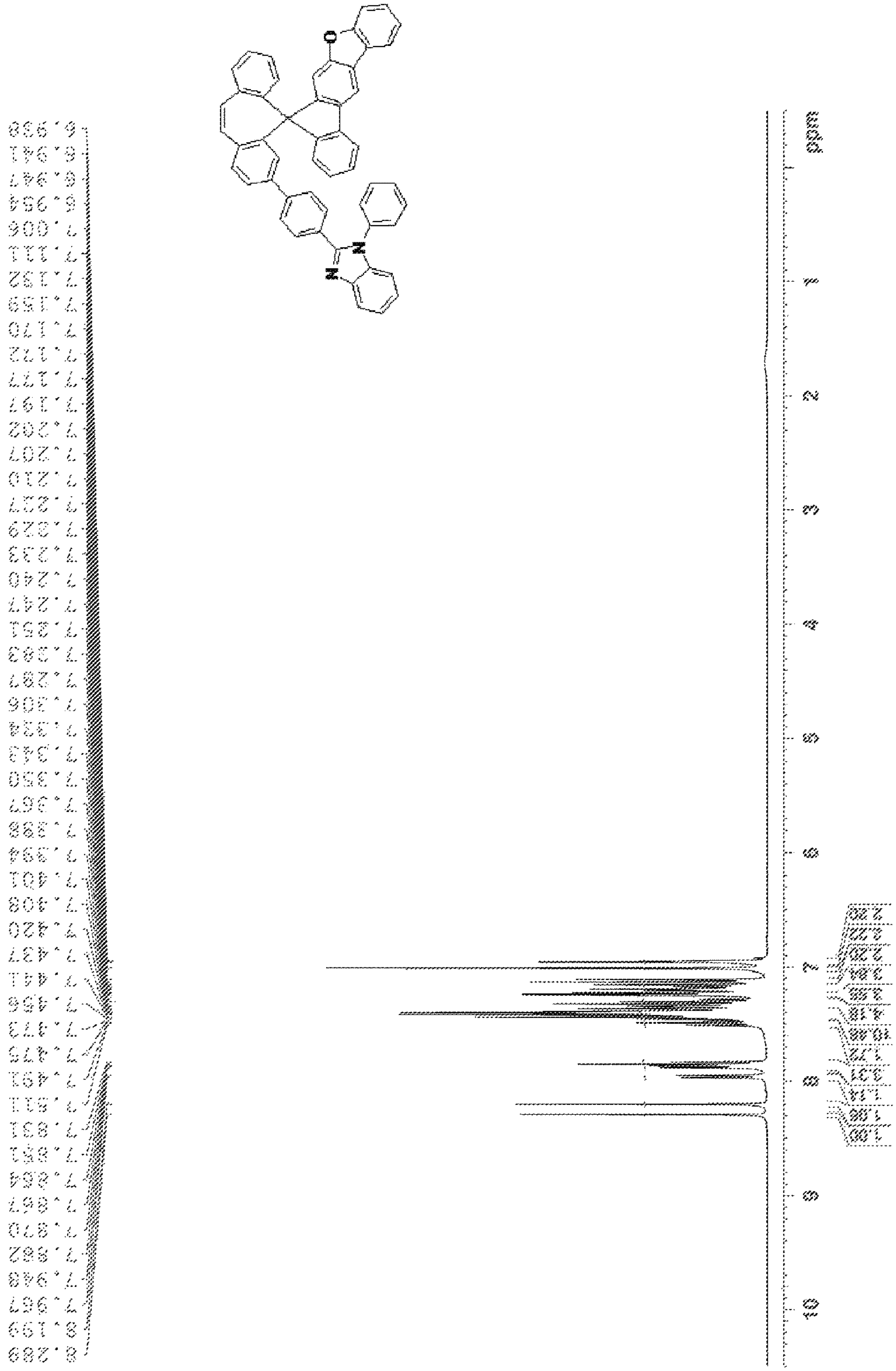
Figure 5:
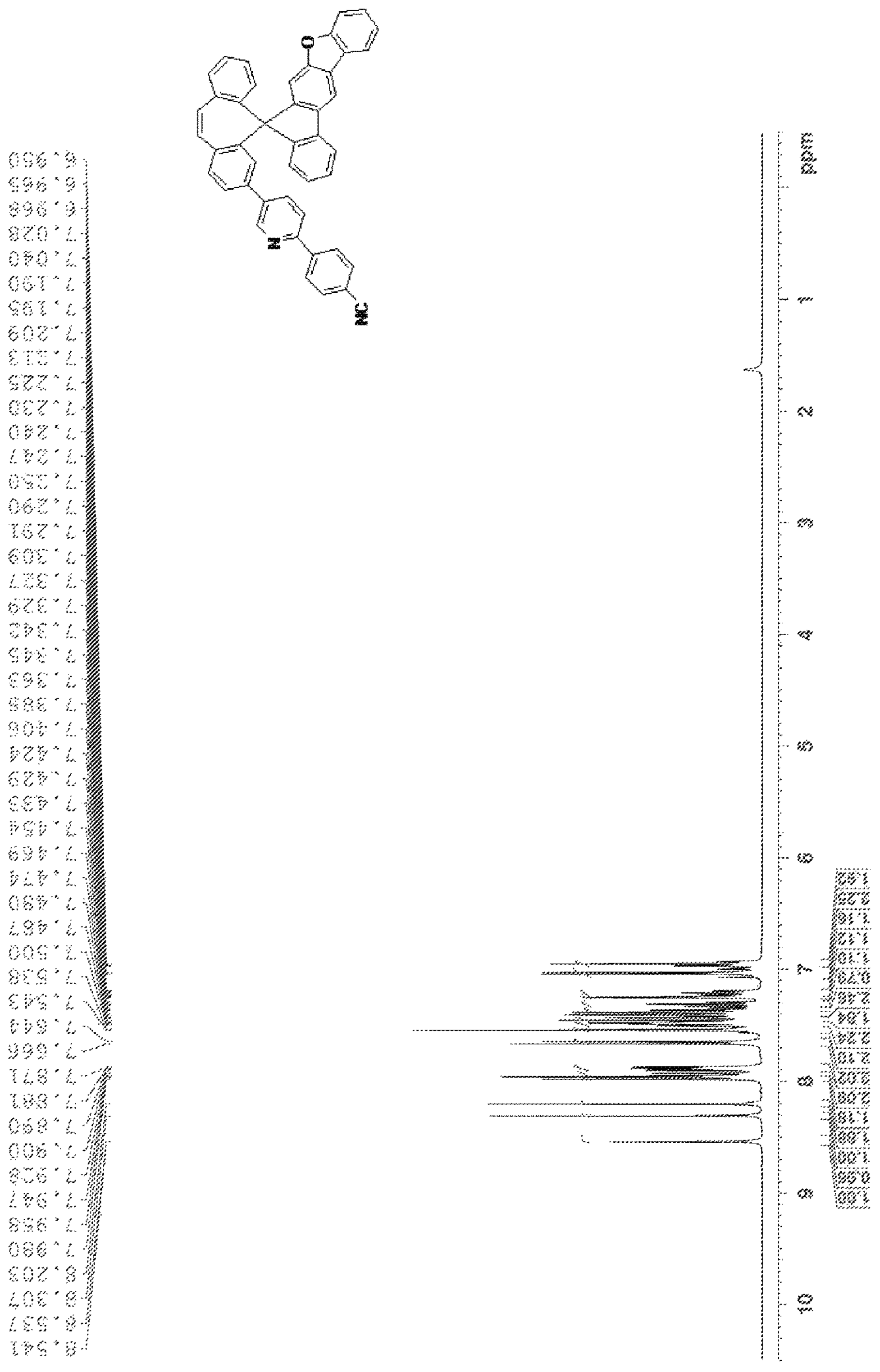
Figure 6:
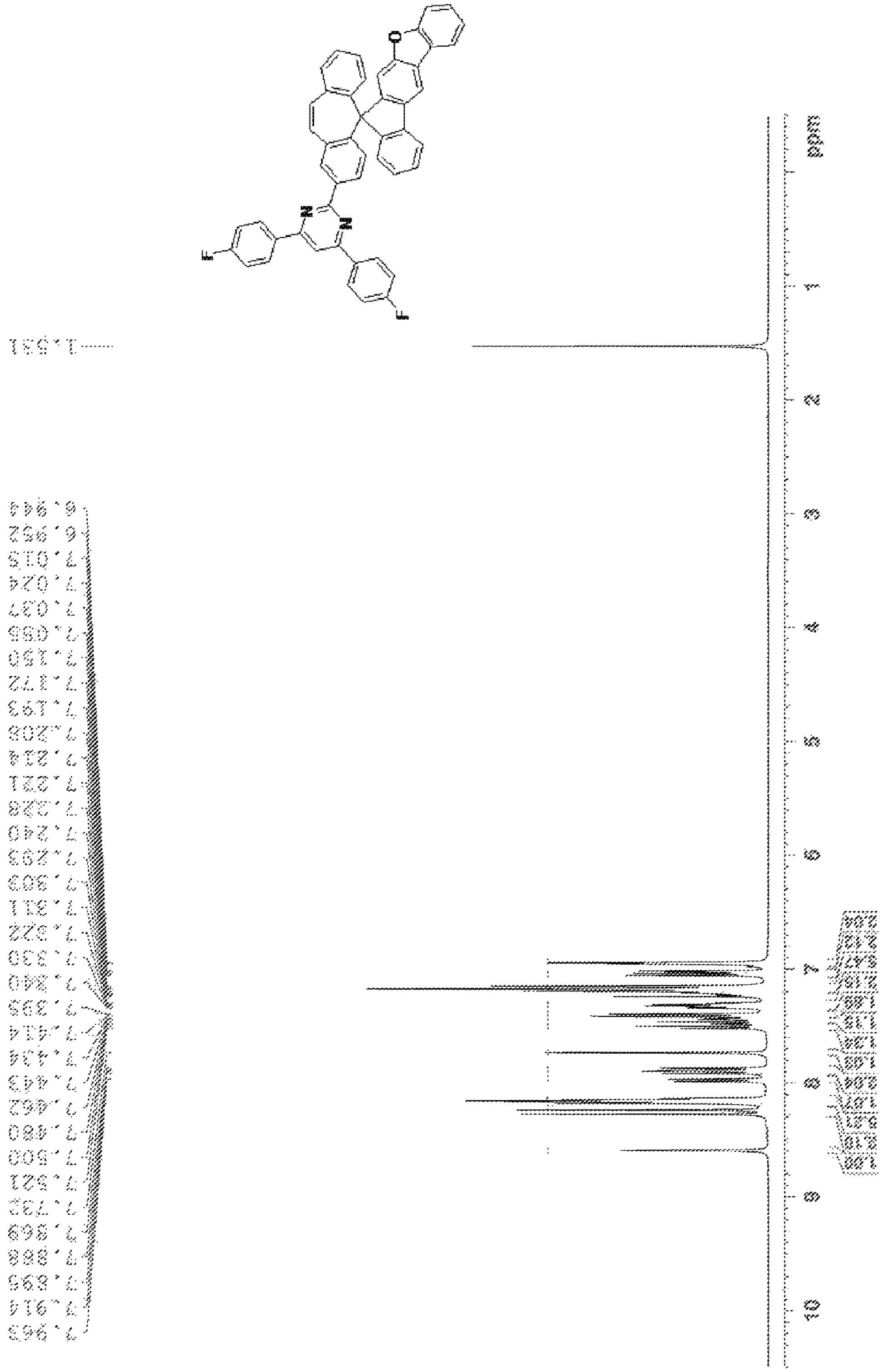
Figure 7:
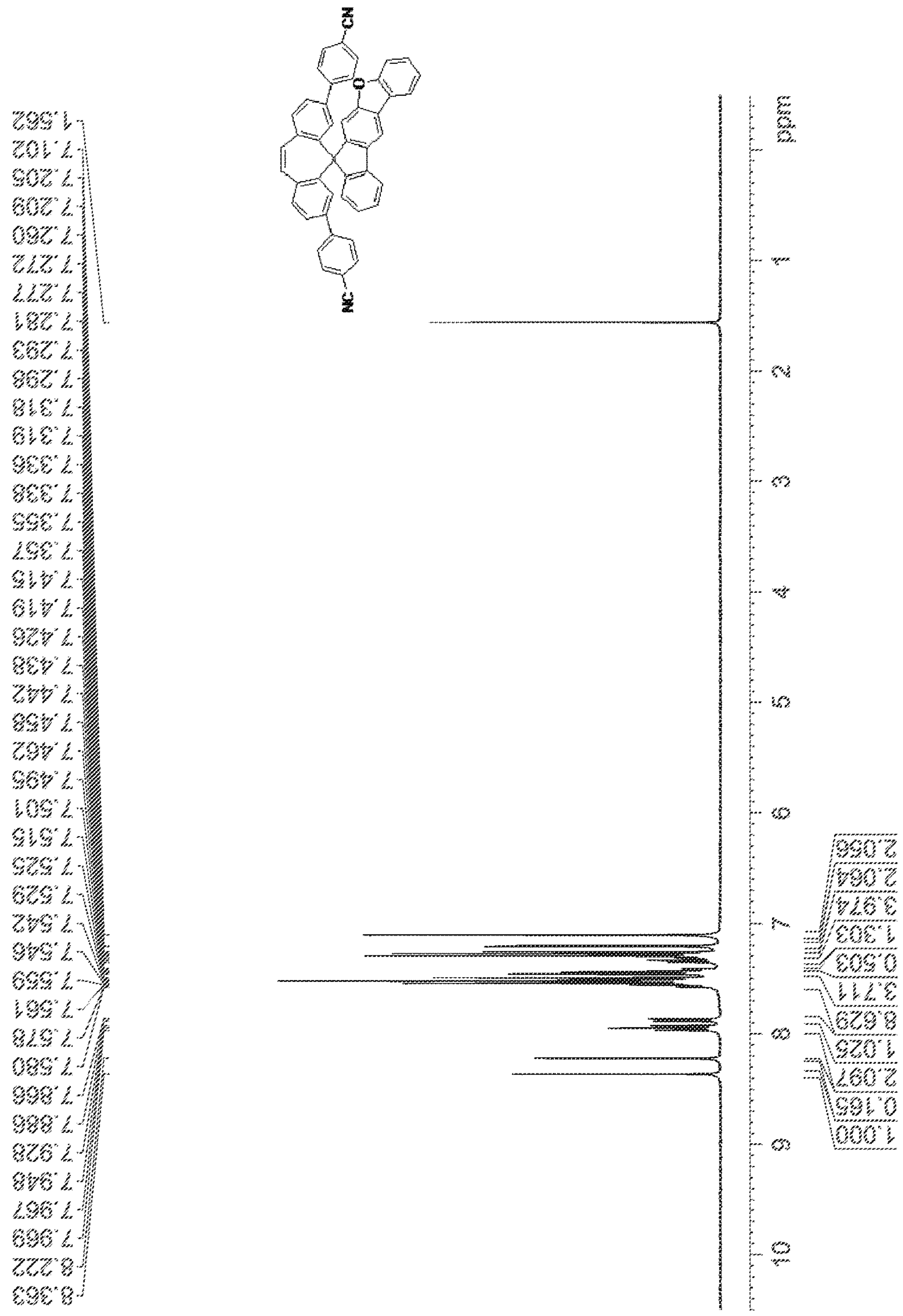
Figure 8:
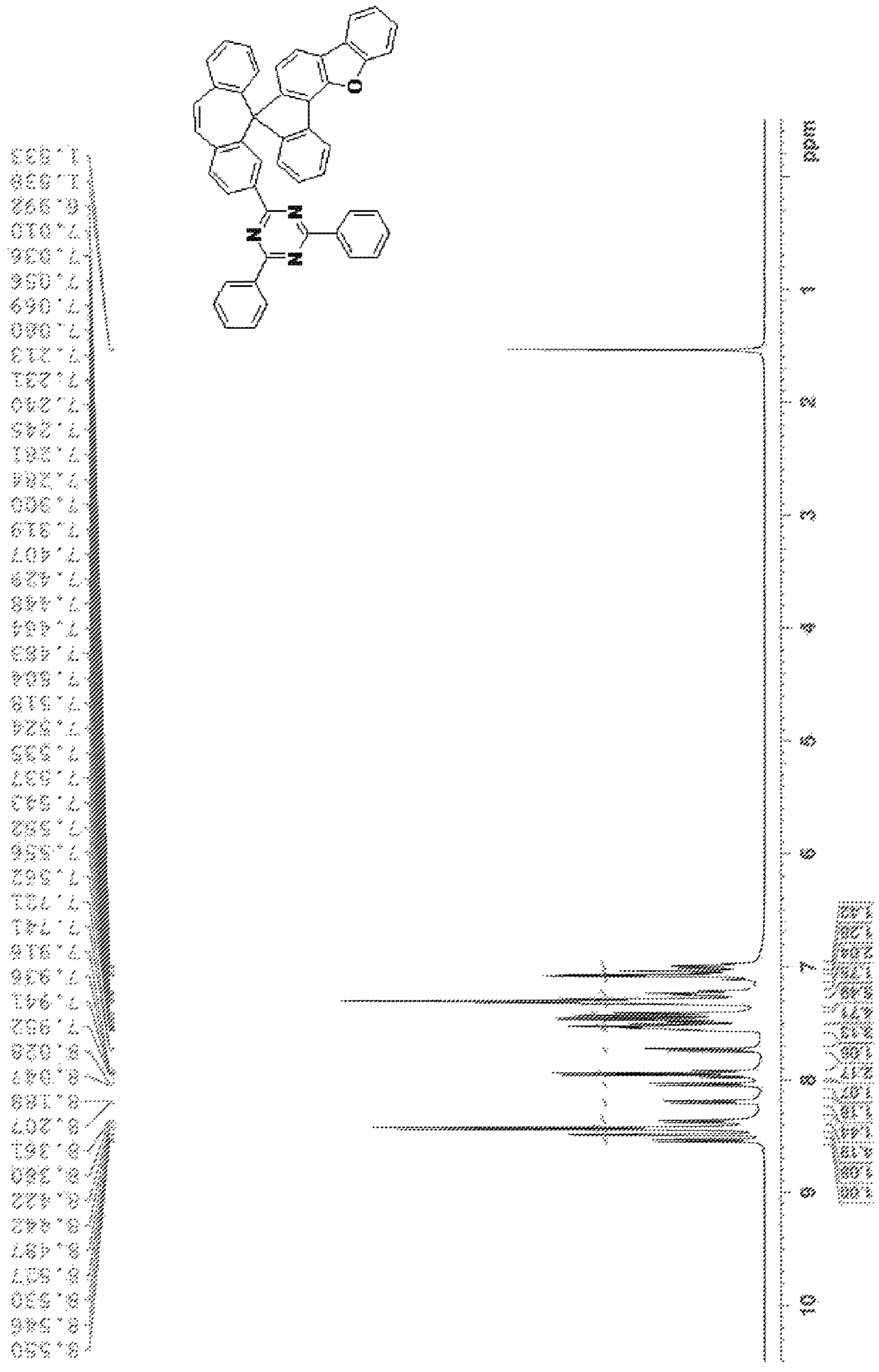
Figure 9:
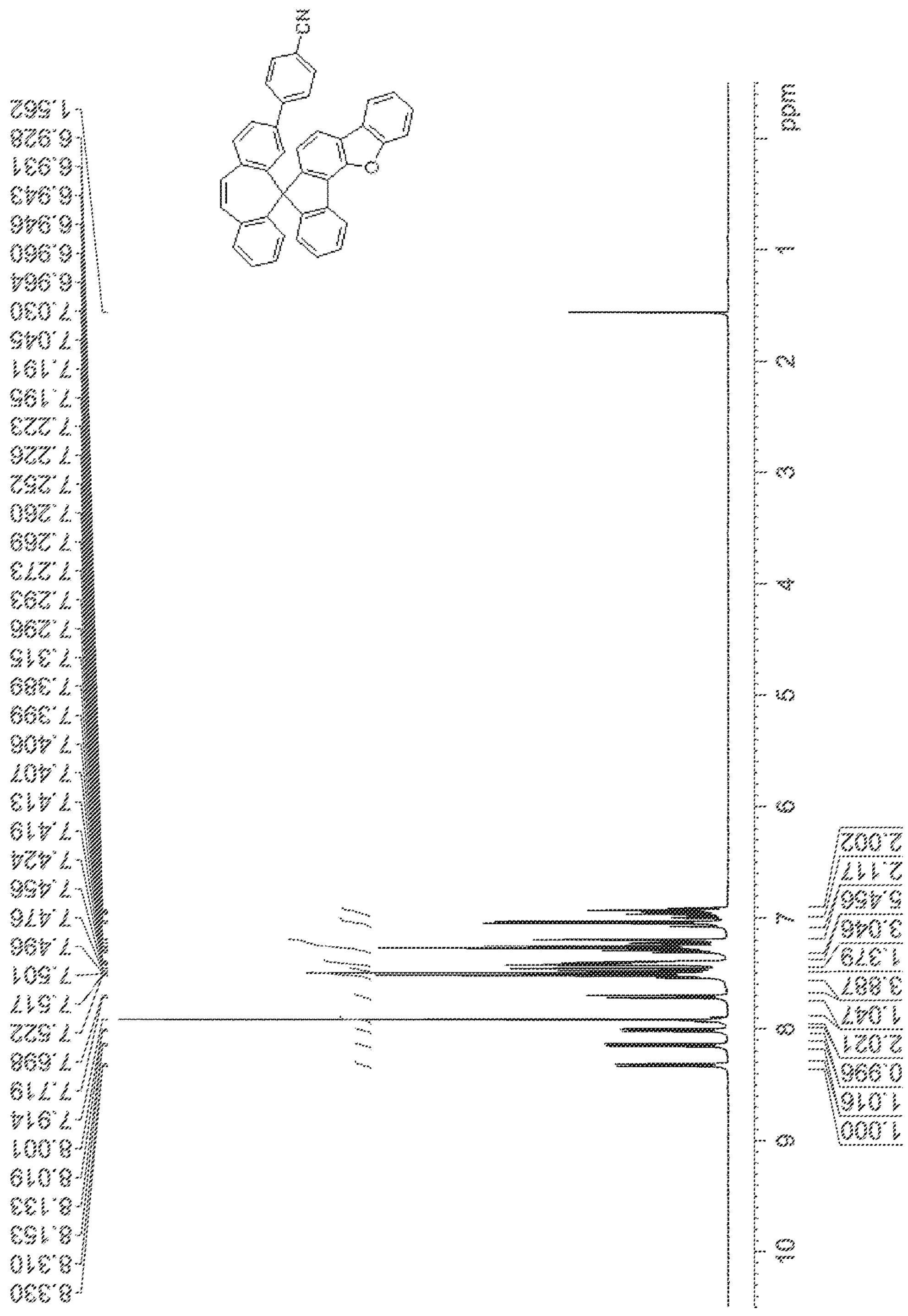
Figure 10:
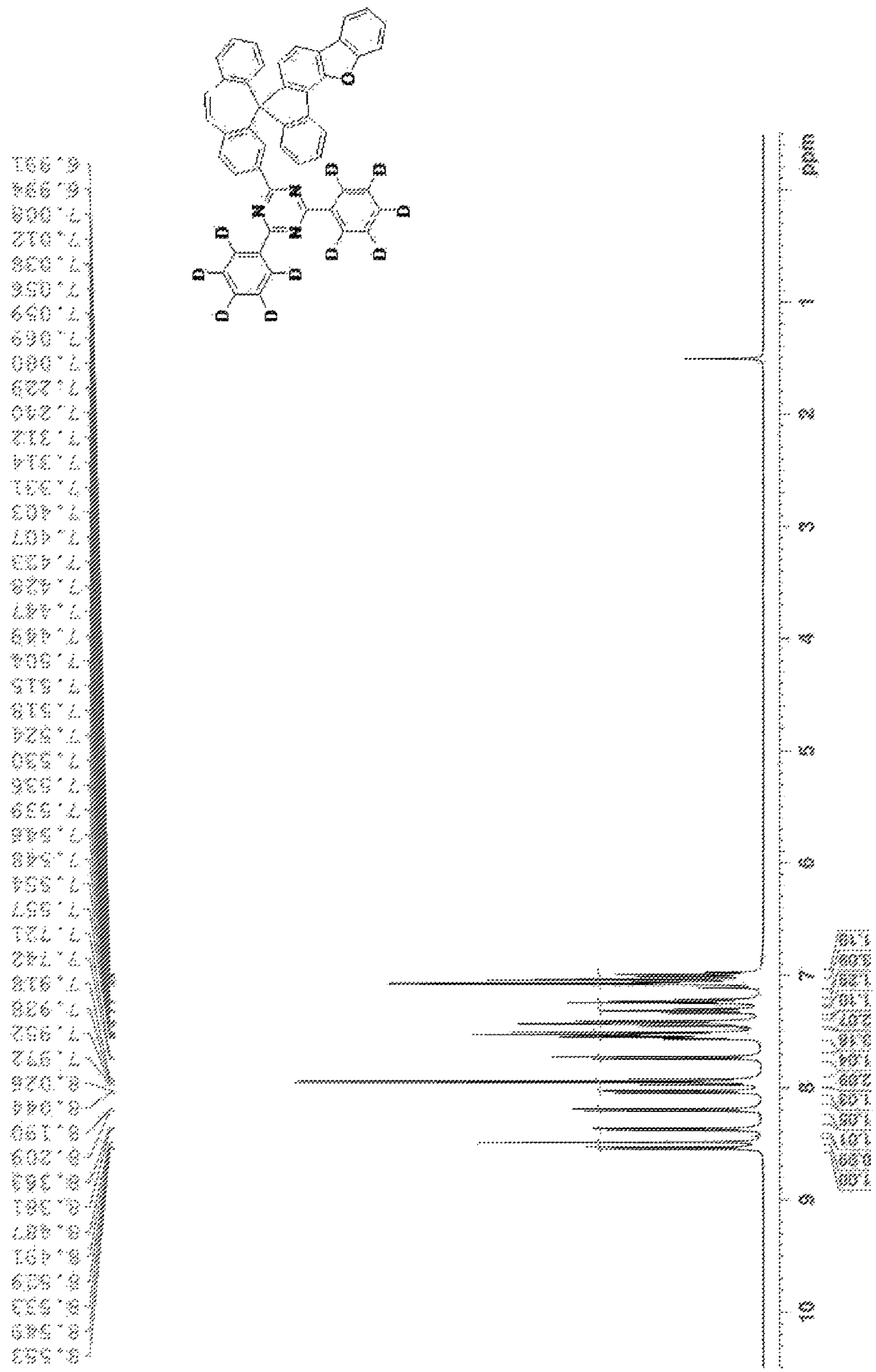
Figure 11:
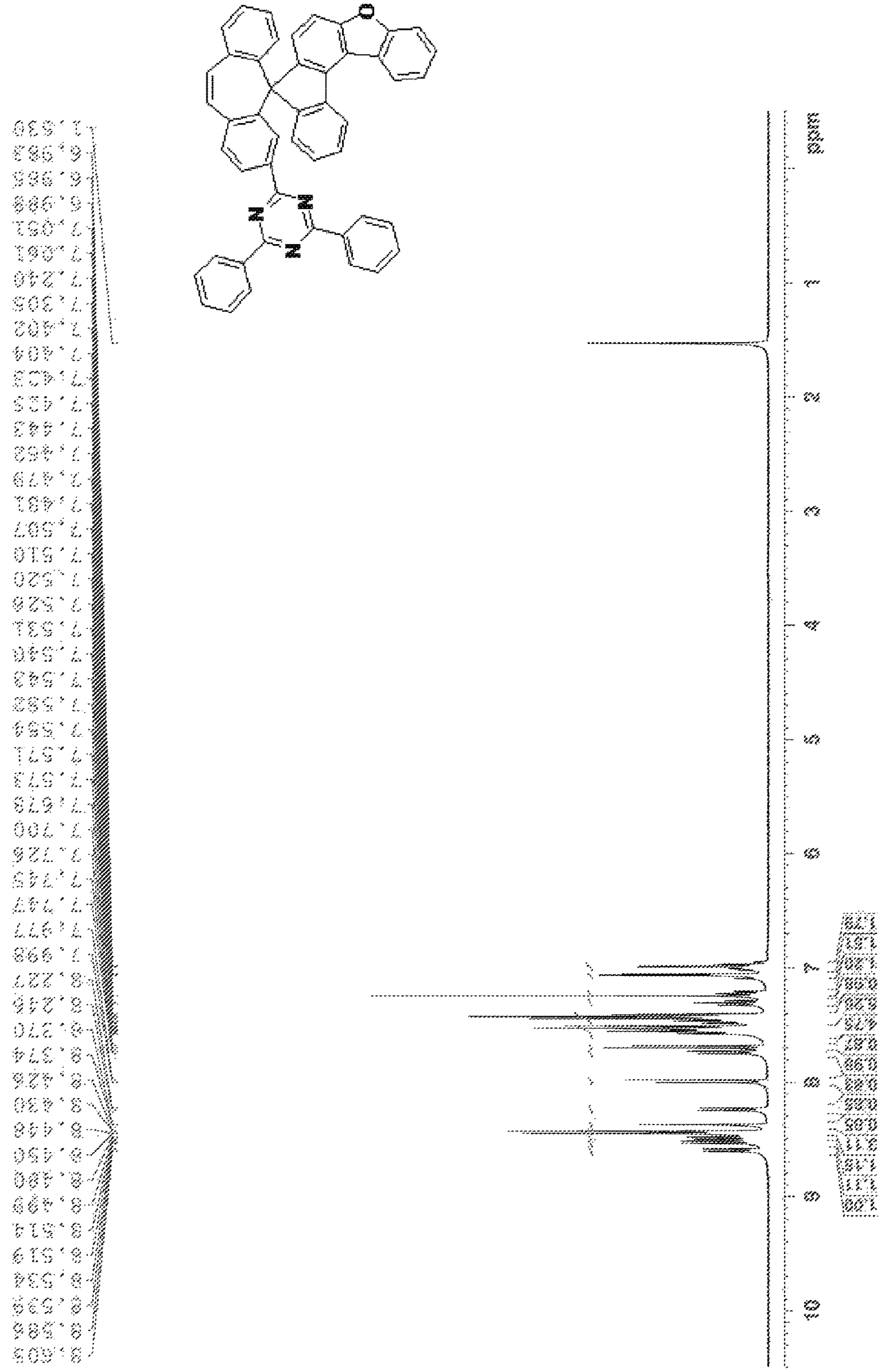
Figure 12:
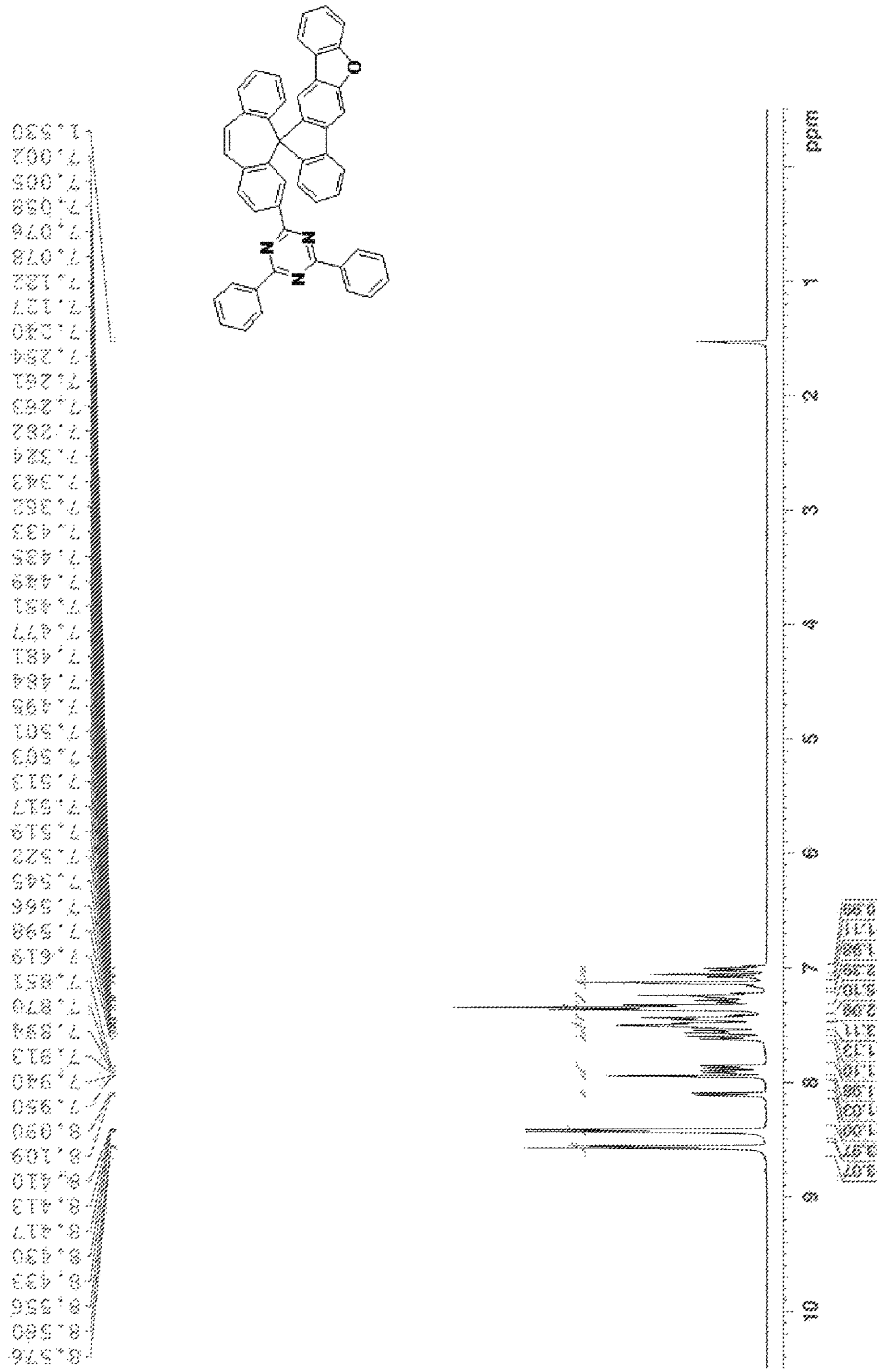
Figure 13:
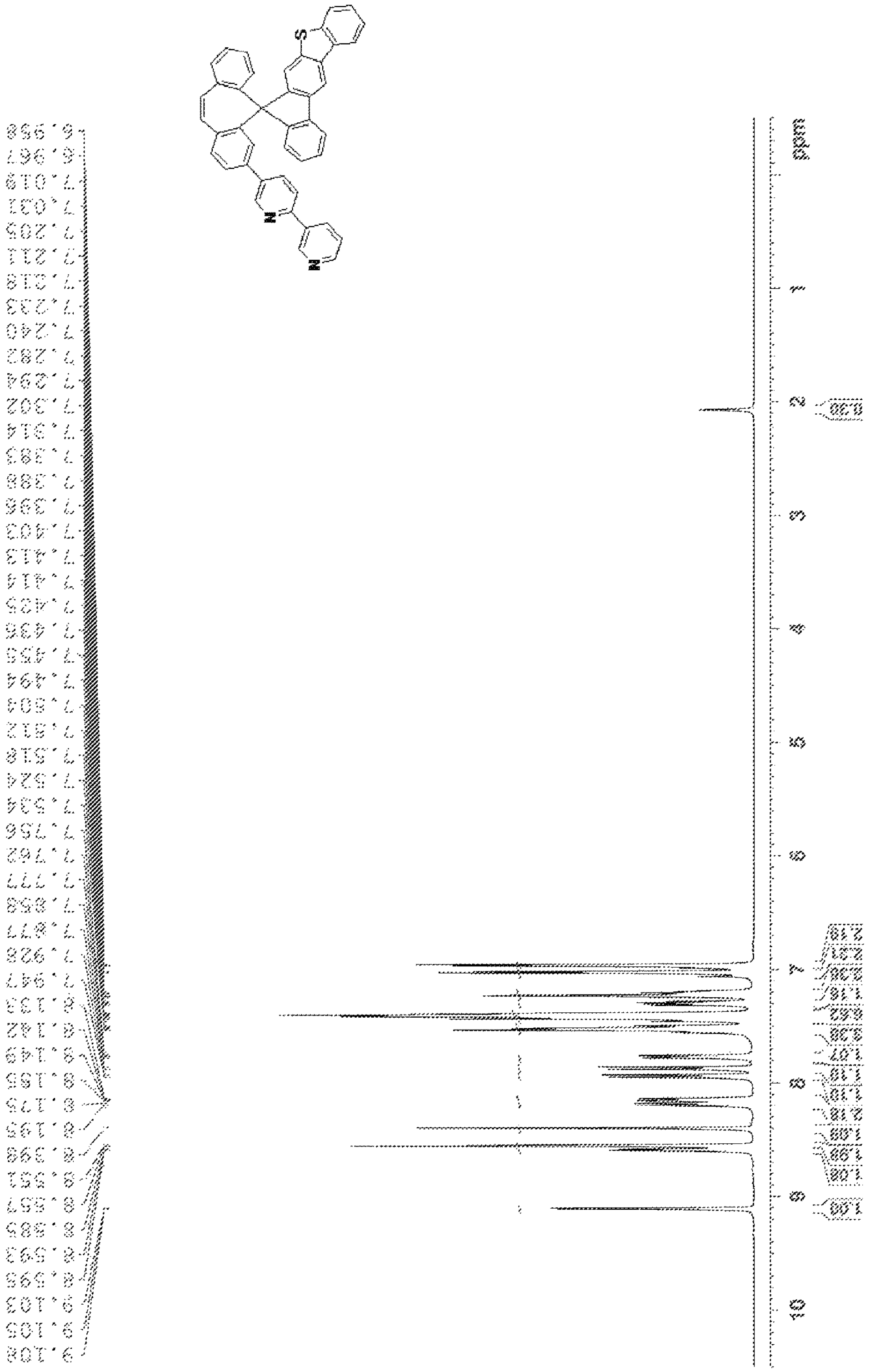
Figure 14:
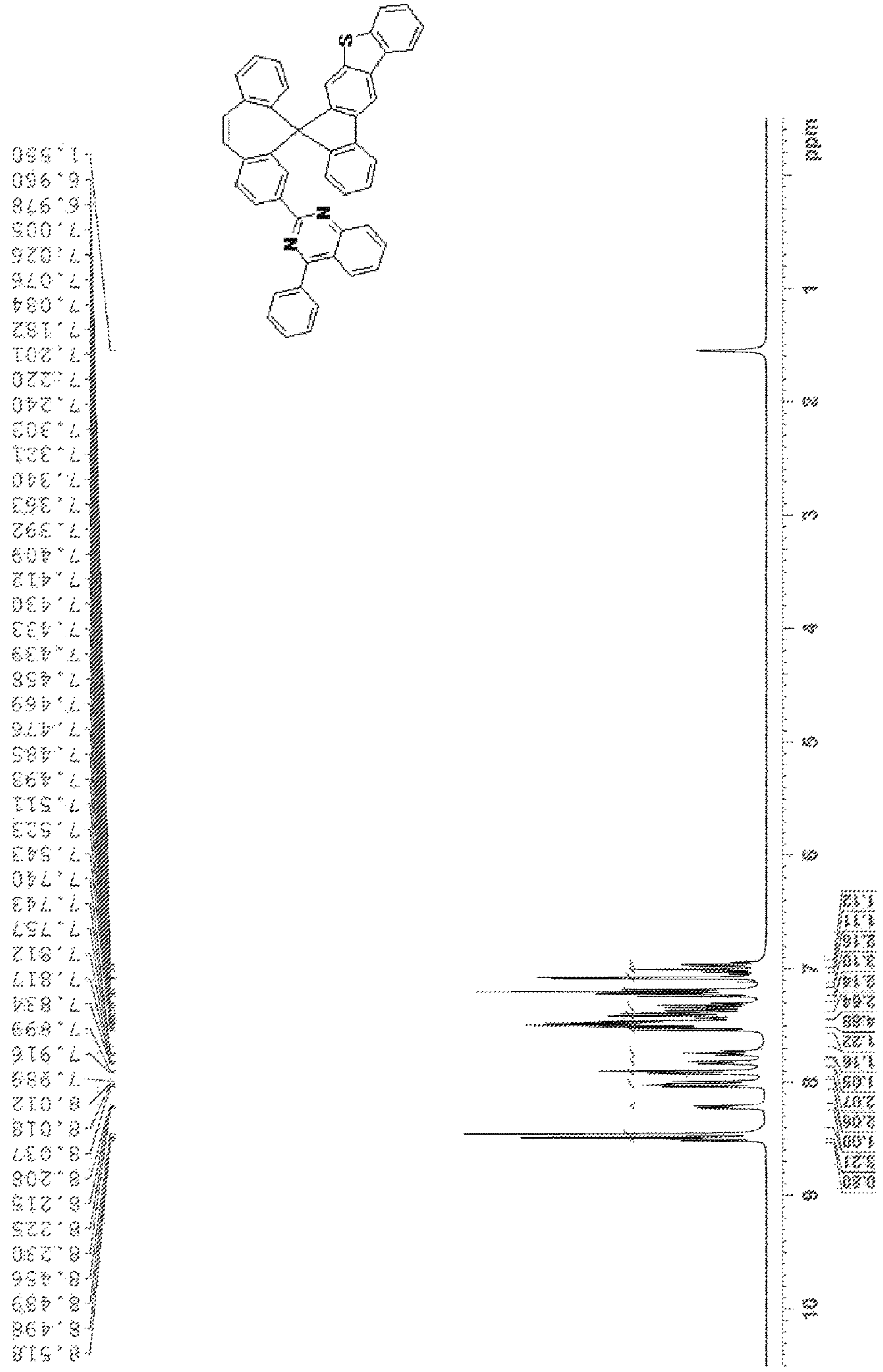
Figure 15:
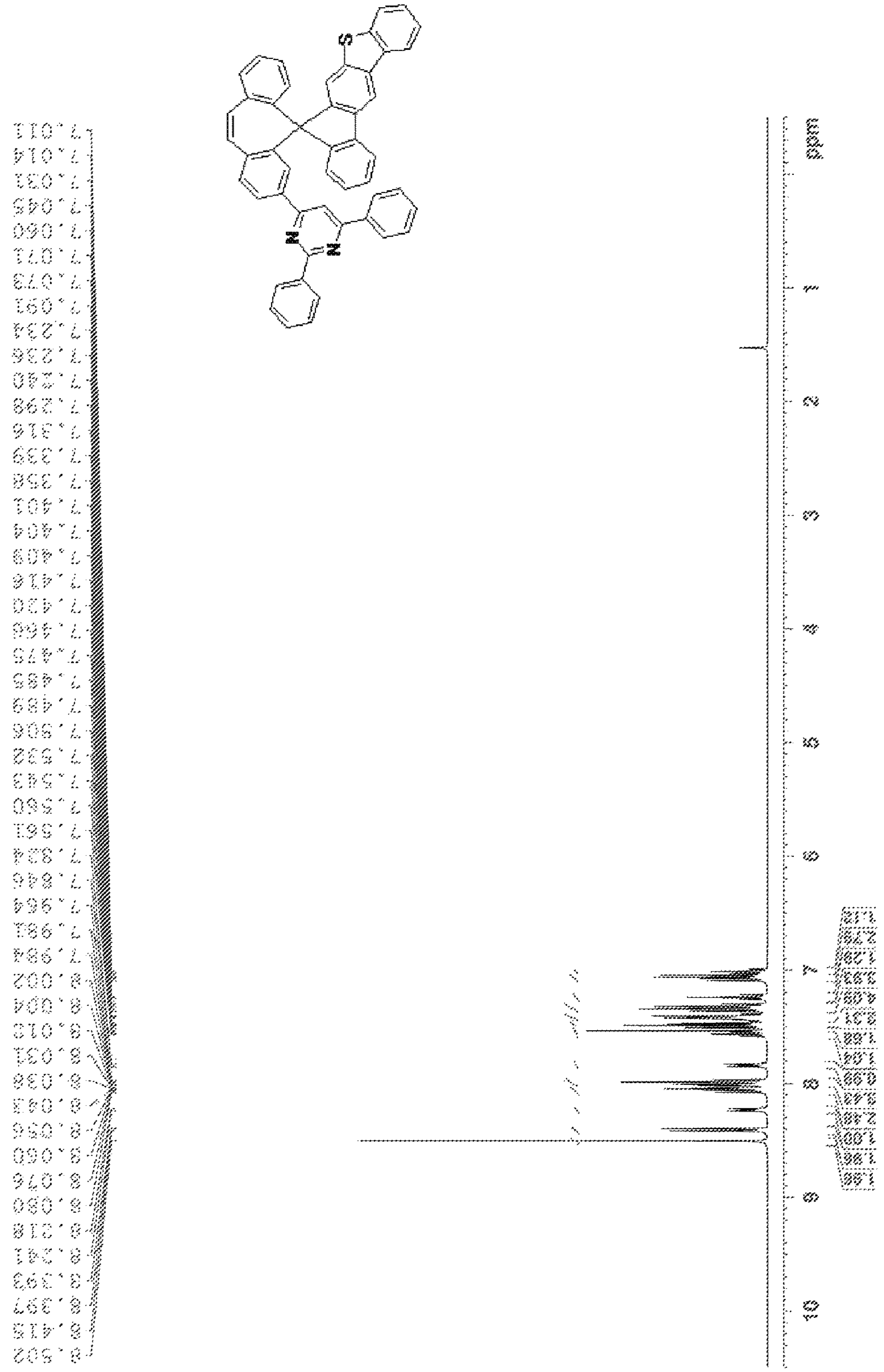
Figure 16:
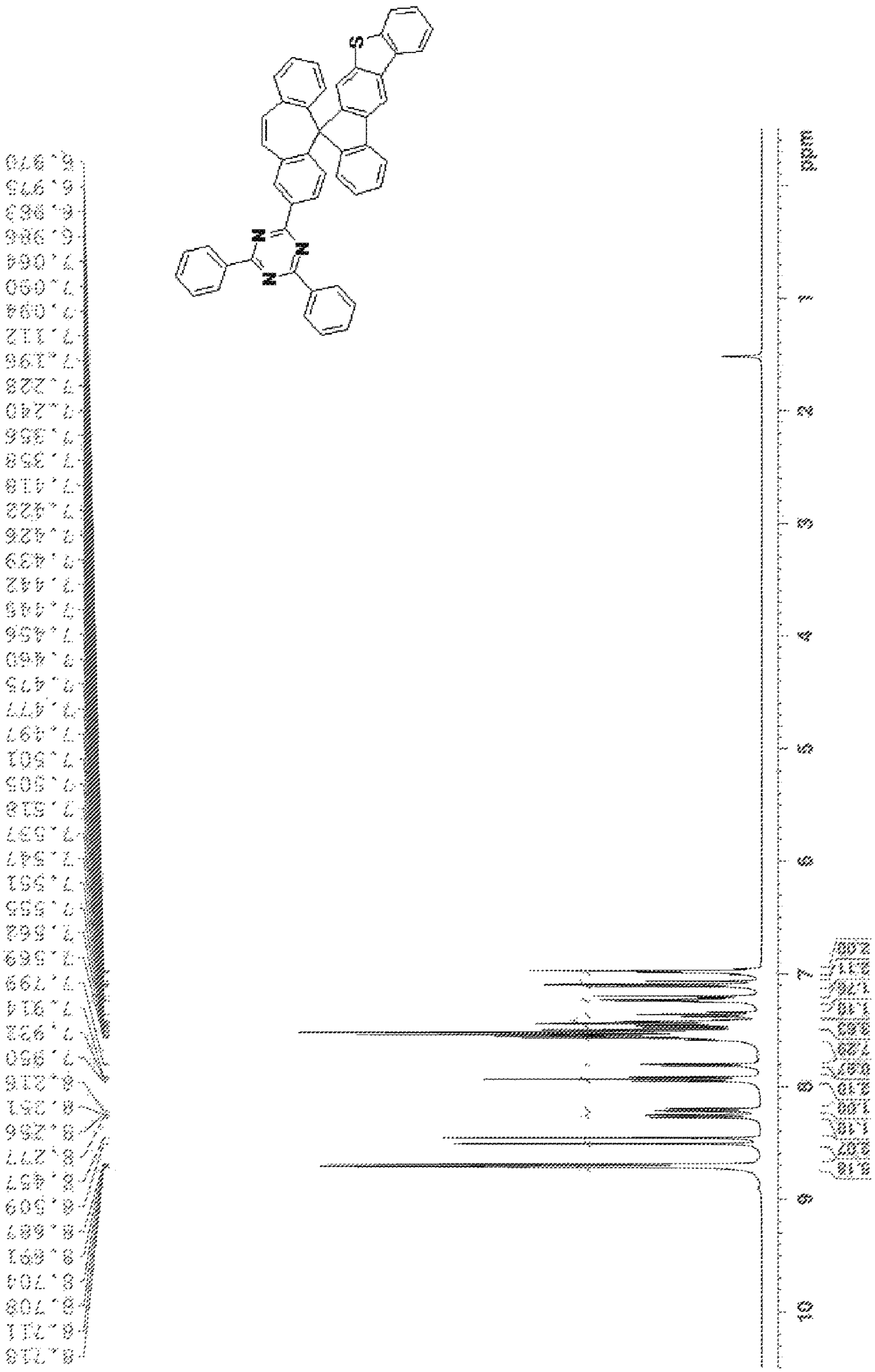
Figure 17:
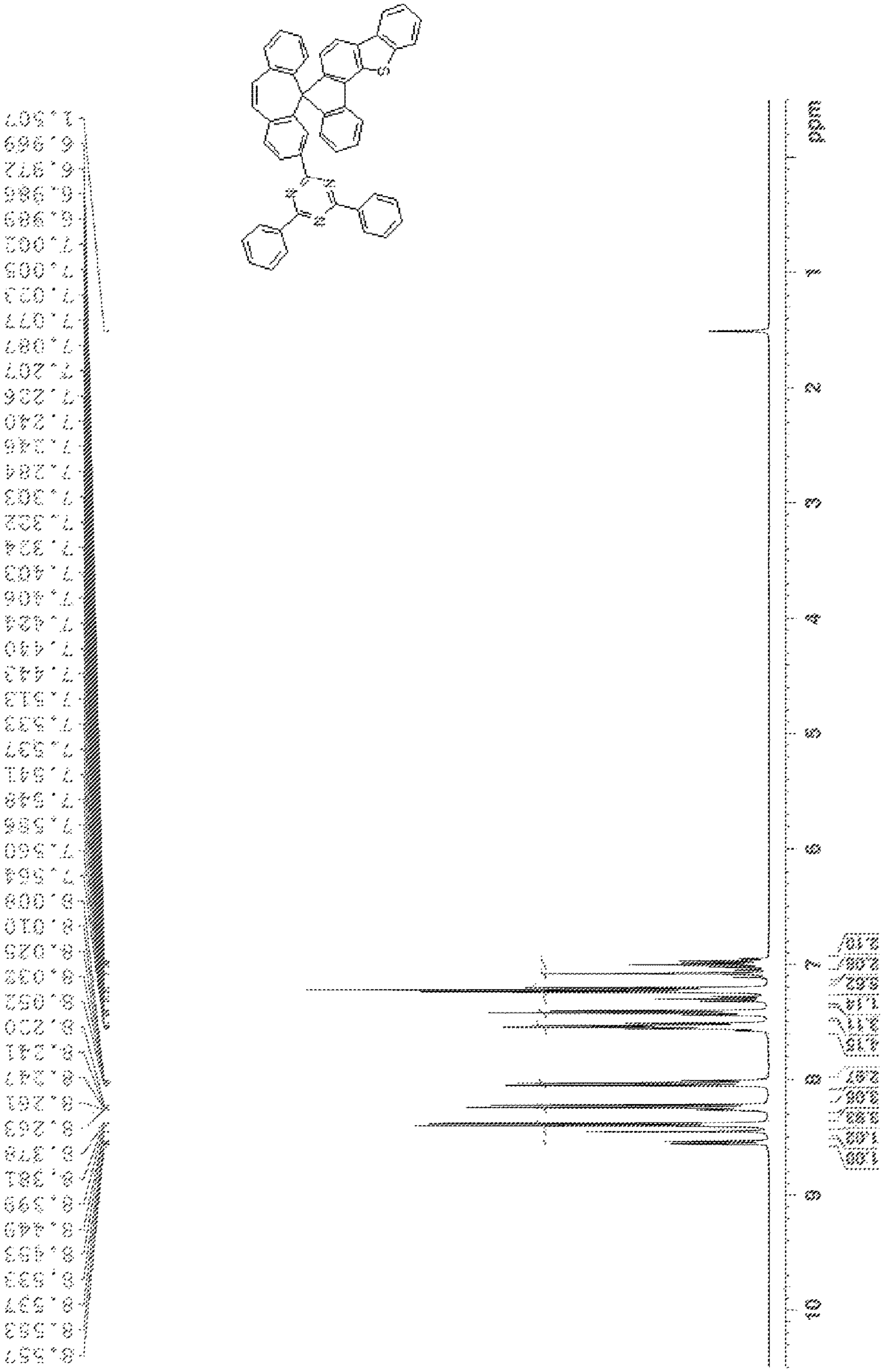
Figure 18:
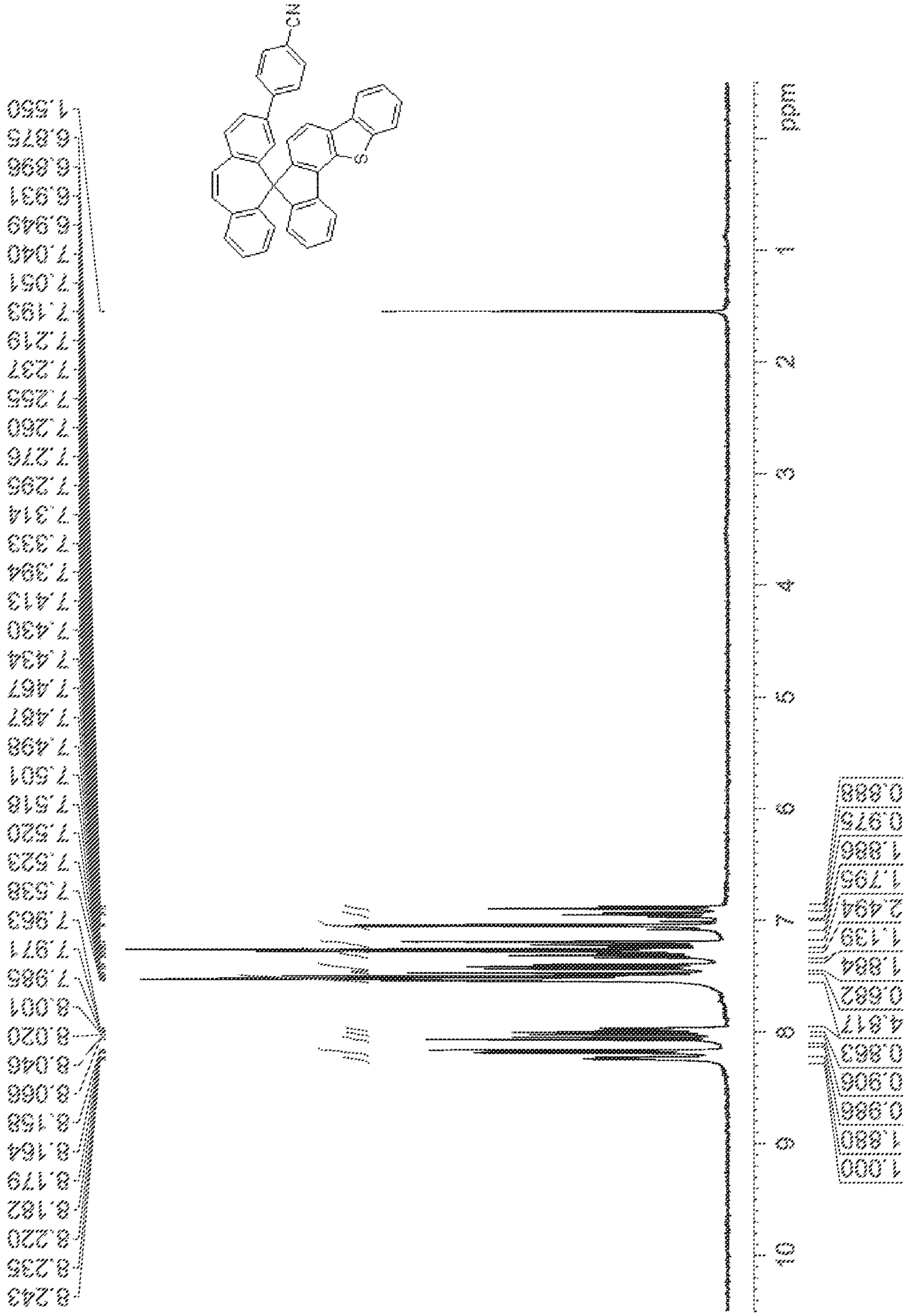

Reactant Bn and Intermediate C adopted to synthesize Compounds I to XVII were listed in Table 5. Compounds I to XVII were identified by $H^1$-NMR and FD-MS, and the chemical structure, yield, formula and mass of each of Compounds I to XVII were also listed in Table 5. According to FIGS. 2 to 18 and the results of FD-MS, the chemical structure of Compounds I to XVII were identified as follows.

TABLE 5 reactants and intermediates adopted to prepare Compounds I to XVII and their yields, formulae, and FD-MS data.

| Inter-mediate No. | Reactant No. | Claimed Compound: Chemical Structure of Claimed Compound | Claimed Compound: Yield (%) | Claimed Compound: Formula/ Mass ($M^+$) |
|---|---|---|---|---|
| C1-B | B7 | 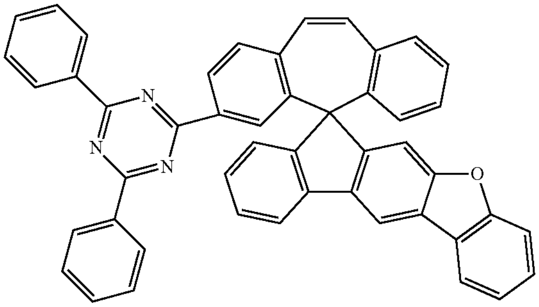 Compound I | 90 | $C_{48}H_{29}N_3O$/ 663.76 |
| C1 | B1 | 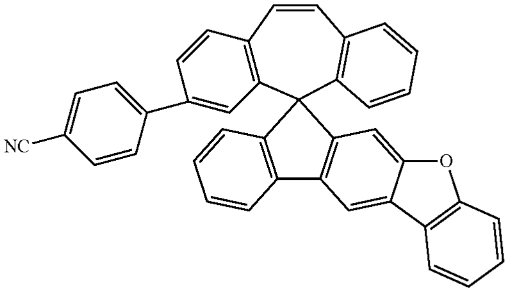 Compound II | 95 | $C_{40}H_{23}NO$/ 553.62 |
| C1 | B8 | 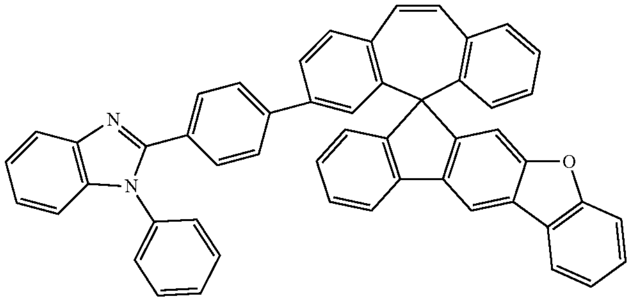 Compound III | 82 | $C_{52}H_{32}N_2O$/ 700.82 |

TABLE 5-continued
| reactants and intermediates adopted to prepare Compounds I to XVII and their yields, formulae, and FD-MS data. | | | | |
|---|---|---|---|---|
| Inter- | | Claimed Compound | | |
| mediate No. | Reactant No. | Chemical Structure of Claimed Compound | Yield (%) | Formula/ Mass ($M^+$) |
| C1-B | B4 | 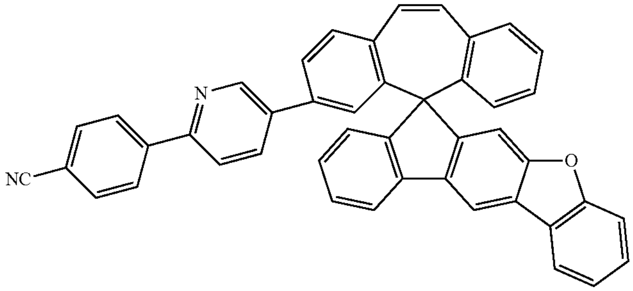 Compound IV | 75 | $C_{45}H_{26}N_2O$/ 610.70 |
| C2-B | B9 | 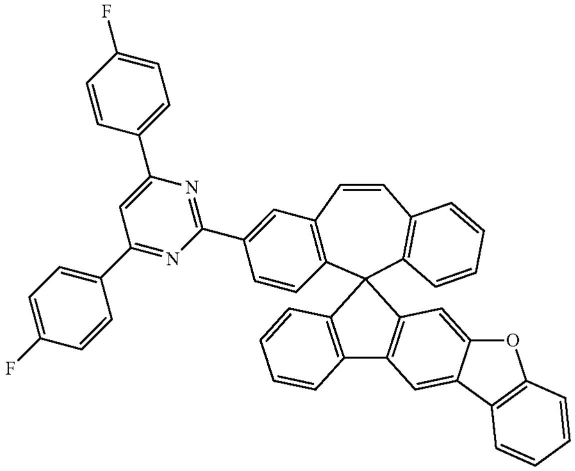 Compound V | 85 | $C_{49}H_{28}F_2N_2O$/ 698.76 |
| C3 | B1 | 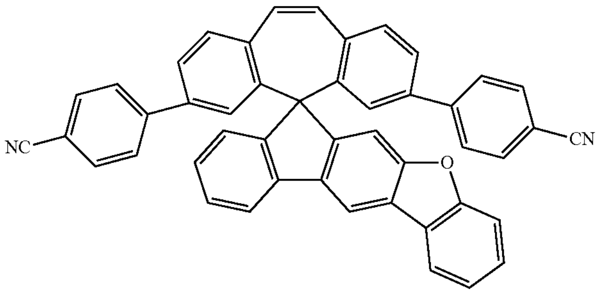 Compound VI | 77 | $C_{47}H_{26}N_2O$/ 634.72 |

TABLE 5-continued
reactants and intermediates adopted to prepare Compounds I to XVII and their yields, formulae, and FD-MS data.
| Inter-mediate No. | Reactant No. | Claimed Compound: Chemical Structure of Claimed Compound | Claimed Compound: Yield (%) | Claimed Compound: Formula/ Mass ($M^+$) |
|---|---|---|---|---|
| C6-B | B7 | 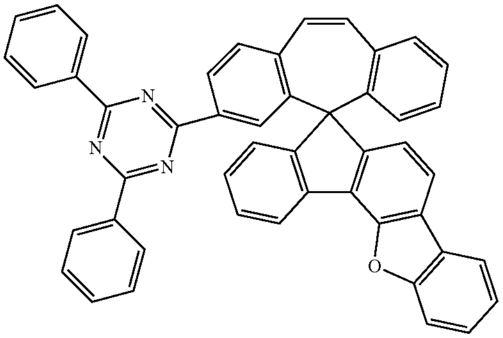 Compound VII | 90 | $C_{48}H_{29}N_3O$/ 663.76 |
| C6 | B1 | 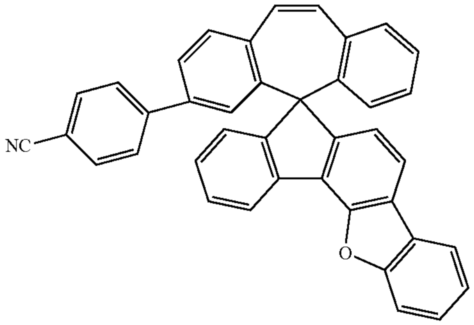 Compound VIII | 70 | $C_{40}H_{23}NO$/ 533.62 |
| C6-B | B10 | 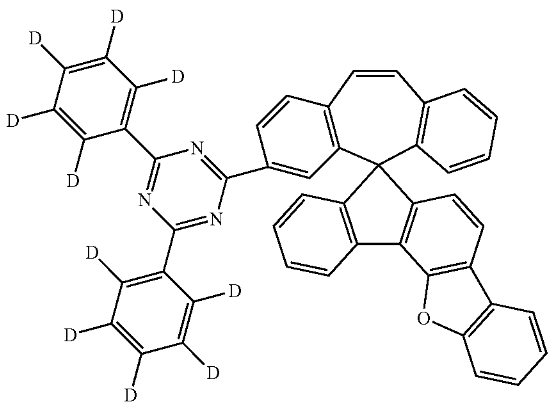 Compound IX | 82 | $C_{48}H_{19}D_{10}N_3O$/ 673.83 |

TABLE 5-continued
reactants and intermediates adopted to prepare Compounds I to XVII and their yields, formulae, and FD-MS data.
| Inter-mediate No. | Reactant No. | Claimed Compound: Chemical Structure of Claimed Compound | Yield (%) | Formula/ Mass ($M^+$) |
|---|---|---|---|---|
| C4-B | B7 | 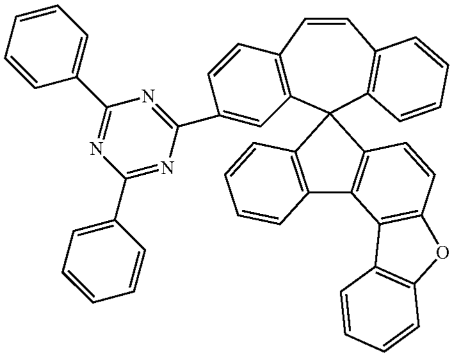 Compound X | 66 | $C_{48}H_{29}N_3O$/ 663.76 |
| C5-B | B7 | 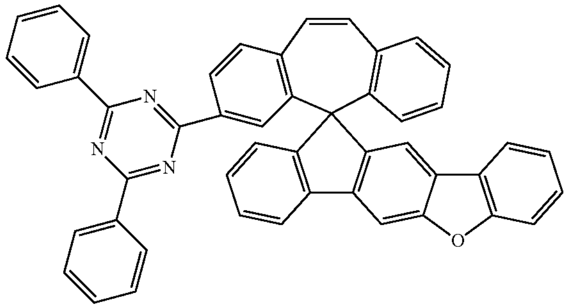 Compound XI | 87 | $C_{48}H_{29}N_3O$/ 663.76 |
| C7 | B3 | 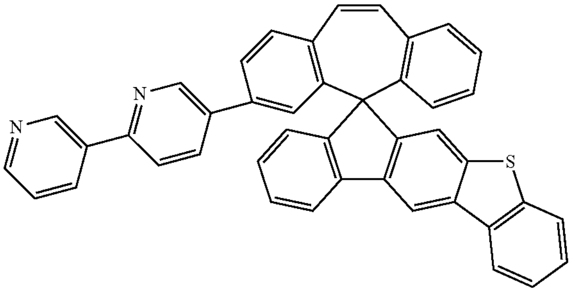 Compound XII | 66 | $C_{43}H_{26}N_2S$/ 602.74 |
| C7-B | B5 | 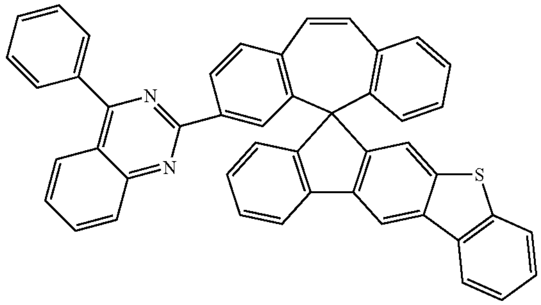 Compound XIII | 90 | $C_{47}H_{28}N_2S$/ 652.80 |

TABLE 5-continued
| reactants and intermediates adopted to prepare Compounds I to XVII and their yields, formulae, and FD-MS data. | | | | |
|---|---|---|---|---|
| Inter- | | Claimed Compound | | |
| mediate No. | Reactant No. | Chemical Structure of Claimed Compound | Yield (%) | Formula/ Mass ($M^+$) |
| C7-B | B6 | 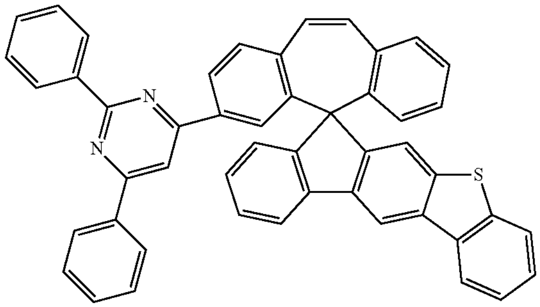 Compound XIV | 82 | $C_{49}H_{30}N_2S$/ 678.84 |
| C8-B | B7 | 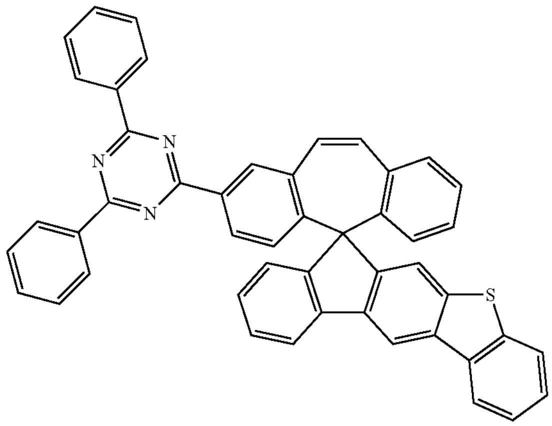 Compound XV | 76 | $C_{48}H_{29}N_3S$/ 679.83 |
| C9-B | B7 | 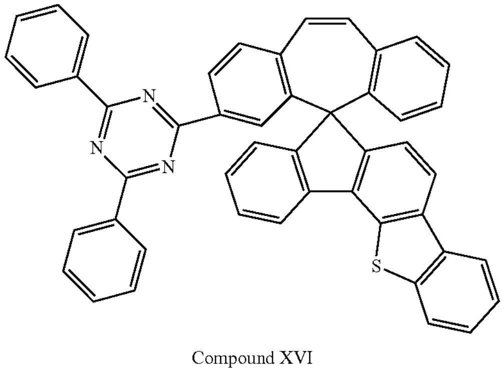 [SMILES: C1=Cc2ccc(-c3nc(-c4ccccc4)nc(-c4ccccc4)n3)cc2C2(c3ccccc31)c1ccccc1-c1c2ccc2c1sc1ccccc12] Compound XVI | 77 | $C_{48}H_{29}N_3S$/ 679.83 |

TABLE 5-continued

| reactants and intermediates adopted to prepare Compounds I to XVII and their yields, formulae, and FD-MS data. | | | | |
|---|---|---|---|---|
| Inter-mediate No. | Reactant No. | Claimed Compound: Chemical Structure of Claimed Compound | Claimed Compound: Yield (%) | Claimed Compound: Formula/ Mass ($M^+$) |
| C9 | B1 | 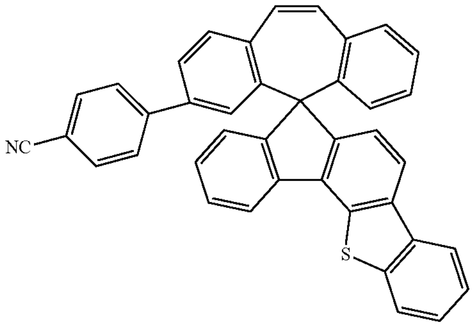 Compound XVII | 78 | $C_{40}H_{23}NS$/ 549.68 |

Modifications of Compounds I to XVII

In addition to the Compounds I to XVII, one person skilled in the art can react any Intermediate C, i.e., the foresaid Intermediate Cn or Cn-B, with any Reactant Bn through a reaction mechanism similar to Scheme I to synthesize other desired claimed novel compounds.

Preparation of OLED Devices

A glass substrate coated with ITO layer (abbreviated as ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 42 and Comparative Examples 1 to 6. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and HIL-2; HI-D was a material for forming HIL-1; HI-2 was a material for forming HIL-1, HIL-2, and HTL-1; HT-1 and HT-2 were respectively materials for forming HTL-1 and HTL-2; novel compounds of the present invention, commercial ETs (BCP and TAZ) were materials for forming ETL; Liq was a material for forming ETD and EIL. RH-1 or RH-2/GH-1 or GH-2/BH was host material for forming REL/GEL/BEL, and RD/GD/BD-1 or BD-2 were dopants for forming REL/GEL/BEL. The main difference of the OLEDs between the Examples and Comparative Examples was that the ETL of OLED in the following comparative examples was made of BCP or TAZ but the ETL of OLED in the following examples was made of the novel compounds of the present invention listed in Table 5. The detailed chemical structures of foresaid commercial materials were listed in Table 6.

TABLE 6
| chemical structures of commercial materials for OLED devices. | | |
|---|---|---|
| HAT | HI-2 | HT-1 |
| 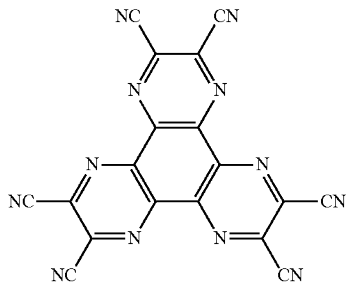 | 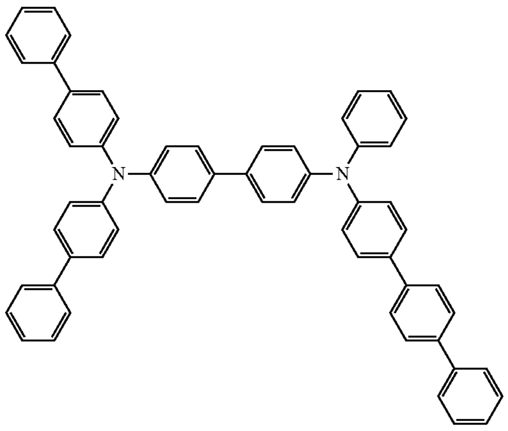 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1] | 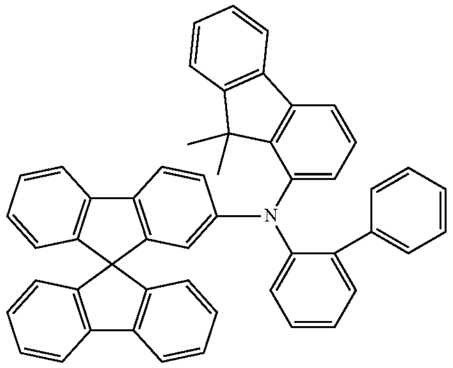 [SMILES: CC1(C)c2ccccc2-c2cccc(N(c3ccc4c(c3)C3(c5ccccc5-c5ccccc53)c3ccccc3-4)c3ccccc3-c3ccccc3)c21] |
| HT-2 | BH | BD-1 |
| 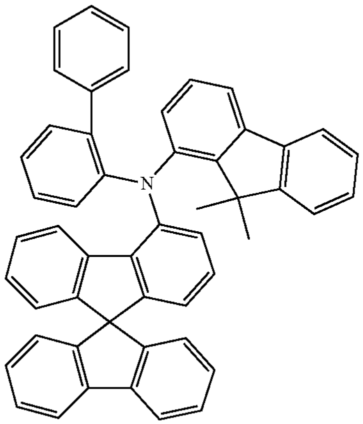 | 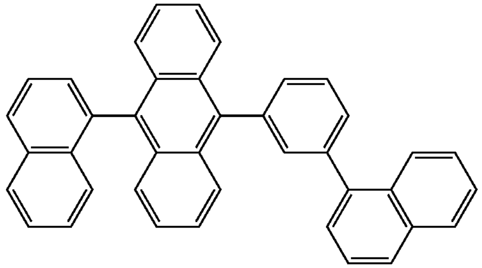 [SMILES: c1cc(-c2cccc3ccccc23)cc(-c2c3ccccc3c(-c3cccc4ccccc34)c3ccccc23)c1] | 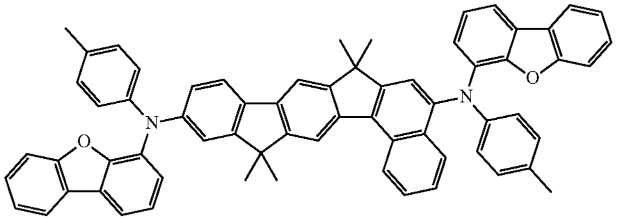 [SMILES: Cc1ccc(N(c2ccc3c(c2)C(C)(C)c2cc4c(cc2-3)C(C)(C)c2cc(N(c3ccc(C)cc3)c3cccc5c3oc3ccccc35)c3ccccc3c2-4)c2cccc3c2oc2ccccc23)cc1] |
| BD-2 | GH-1 | GD |

TABLE 6-continued
| chemical structures of commercial materials for OLED devices. | | |
|---|---|---|
| 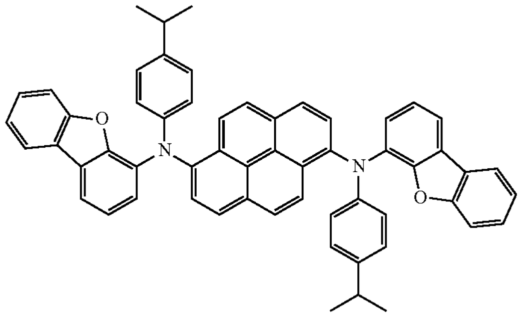 [SMILES: CC(C)c1ccc(N(c2ccc3ccc4c(N(c5ccc(C(C)C)cc5)c5cccc6c5oc5ccccc56)ccc5ccc2c3c54)c2cccc3c2oc2ccccc23)cc1] | 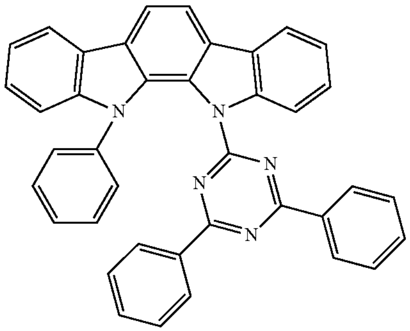 [SMILES: c1ccc(-c2nc(-c3ccccc3)nc(-n3c4ccccc4c4ccc5c6ccccc6n(-c6ccccc6)c5c43)n2)cc1] | 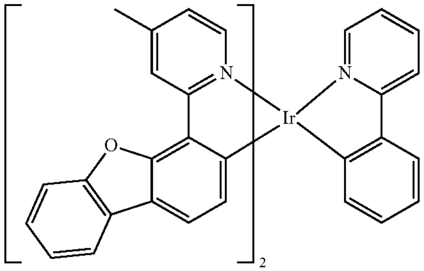 |
| GH-2 | | RH-1 |
| 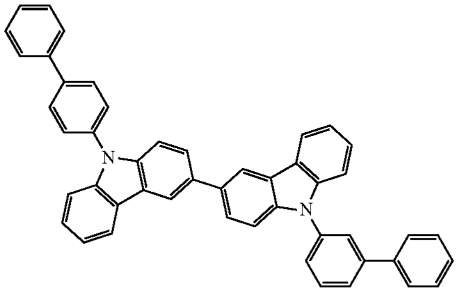 + | 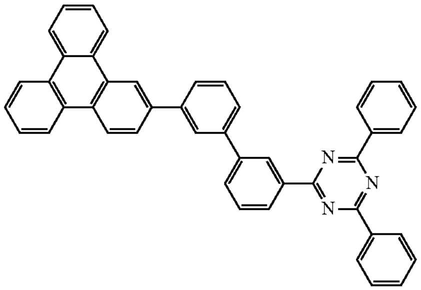 | 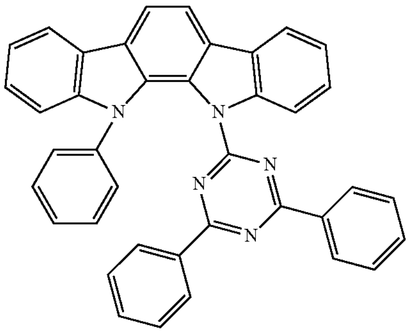 [SMILES: c1ccc(-c2nc(-c3ccccc3)nc(-n3c4ccccc4c4ccc5c6ccccc6n(-c6ccccc6)c5c43)n2)cc1] |
| (1:1) | | |
| RH-2 | RD | Liq |

TABLE 6-continued
| chemical structures of commercial materials for OLED devices. | | |
|---|---|---|
| 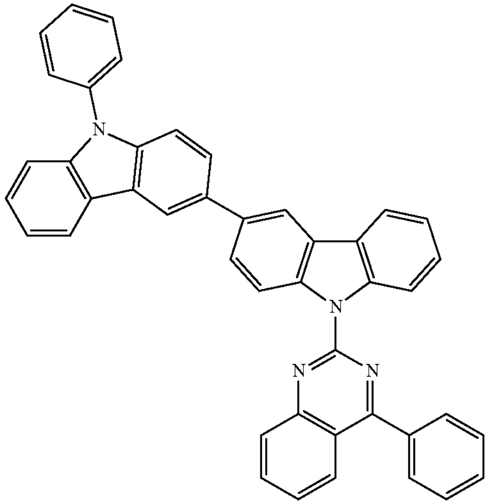 [SMILES: c1ccc(-c2nc(-n3c4ccccc4c4cc(-c5ccc6c(c5)c5ccccc5n6-c5ccccc5)ccc43)nc3ccccc23)cc1] | 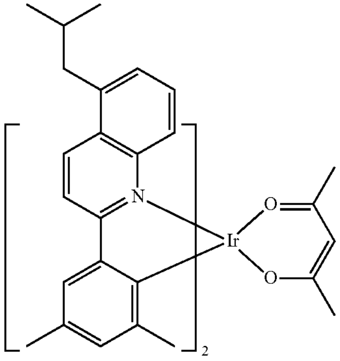 | 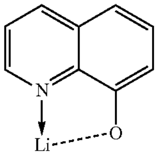 |
| HI-D | BCP (commercial ET) | TAZ (commercial ET) |
| 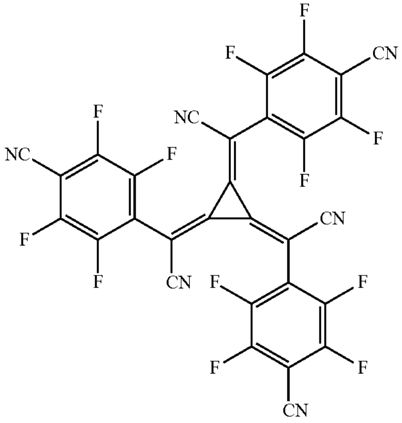 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F] | 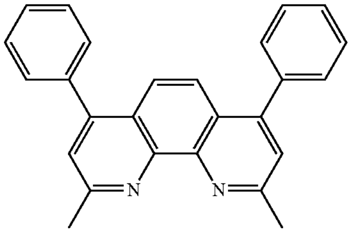 [SMILES: Cc1cc(-c2ccccc2)c2ccc3c(-c4ccccc4)cc(C)nc3c2n1] | 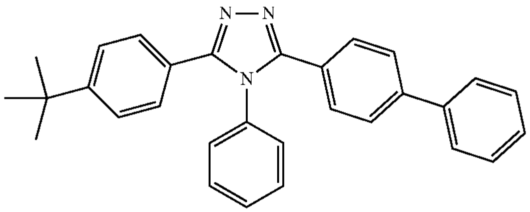 [SMILES: CC(C)(C)c1ccc(-c2nnc(-c3ccc(-c4ccccc4)cc3)n2-c2ccccc2)cc1] |

Preparation of Red OLED Devices

To prepare the red OLED devices, multiple organic layers were respectively deposited on the ITO substrate according to the sequence as listed in Table 7 to prepare a first red OLED device and a second red OLED device. The materials and the thicknesses of the organic layers in the red OLED devices were also listed in Table 7. The difference between the first and the second red OLED devices is the materials of HIL-1, HIL-2, HTL-1, and REL as listed in Table 7.

TABLE 7 coating sequence, materials and thickness of the organic layers in the first and second red OLED devices.

| Coating Sequence | Layer | Material: First red OLED device | Material: Second red OLED device | Thickness |
|---|---|---|---|---|
| 1 | HIL-1 | HAT | HI-2 doped with 3.0 wt % of HI-D | 100 Å |
| 2 | HIL-2 | HI-2 doped with 5.0 wt % of HAT | HI-2 | 2100 Å |
| 3 | HTL-1 | HT-1 | HI-2 | 100 Å |
| 4 | HTL-2 | HT-2 | HT-2 | 100 Å |
| 5 | REL | RH-1 doped with 3.5 wt % of RD | RH-2 doped with 3.5 wt % of RD | 300 Å |
| 6 | ETL | Commercial ET/ novel compounds doped with 35.0 wt % of Liq | Commercial ET/ novel compounds doped with 35.0 wt % of Liq | 350 Å |
| 7 | EIL | Liq | Liq | 15 Å |
| 8 | Cthd | Al | Al | 1500 Å |

Preparation of Green OLED Devices

To prepare the green OLED devices, multiple organic layers were respectively deposited on the ITO substrate according to the sequence as listed in Table 8 to prepare a first green OLED device and a second green OLED device. The materials and the thicknesses of the organic layers in the green OLED devices were also listed in Table 8. The difference between the first and the second green OLED devices is the materials of HIL-1, HIL-2, HTL-1, and GEL as listed in Table 8.

TABLE 8 coating sequence, materials and thickness of the layers in the first and second green OLED devices.

| Coating Sequence | Layer | Material: First green OLED device | Material: Second green OLED device | Thickness |
|---|---|---|---|---|
| 1 | HIL-1 | HAT | HI-2 doped with 3.0 wt % of HI-D | 100 Å |
| 2 | HIL-2 | HI-2 doped with 5.0 wt % of HAT | HI-2 | 1300 Å |
| 3 | HTL-1 | HT-1 | HI-2 | 100 Å |
| 4 | HTL-2 | HT-2 | HT-2 | 100 Å |
| 5 | GEL | GH-1 doped with 10 wt % of GD | GH-2 doped with 10 wt % of GD | 400 Å |
| 6 | ETL | Commercial ET/ novel compounds doped with 35.0 wt % of Liq | Commercial ET/ novel compounds doped with 35.0 wt % of Liq | 350 Å |
| 7 | EIL | Liq | Liq | 15 Å |
| 8 | Cthd | Al | Al | 1500 Å |

Preparation of Blue OLED Devices

To prepare the blue OLED devices, multiple organic layers were respectively deposited on the ITO substrate according to the sequence as listed in Table 9 to prepare a first blue OLED device and a second blue OLED device. The materials and the thicknesses of the organic layers in the blue OLED devices were also listed in Table 9. For the blue OLEDs, the dopant could be BD-1 or BD-2 as listed in Table 9. The difference between the first and the second blue OLED devices is the materials of HIL-1, HIL-2, HTL-1, and BEL as listed in Table 9.

TABLE 9 coating sequence, materials and thickness of the layers in the first and second blue OLED devices.

| Coating Sequence | Layer | Material: First blue OLED device | Material: Second blue OLED device | Thickness |
|---|---|---|---|---|
| 1 | HIL-1 | HAT | HI-2 doped with 3.0 wt % of HI-D | 100 Å |
| 2 | HIL-2 | HI-2 doped with 5.0 wt % of HAT | HI-2 | 750 Å |
| 3 | HTL-1 | HT-1 | HI-2 | 100 Å |
| 4 | HTL-2 | HT-2 | HT-2 | 100 Å |
| 5 | BEL | BH doped with 3.5 wt % of BD1 | BH doped with 3.5 wt % of BD2 | 300 Å |
| 6 | ETL | Commercial ET/ novel compounds doped with 35.0 wt % of Liq | Commercial ET/ novel compounds doped with 35.0 wt % of Liq | 350 Å |
| 7 | EIL | Liq | Liq | 15 Å |
| 8 | Cthd | Al | Al | 1500 Å |

Performance of OLED Devices

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 10. For the blue and red OLED devices, the data were collected at 1000 nits. For the green OLED devices, the data were collected at 3000 nits.

The materials of ETL, color and data of CIE, driving voltage, and current efficiency of Examples 1 to 42 and Comparative Example 1 to 4 were listed in Table 10. As listed in Table 10, the first blue OLED devices were named as B1, and the second blue OLED devices were named as B2. Similarly, the first and second red OLED devices and the first and second green OLED devices were respectively named as R1, R2, G1, and G2.

TABLE 10 materials of ETL, colors, CIEs, voltages, and current efficiencies of OLED devices of Examples 1 to 42 and Comparative Example 1 to 6.

| Example No. | Material of ETL | OLED device No. | CIE(x, y) | Voltage (V) | Current Efficiency (cd/A) |
|---|---|---|---|---|---|
| E1 | Compound II | B1 | (0.137, 0.197) | 3.83 | 10.5 |
| E2 | Compound VI | B1 | (0.135, 0.18) | 4.55 | 9.2 |
| E3 | Compound VIII | B1 | (0.136, 0.176) | 3.97 | 9.66 |
| E4 | Compound I | B2 | (0.129, 0.157) | 4.7 | 7.81 |
| E5 | Compound III | B2 | (0.129, 0.157) | 5.16 | 7.45 |
| E6 | Compound IV | B2 | (0.130, 0.152) | 4.31 | 8.31 |
| E7 | Compound VII | B2 | (0.130, 0.150) | 4.44 | 7.73 |
| E8 | Compound IX | B2 | (0.129, 0.17) | 4.62 | 8.3 |
| E9 | Compound X | B2 | (0.129, 0.161) | 4.43 | 8.08 |
| E10 | Compound XI | B2 | (0.130, 0.153) | 4.49 | 7.94 |
| E11 | Compound XII | B2 | (0.130, 0.163) | 4.44 | 8.99 |

TABLE 10-continued materials of ETL, colors, CIEs, voltages, and current efficiencies of OLED devices of Examples 1 to 42 and Comparative Example 1 to 6.

| Example No. | Material of ETL | OLED device No. | CIE(x, y) | Voltage (V) | Current Efficiency (cd/A) |
|---|---|---|---|---|---|
| E12 | Compound XIII | B2 | (0.129, 0.161) | 4.86 | 7.45 |
| E13 | Compound XIV | B2 | (0.130, 0.164) | 4.1 | 10.4 |
| E14 | Compound XV | B2 | (0.129, 0.158) | 4.45 | 10 |
| E15 | Compound XVI | B2 | (0.129, 0.156) | 4.79 | 7.86 |
| E16 | Compound XVII | B2 | (0.138, 0.181) | 3.88 | 12.2 |
| C1 | BCP | B1 | (0.130, 0.170) | 6.35 | 7.05 |
| C2 | TAZ | B2 | (0.131, 0.174) | 7.84 | 6.55 |
| E17 | Compound II | G1 | (0.309, 0.641) | 3.06 | 66.0 |
| E18 | Compound VI | G1 | (0.307, 0.642) | 3.24 | 70.3 |
| E19 | Compound VIII | G1 | (0.322, 0.635) | 3.33 | 77.6 |
| E20 | Compound I | G2 | (0.313, 0.639) | 4.21 | 71.4 |
| E21 | Compound III | G2 | (0.312, 0.639) | 5.05 | 57.5 |
| E22 | Compound IV | G2 | (0.322, 0.634) | 4.4 | 75.9 |
| E23 | Compound V | G2 | (0.321, 0.634) | 6.17 | 74.1 |
| E24 | Compound VII | G2 | (0.319, 0.636) | 4.3 | 78.3 |
| E25 | Compound IX | G2 | (0.328, 0.63) | 4.25 | 77.4 |
| E26 | Compound X | G2 | (0.323, 0.633) | 4.16 | 75.8 |
| E27 | Compound XI | G2 | (0.317, 0.637) | 3.96 | 72.2 |
| E28 | Compound XII | G2 | (0.322, 0.635) | 4.25 | 72 |
| E29 | Compound XIII | G2 | (0.324, 0.633) | 4.93 | 58.9 |
| E30 | Compound XIV | G2 | (0.321, 0.634) | 3.99 | 80.2 |
| E31 | Compound XV | G2 | (0.322, 0.634) | 4.75 | 79.9 |
| E32 | Compound XVI | G2 | (0.323, 0.634) | 4.24 | 76.2 |
| E33 | Compound XVII | G2 | (0.317, 0.638) | 3.51 | 77.2 |
| C3 | BCP | G1 | (0.313, 0.638) | 5.27 | 65.3 |
| C4 | TAZ | G2 | (0.325, 0.628) | 8.36 | 48.4 |
| E34 | Compound II | R1 | (0.606, 0.339) | 3.18 | 22.5 |
| E35 | Compound VI | R1 | (0.659, 0.339) | 3.23 | 20.8 |
| E36 | Compound VIII | R1 | (0.662, 0.337) | 3.43 | 24.9 |
| E37 | Compound IV | R2 | (0.659, 0.339) | 4.09 | 28 |
| E38 | Compound IX | R2 | (0.658, 0.34) | 3.9 | 29.7 |
| E39 | Compound XII | R2 | (0.658, 0.34) | 4.55 | 26.8 |
| E40 | Compound XIV | R2 | (0.656, 0.341) | 4.13 | 29.9 |
| E41 | Compound XV | R2 | (0.657, 0.341) | 4.31 | 30.6 |
| E42 | Compound XVII | R2 | (0.663, 0.336) | 3.91 | 23.3 |
| C5 | BCP | R1 | (0.659, 0.340) | 4.16 | 20.10 |
| C6 | TAZ | R2 | (0.648, 0.342) | 11.38 | 21.04 |

Based on the results, in comparison with the commercial electron transport material, adopting Compounds I to XVII as the electron transport material can reduce the driving voltage and improve the current efficiency of the red, green, or blue OLEDs. It demonstrated that the novel compound of the present invention is suitable as an electron transport material for any color OLEDs, and allows the OLEDs using the same to have low driving voltage and improved current efficiency.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound represented by the following Formula (I):

Formula (I)

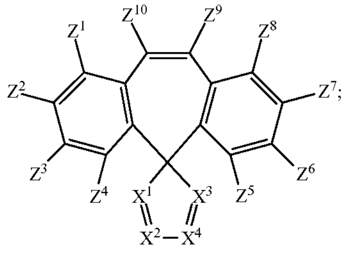

wherein $X^1$ and $X^2$ are each independently $C(R^a)$, the two $(R^a)$s are the same or different, and the two $(R^a)$s are joined together to form an aryl ring;

wherein $X^3$ and $X^4$ are each independently $C(R^b)$, the two $(R^b)$s are the same or different, and the two $(R^b)$s are joined together to form a heteroaryl ring containing at least one furan group, or at least one thiophene group;

wherein at least one of $Z^1$ to $Z^8$ in Formula (I) is selected from the group consisting of:

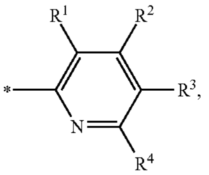

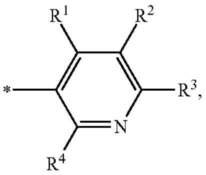

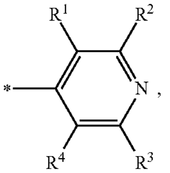

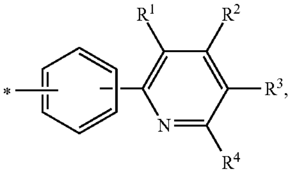

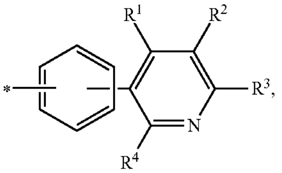

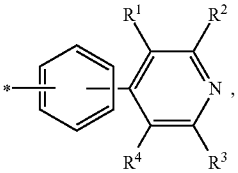

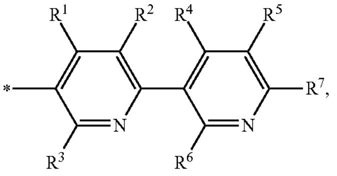

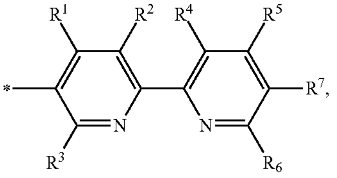

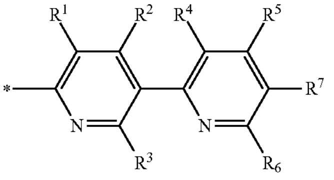

-continued
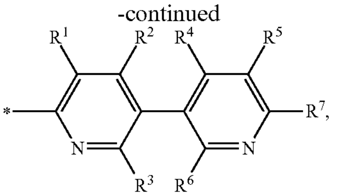
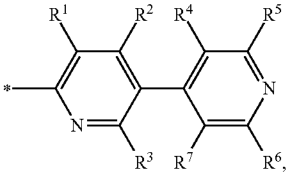
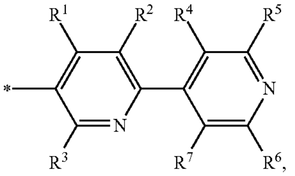
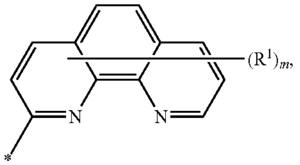
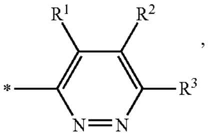
,
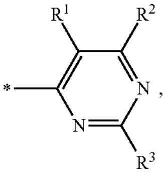
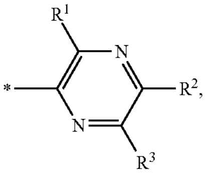
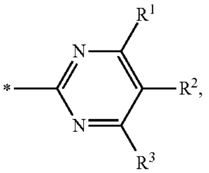
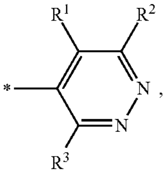
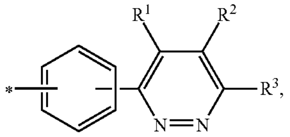
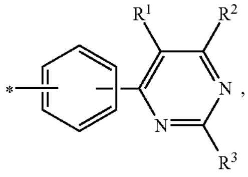
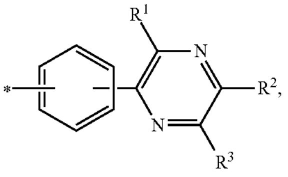
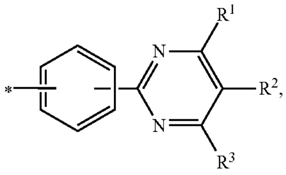
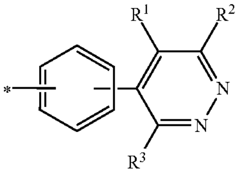
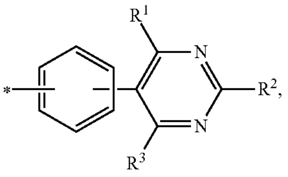
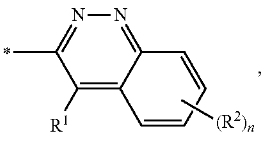
,
-continued
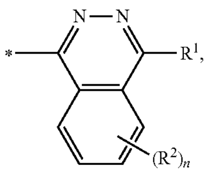
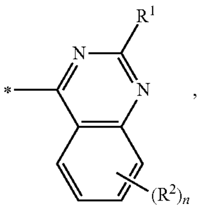
,
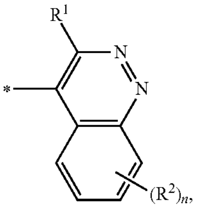
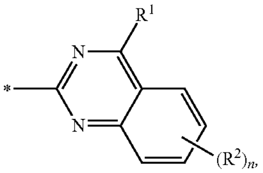
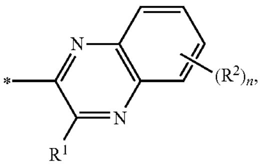
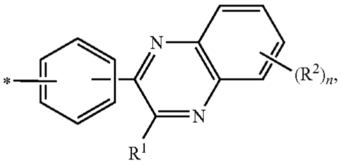
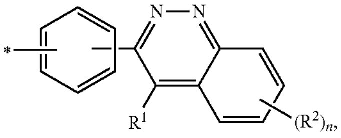
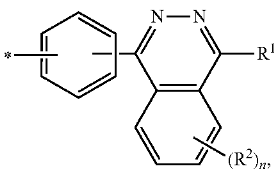
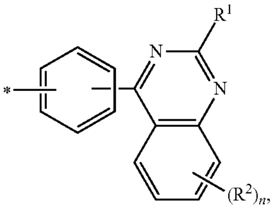
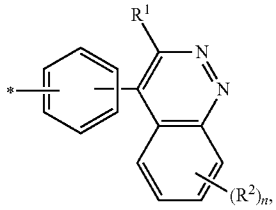
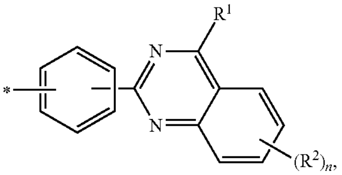
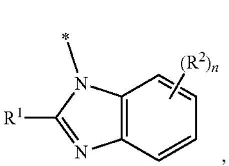
,
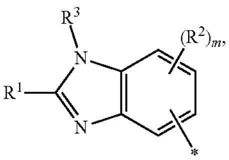
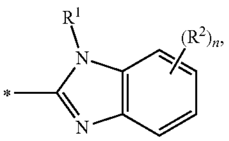

-continued

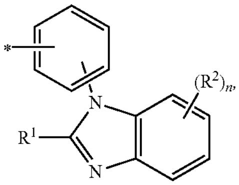

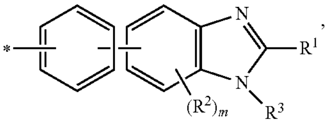

,

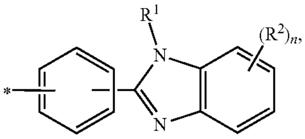

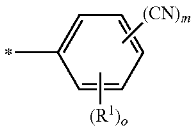

,

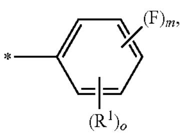

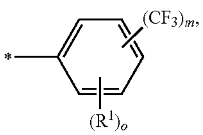

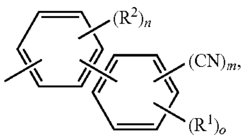

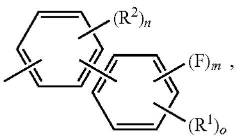

,

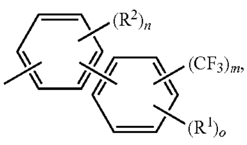

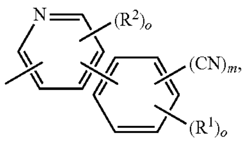

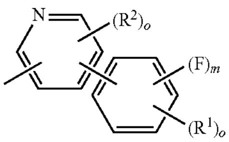

,

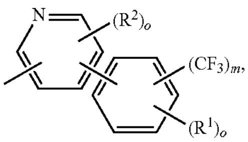

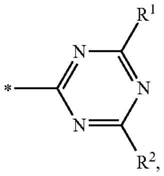

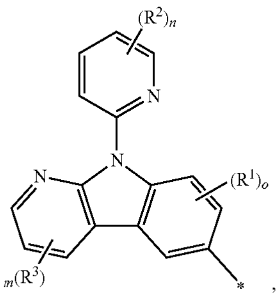

,

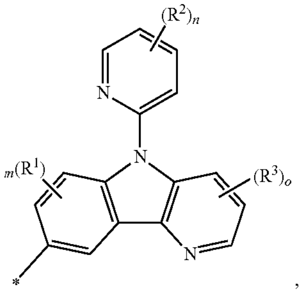

,

-continued

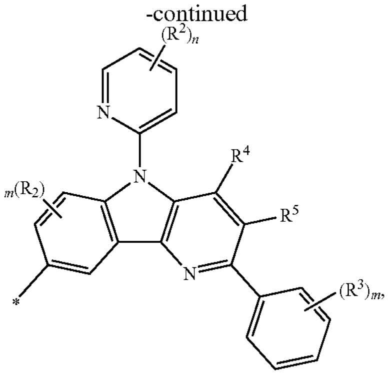

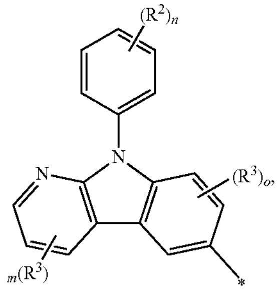

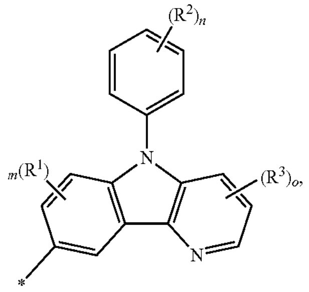

and

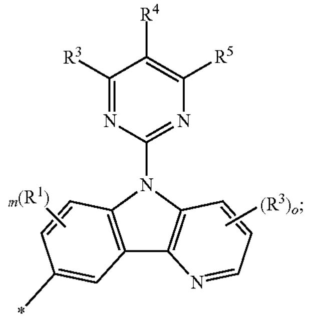

wherein $R^1$ to $R^7$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is a positive integer from 0 to 4, m is a positive integer from 0 to 3, o is a positive integer from 0 to 3, and the total of m and o is not more than 5;

the other(s) of $Z^1$ to $Z^8$, $Z^9$ and $Z^{10}$ are each independently selected from the group consisting of: a hydrogen atom, a deuterium atom, a trifluoromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

2. The compound as claimed in claim 1, wherein the compound is represented by Formula (I-I)

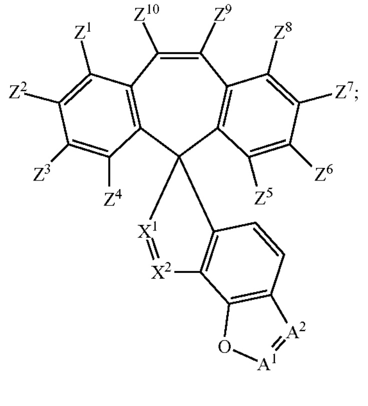

Formula (I-II)

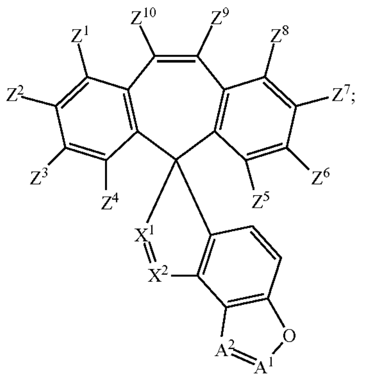

-continued

Formula (I-III)

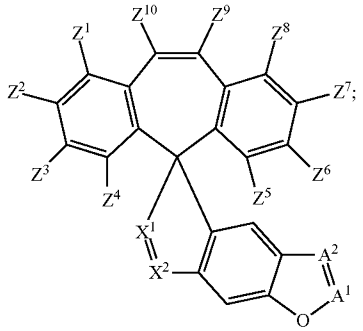

Formula (I-IV)

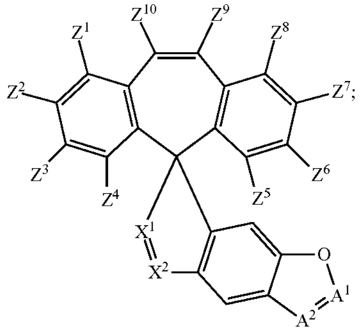

Formula (I-V)

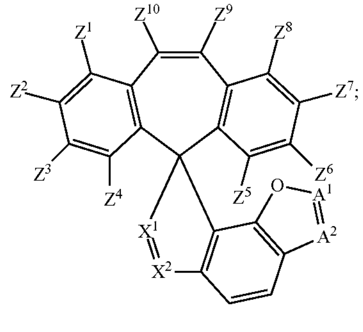

Formula (I-VI)

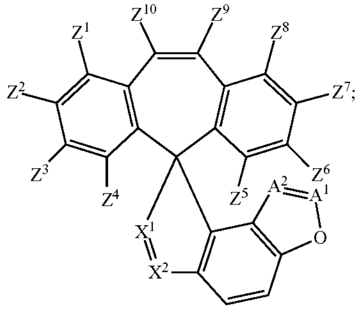

-continued

Formula (I-VII)

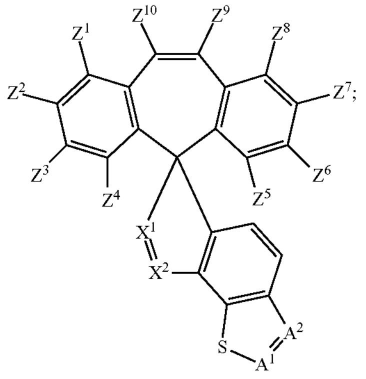

Formula (I-VIII)

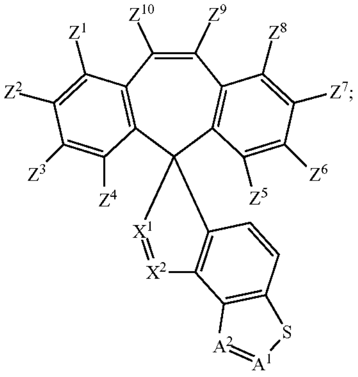

Formula (I-IX)

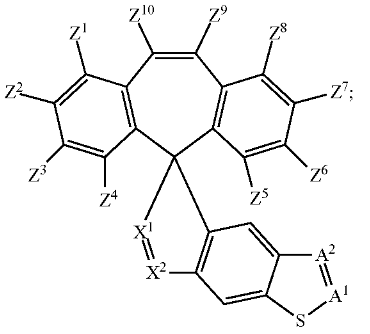

Formula (I-X)

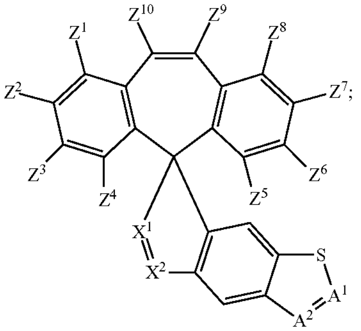

-continued

Formula (I-XI)

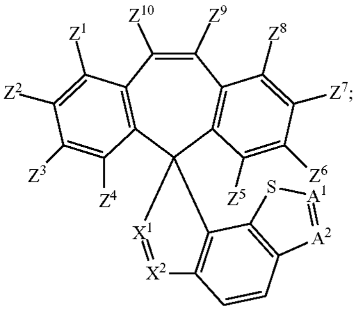

or

Formula (I-XII)

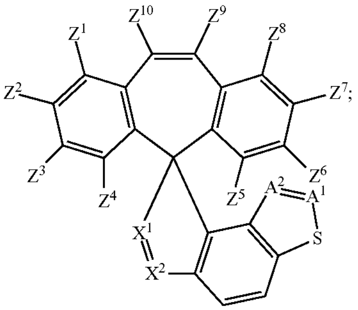

wherein $A^1$ and $A^2$ are each independently $C(R^c)$, the two $(R^c)$s are the same or different, and the two $(R^c)$s are joined together to form an aromatic structure contained in the heteroaryl ring.

3. The compound as claimed in claim 2, wherein the aromatic structure contained in the heteroaryl ring is a substituted or unsubstituted 6 to 20-membered carbon aromatic cyclic structure.

4. The compound as claimed in claim 3, wherein the substituted or unsubstituted 6 to 20-membered carbon aromatic cyclic structure is selected from the group consisting of: a substituted or unsubstituted benzene structure, a substituted or unsubstituted naphthalene structure, a substituted or unsubstituted anthracene structure, a substituted or unsubstituted phenanthrene structure, a substituted or unsubstituted fluorene structure, a substituted or unsubstituted pyrene structure, a substituted or unsubstituted benzophenanthrene structure, a substituted or unsubstituted benzopyrene structure, a substituted or unsubstituted fluoranthene structure, and a substituted or unsubstituted benzofluoranthene structure.

5. The compound as claimed in claim 1, wherein the aryl ring is a substituted or unsubstituted 6 to 60-membered carbon ring.

6. The compound as claimed in claim 5, wherein the substituted or unsubstituted 6 to 60-membered carbon ring is selected from the group consisting of: a substituted or unsubstituted benzene ring, a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, and a substituted or unsubstituted benzofluoranthene ring.

7. The compound as claimed in claim 6, wherein the substituted or unsubstituted 6 to 60-membered carbon ring is a substituted or unsubstituted benzene structure.

8. The compound as claimed in claim 1, wherein at least one of $Z^2$, $Z^3$, $Z^6$, and $Z^7$ in Formula (I) is selected from the group consisting of:
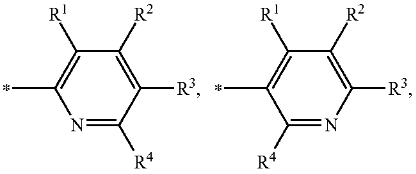
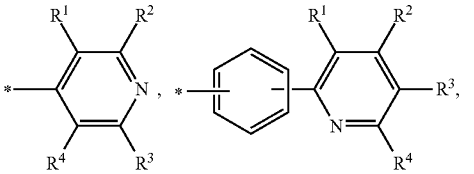
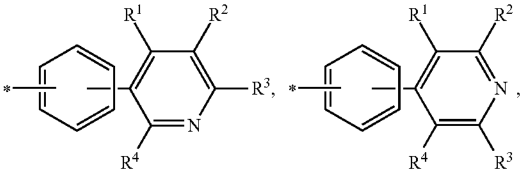
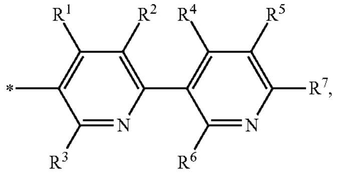
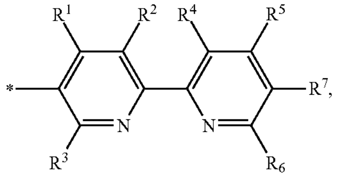
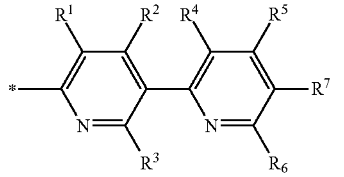
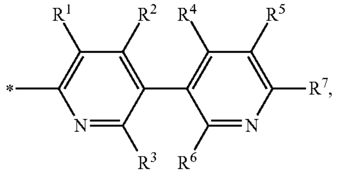
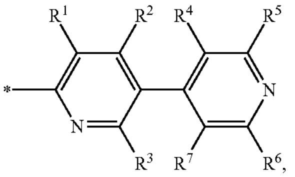
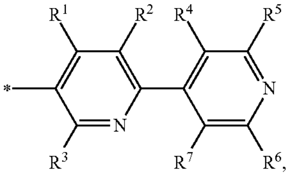
-continued
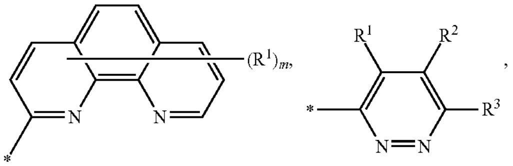
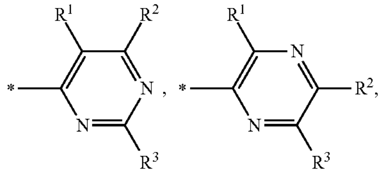
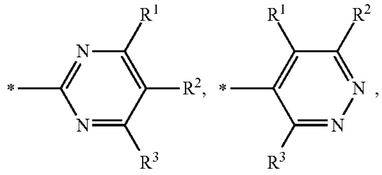
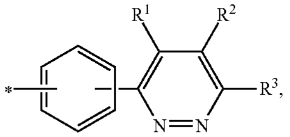
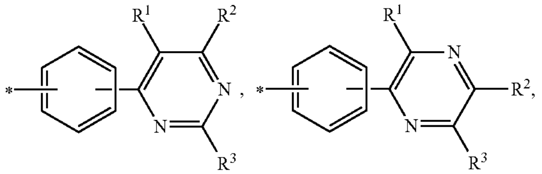
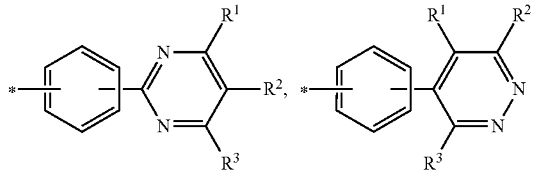
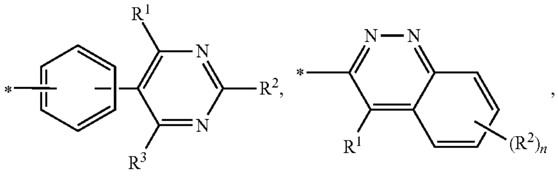
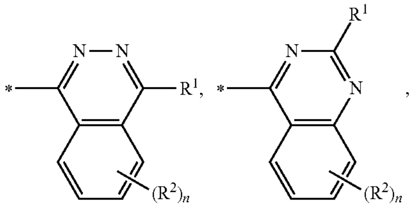
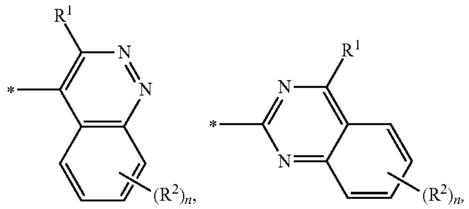

-continued
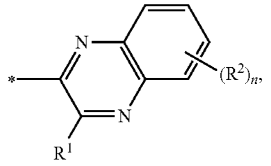
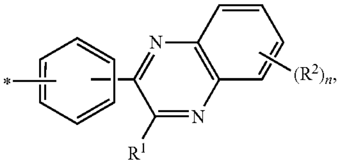
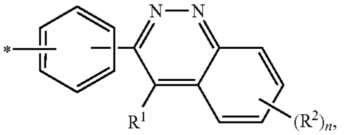
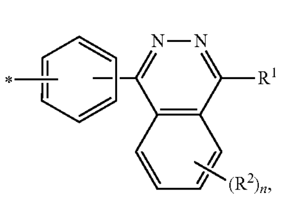 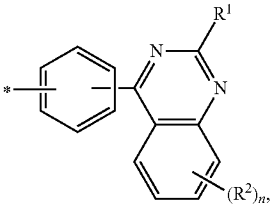
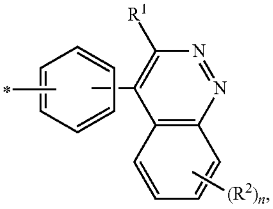
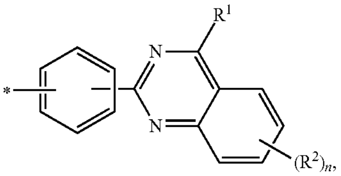 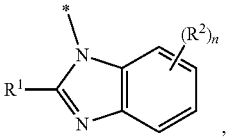,
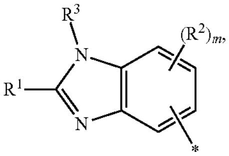 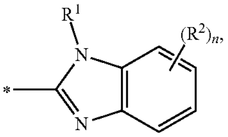
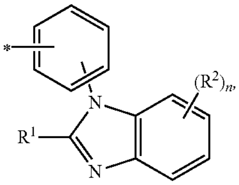 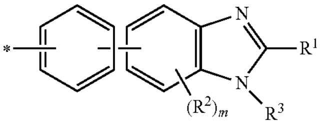,
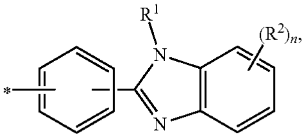 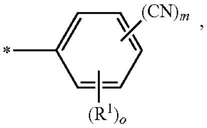
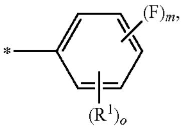 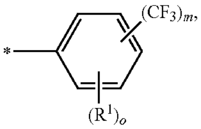
-continued
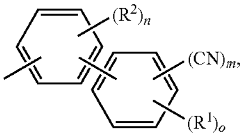 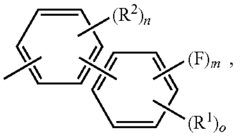
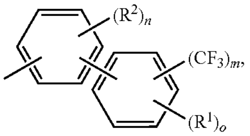 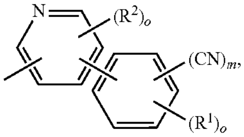
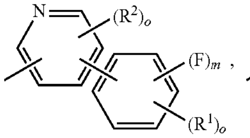 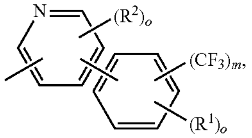
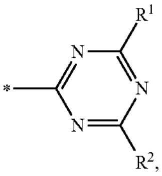 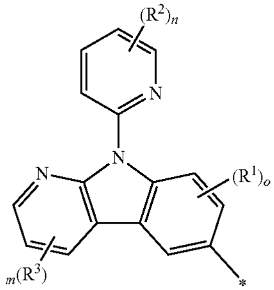,
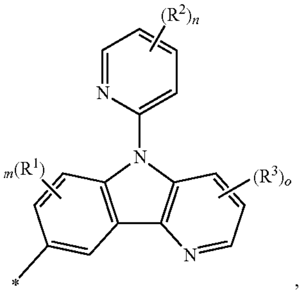,
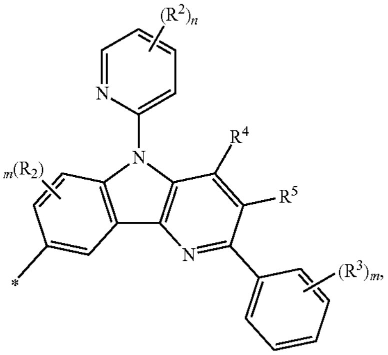
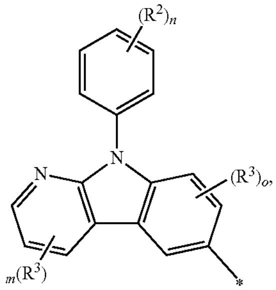

-continued

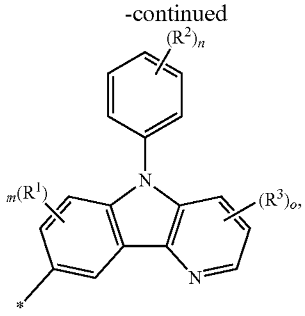

, and

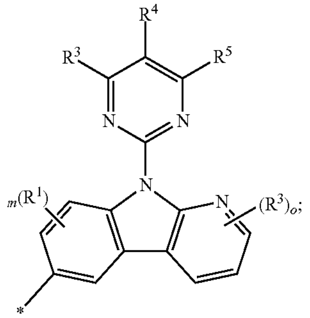

;

wherein $R^1$ to $R^7$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is a positive integer from 0 to 4, m is a positive integer from 0 to 3, o is a positive integer from 0 to 3, and the total of m and o is not more than 5;

wherein $Z^1$, $Z^4$, $Z^5$, $Z^8$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

9. The compound as claimed in claim 8, wherein at least one of $Z^2$, $Z^3$, $Z^6$, and $Z^7$ in Formula (I) is selected from the group consisting of:

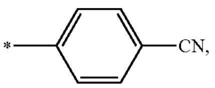

,

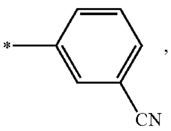

,

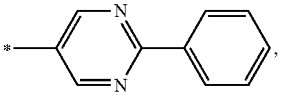

,

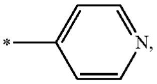

,

-continued

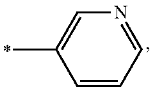

,

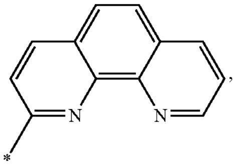

,

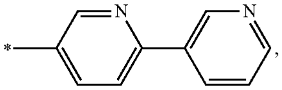

,

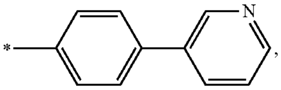

,

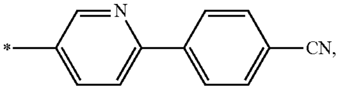

,

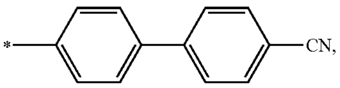

,

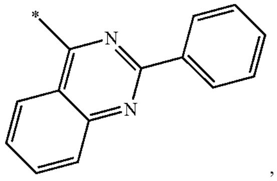

,

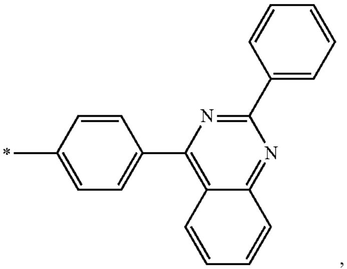

,

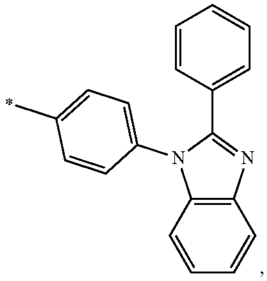

,

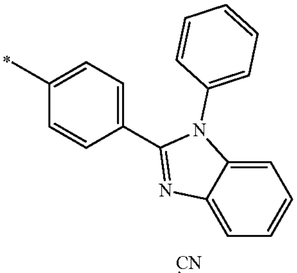

,

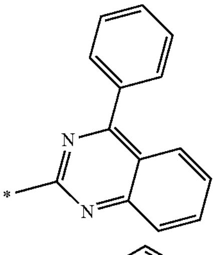

,

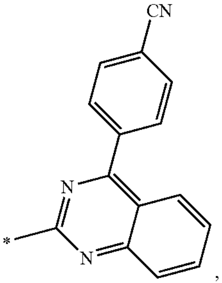

,

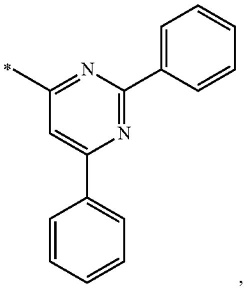

,

-continued
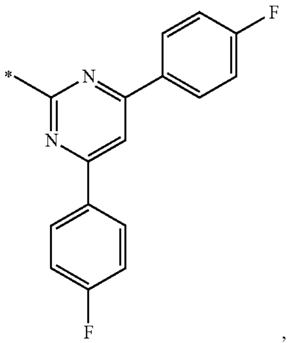
,
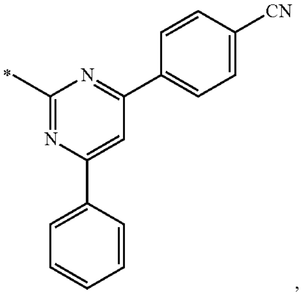
,
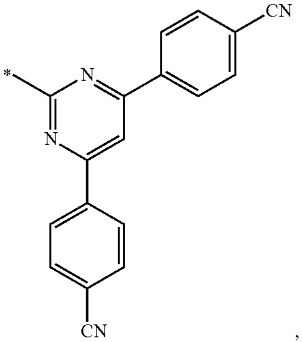
,
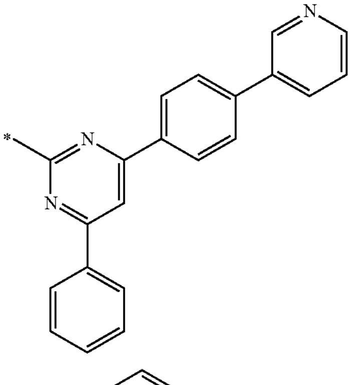
,
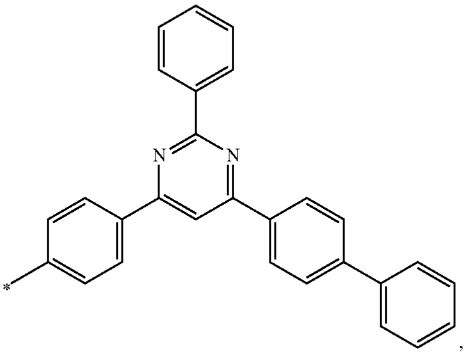
,
-continued
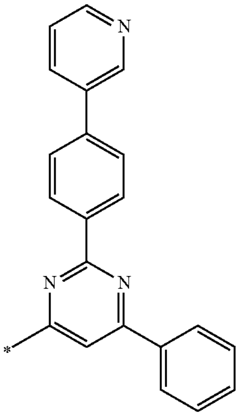
,
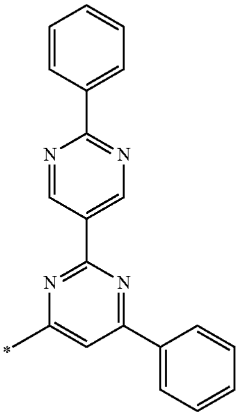
,
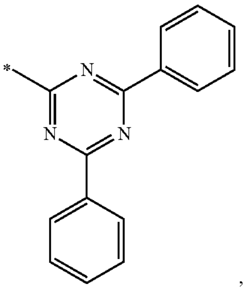
,
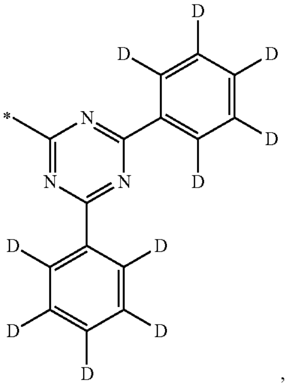
,
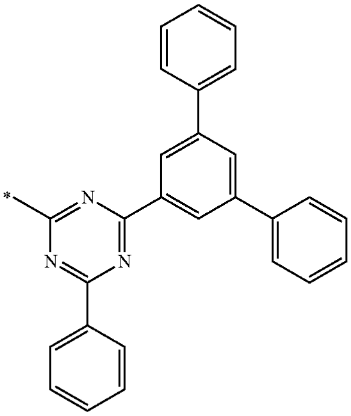
,
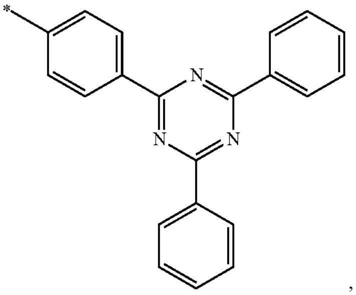
, -continued

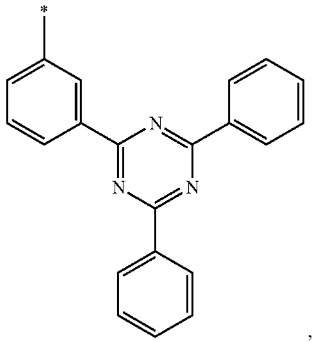

,

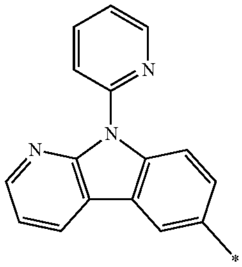

,

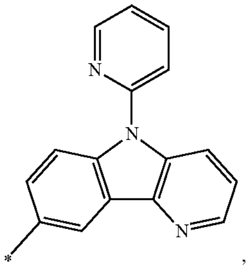

,

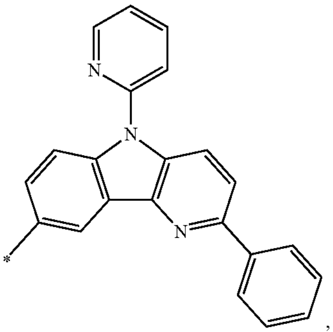

,

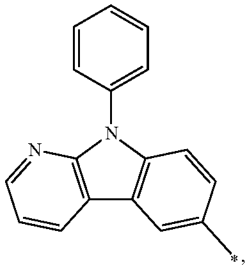

, and

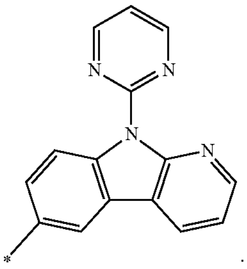

.

10. The compound as claimed in claim 1, wherein $Z^9$ and $Z^{10}$ in Formula (I) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

11. The compound as claimed in claim 1, wherein the compound is selected from the group consisting of:

Compound I

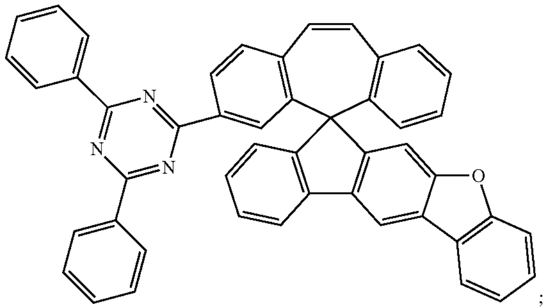

;

Compound II

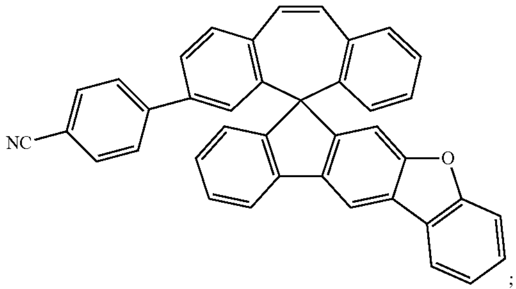

;

Compound III

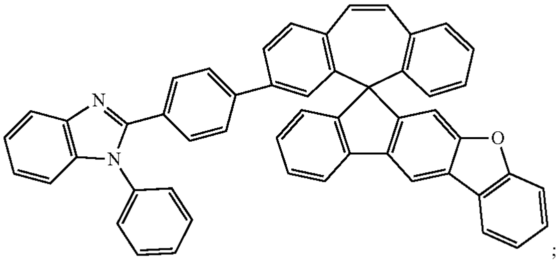

;

Compound IV

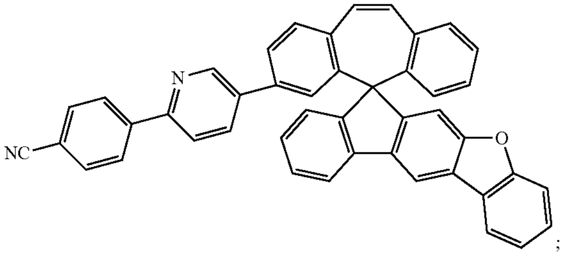

;

-continued
Compound V
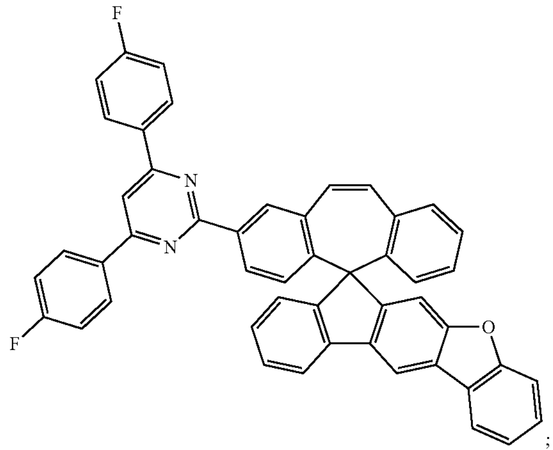
;
Compound VI
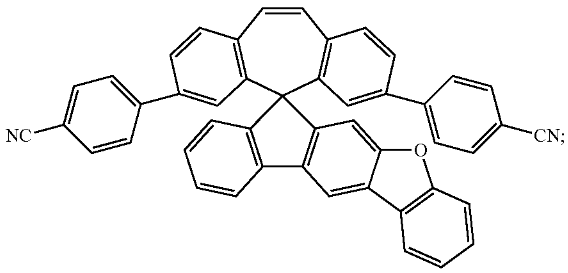
CN;
Compound VII
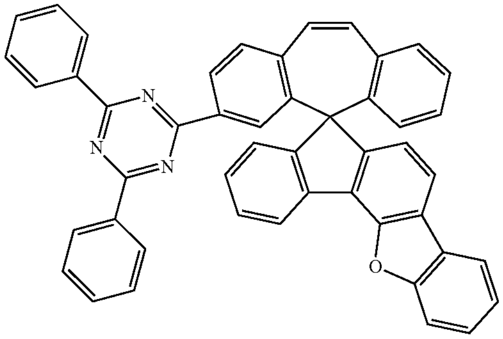
;
Compound VIII
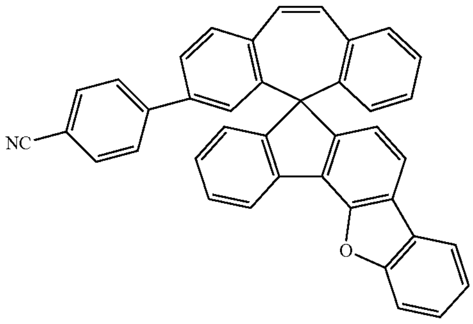
;
-continued
Compound IX
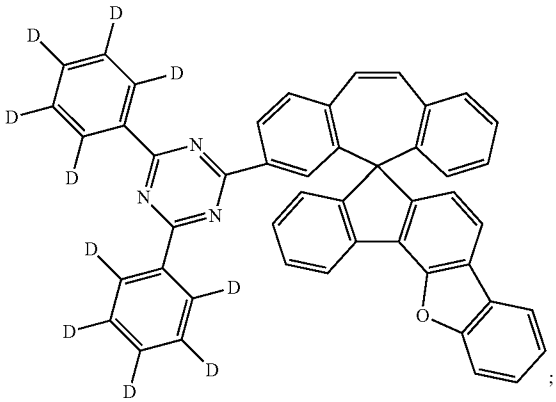
;
Compound X
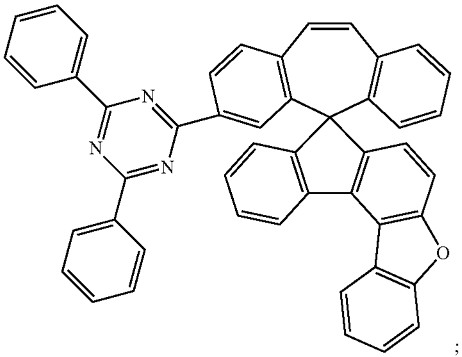
;
Compound XI
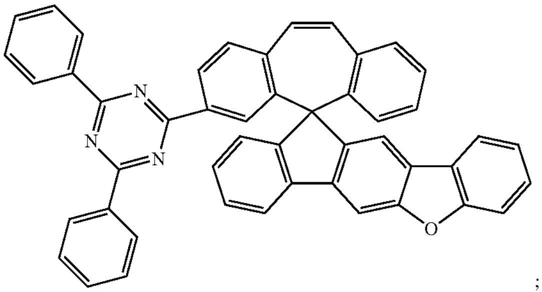
;
Compound XII
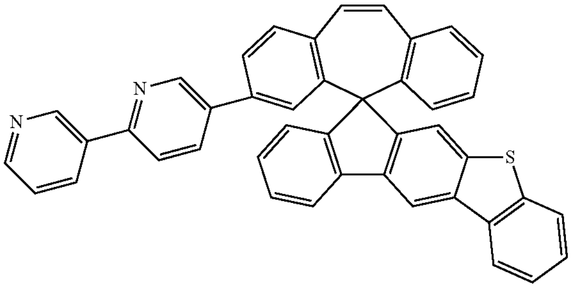
;

-continued

Compound XIII

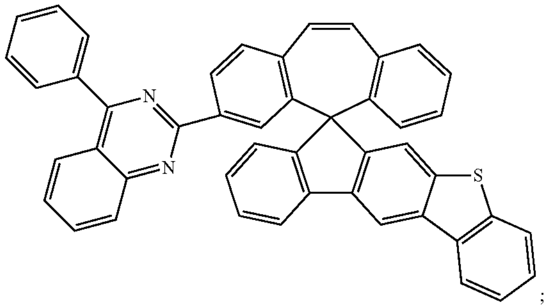

;

Compound XIV

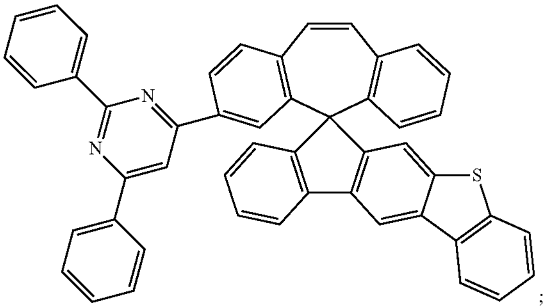

;

Compound XV

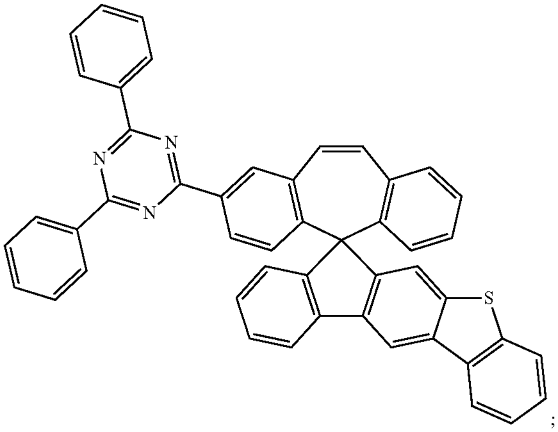

;

Compound XVI

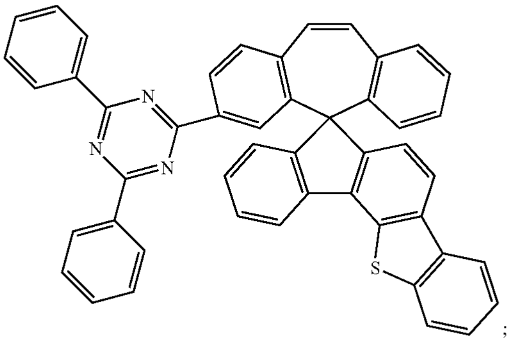

; and

-continued

Compound XVII

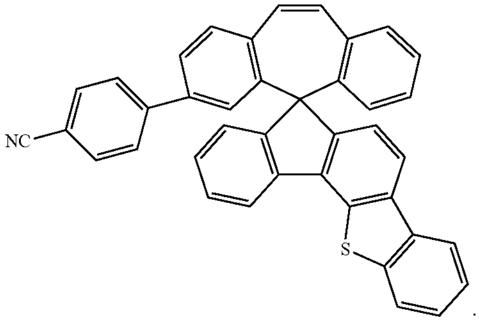

.

12. An organic electronic device, comprising a first electrode, a second electrode, and an organic layer disposed between the first electrode and the second electrode, wherein the organic layer comprises the compound as claimed in claim 1.

13. The organic electronic device as claimed in claim 12, wherein the organic electronic device is an organic light emitting device.

14. The organic electronic device as claimed in claim 13, wherein the organic light emitting device comprises:

a hole injection layer formed on the first electrode;

a hole transport layer formed on the hole injection layer;

an emission layer formed on the hole transport layer;

an electron transport layer formed on the emission layer, wherein the organic layer is the electron transport layer; and an electron injection layer formed between the electron transport layer and the second electrode.

15. The organic electronic device as claimed in claim 13, wherein the organic light emitting device comprises:

a hole injection layer formed on the first electrode;

a hole transport layer formed on the hole injection layer;

an emission layer formed on the hole transport layer;

a hole blocking layer formed on the emission layer, wherein the organic layer is the hole blocking layer;

an electron transport layer formed on the hole blocking layer; and an electron injection layer formed between the electron transport layer and the second electrode.

16. The organic electronic device as claimed in claim 12, wherein the compound is selected from the group consisting of:

Compound I

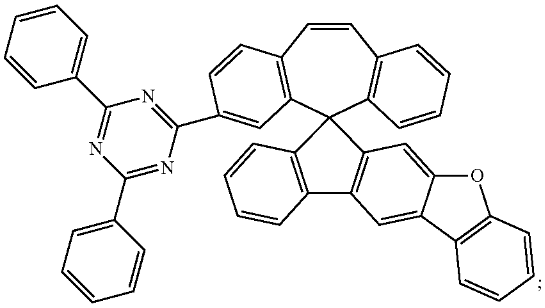

;

-continued
Compound II
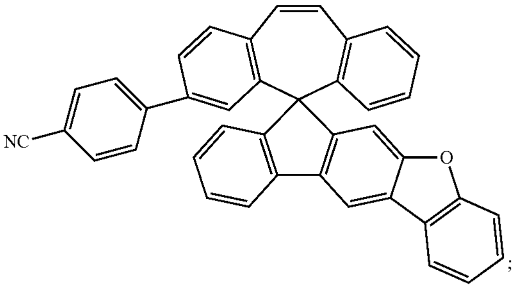
;
Compound III
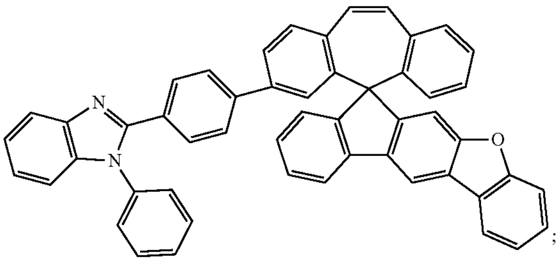
;
Compound IV
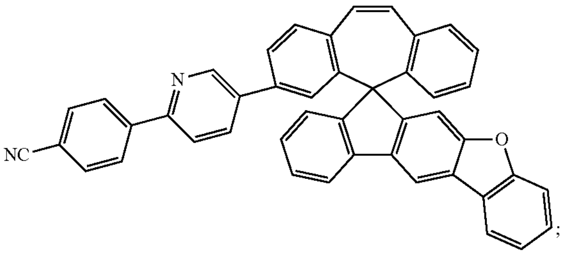
;
Compound V
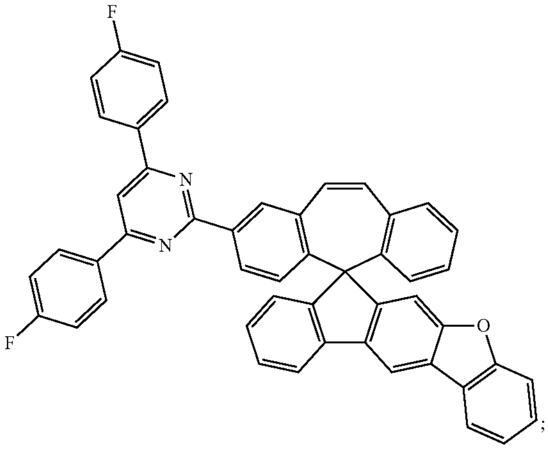
;
Compound VI
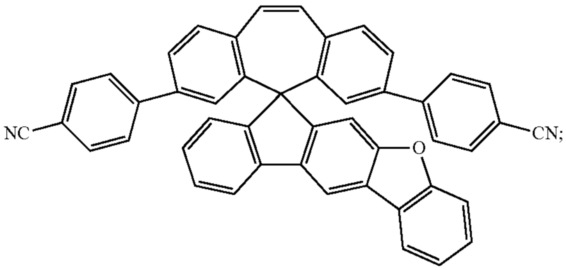
;
-continued
Compound VII
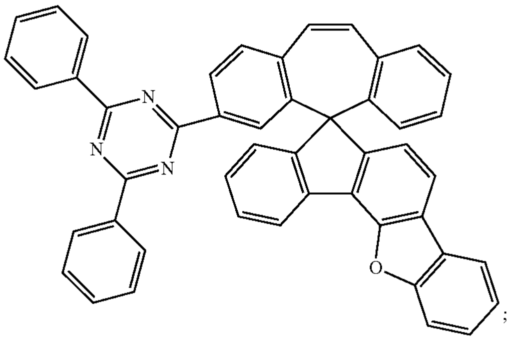
;
Compound VIII
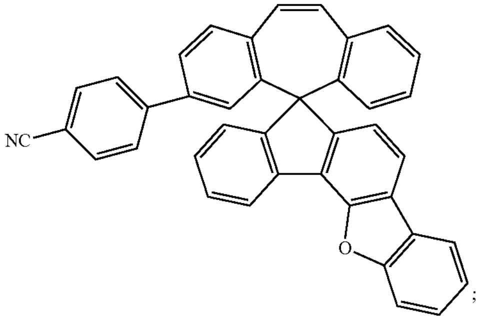
;
Compound IX
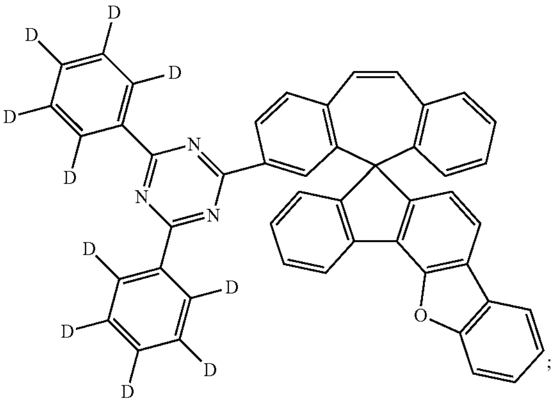
;
Compound X
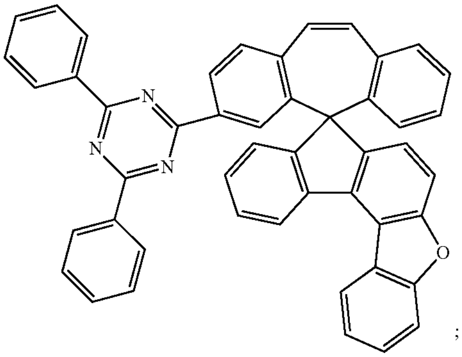
;

-continued
Compound XI
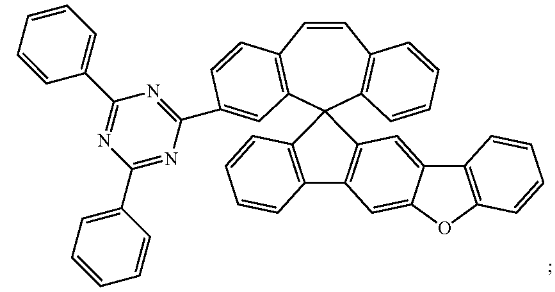
;
Compound XII
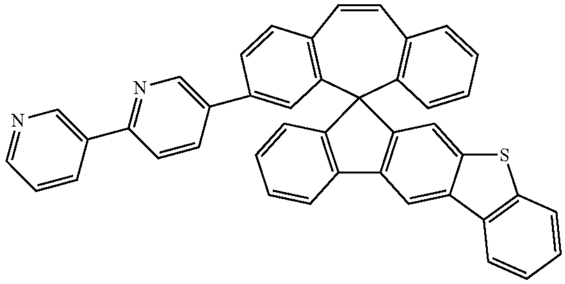
;
Compound XIII
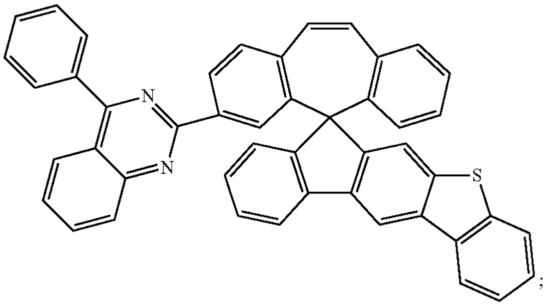
;
Compound XIV
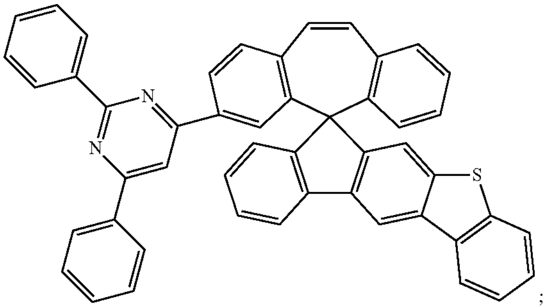
;
-continued
Compound XV
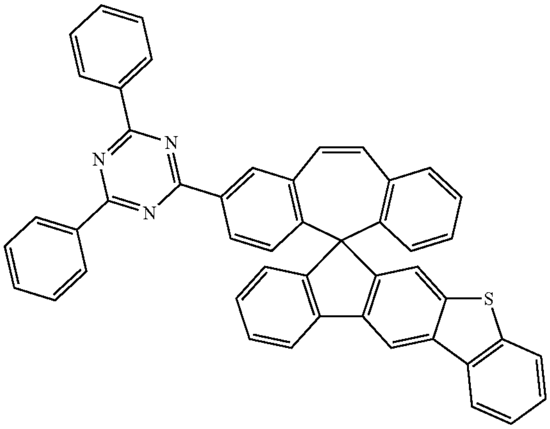
;
Compound XVI
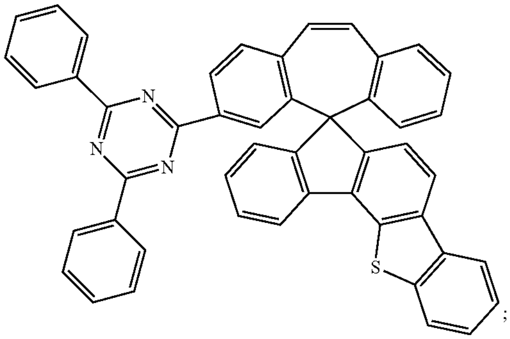
;
and
Compound XVII
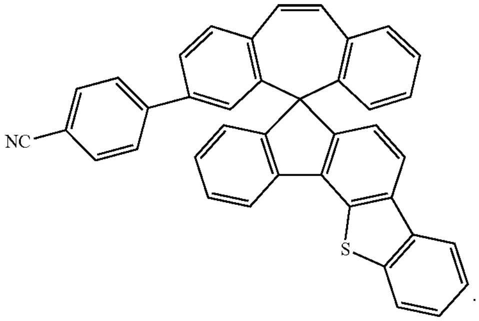
.
* * * * *